United States Patent
Rebar et al.

(10) Patent No.: US 7,026,462 B2
(45) Date of Patent: Apr. 11, 2006

(54) REGULATION OF ANGIOGENESIS WITH ZINC FINGER PROTEINS

(75) Inventors: Edward Rebar, El Cerrito, CA (US); Andrew Jamieson, San Francisco, CA (US); Qiang Liu, Foster City, CA (US); Pei-Qi Liu, Richmond, CA (US); Alan Wolffe, deceased, late of Orinda, CA (US); by Elizabeth J. Wolffe, legal representative, Orinda, CA (US); Stephen P. Eisenberg, Boulder, CO (US); Eric Jarvis, Boulder, CO (US)

(73) Assignee: Sangamo BioSciences, Inc., Richmond, CA (US)

( * ) Notice: Subject to any disclaimer, the term of this patent is extended or adjusted under 35 U.S.C. 154(b) by 305 days.

(21) Appl. No.: 10/006,069

(22) Filed: Dec. 6, 2001

(65) Prior Publication Data

US 2003/0021776 A1 Jan. 30, 2003

Related U.S. Application Data

(63) Continuation-in-part of application No. 09/846,033, filed on Apr. 30, 2001, which is a continuation-in-part of application No. 09/736,083, filed on Dec. 12, 2000, now abandoned, which is a continuation-in-part of application No. 09/733,604, filed on Dec. 7, 2000, now abandoned.

(51) Int. Cl.
*C07H 21/02* (2006.01)
*A01N 43/04* (2006.01)

(52) U.S. Cl. ........................ 536/23.1; 514/44

(58) Field of Classification Search .............. 514/44; 536/23.1, 23.4, 24.5
See application file for complete search history.

(56) References Cited

U.S. PATENT DOCUMENTS

| | | |
|---|---|---|
| 4,456,550 A | 6/1984 | Dvorak et al. |
| 4,990,607 A | 2/1991 | Katagiri et al. |
| 5,073,492 A | 12/1991 | Chen et al. |
| 5,096,814 A | 3/1992 | Aivasidis et al. |
| 5,096,815 A | 3/1992 | Ladner et al. |
| 5,194,596 A | 3/1993 | Tischer et al. |
| 5,198,346 A | 3/1993 | Ladner et al. |
| 5,219,596 A | 6/1993 | Smith et al. |
| 5,219,739 A | 6/1993 | Tischer et al. |
| 5,223,409 A | 6/1993 | Ladner et al. |
| 5,240,848 A | 8/1993 | Keck et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,332,671 A | 7/1994 | Ferrara et al. |
| 5,340,739 A | 8/1994 | Stevens et al. |

(Continued)

FOREIGN PATENT DOCUMENTS

| | | |
|---|---|---|
| EP | 0 126 153 | 6/1984 |
| EP | 0 484 401 | 7/1990 |
| EP | 0 464 155 | 10/1990 |
| EP | 0 471 754 | 11/1990 |
| EP | 0 506 477 | 9/1992 |
| EP | 0 935 001 | 8/1995 |
| EP | 0875567 A2 | 11/1998 |
| EP | 0 476 983 | 3/2000 |
| WO | WO 95/19431 | 7/1995 |
| WO | WO 95/24473 | 9/1995 |
| WO | WO 96/06110 | 2/1996 |
| WO | WO 96/06166 | 2/1996 |
| WO | WO 96/11267 | 4/1996 |
| WO | WO 96/11269 | 4/1996 |
| WO | WO 96/20951 | 7/1996 |

(Continued)

OTHER PUBLICATIONS

Sif et al (J. of Virol. Nov. 1994;68(11):7131–7138).*
P38082 EMBL/GenBank/DDBJ database, submitted 1994.*
Crystal, R.G. (Science, vol. 270, Oct. 1995, pp. 404–410).*
Tait et al. (Clin.Canc.Res., vol. 5, Jul. 1999, pp. 1708–1714).*
Gura (Science, v278, 1997, pp. 1041–1042).*
Agarwal et al., "Stimulation of Transcript Elongation Requires both the Zinc Finger and RNA Polymerase II Binding Domains of Human TFIIS," *Biochemistry*, 30(31):7842–7851 (1991).
Achen et al., "Vascular endothelial growth factor D (VEGF–D) is a ligand for the tyrosine kinases VEGF receptor 2 (Flk1) and vEGF receptor 3 (Flt4)," *PNAS*, 95:549–553 (1998).
Akiri et la. "Regulation of Vascular Endothelial Growth Factor (VEGF) expression is mediated by internal initiation of translation and alternative initiation of transcription," *Oncogene*, 17:227–236 (1998).
Antao et al., "A thermodynamic study of unusually stable RNA and DNA hairpins," *Nuc. Acids. Res.*, 19(21):5901–5905 (1991).

*Primary Examiner*—G. Nickol
*Assistant Examiner*—C. Yaen
(74) *Attorney, Agent, or Firm*—Townsend and Townsend and Crew LLP

(57) ABSTRACT

Provided herein are a variety of methods and compositions for regulating angiogenesis, such methods and compositions being useful in a variety of applications where modulation of vascular formation is useful, including, but not limited to, treatments for ischemia and wound healing. Certain of the methods and compositions accomplish this by using various zinc finger proteins that bind to particular target sites in one or more VEGF genes. Nucleic acids encoding the zinc finger proteins are also disclosed. Methods for modulating the expression of one or more VEGF genes with the zinc finger proteins and nucleic acids are also disclosed. Such methods can also be utilized in a variety of therapeutic applications that involve the regulation of endothelial cell growth. Pharmaceutical compositions including the zinc finger proteins or nucleic acids encoding them are also provided.

7 Claims, 33 Drawing Sheets

U.S. PATENT DOCUMENTS

| | | | |
|---|---|---|---|
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,607,918 A | 3/1997 | Eriksson et al. |
| 5,639,592 A | 6/1997 | Evans et al. |
| 5,674,738 A | 10/1997 | Abramson et al. |
| 5,702,914 A | 12/1997 | Evans et al. |
| 5,776,755 A | 7/1998 | Alitalo et al. |
| 5,789,538 A | 8/1998 | Rebar et al. |
| 5,792,640 A | 8/1998 | Chandrasegaran |
| 5,840,693 A | 11/1998 | Eriksson et al. |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,928,939 A | 7/1999 | Eriksson et al. |
| 5,932,540 A | 8/1999 | Rosen et al. |
| 5,935,820 A | 8/1999 | Rosen et al. |
| 5,939,538 A | 8/1999 | Leavitt et al. |
| 5,972,615 A | 10/1999 | An et al. |
| 5,994,300 A | 11/1999 | Bayne et al. |
| 6,001,885 A | 12/1999 | Vega et al. |
| 6,007,408 A | 12/1999 | Sandhu |
| 6,007,988 A | 12/1999 | Choo et al. |
| 6,013,453 A | 1/2000 | Choo et al. |
| 6,040,157 A | 3/2000 | Hu et al. |
| 6,130,071 A | 10/2000 | Alitalo et al. |
| 6,140,073 A | 10/2000 | Bayne et al. |
| 6,140,081 A | 10/2000 | Barbas |
| 6,599,692 B1 * | 7/2003 | Case et al. |

FOREIGN PATENT DOCUMENTS

| | | |
|---|---|---|
| WO | WO 96/26736 | 9/1996 |
| WO | WO 96/27007 | 9/1996 |
| WO | WO 96/32475 | 10/1996 |
| WO | WO 96/39515 | 12/1996 |
| WO | WO 97/05250 | 2/1997 |
| WO | WO 97/09427 | 3/1997 |
| WO | WO 97/17442 | 5/1997 |
| WO | WO 97/27212 | 7/1997 |
| WO | WO 97/27213 | 7/1997 |
| WO | WO 98/07832 | 2/1998 |
| WO | WO 98/10071 | 3/1998 |
| WO | WO 98/10078 | 3/1998 |
| WO | WO 98/24811 | 6/1998 |
| WO | WO 98/33917 | 8/1998 |
| WO | WO 98/49300 | 11/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/33485 | 7/1999 |
| WO | WO 99/36553 | 7/1999 |
| WO | WO 99/37671 | 7/1999 |
| WO | WO 99/40197 | 8/1999 |
| WO | WO 99/41371 | 8/1999 |
| WO | WO 99/42474 | 8/1999 |
| WO | WO 99/45132 | 9/1999 |
| WO | WO 99/46364 | 9/1999 |
| WO | WO 99/47656 | 9/1999 |
| WO | WO 99/47677 | 9/1999 |
| WO | WO 99/48909 | 9/1999 |
| WO | WO 99/50290 | 10/1999 |
| WO | WO 00/09148 | 2/2000 |
| WO | WO 00/23464 | 4/2000 |
| WO | WO 00/25805 | 5/2000 |
| WO | WO 00/27878 | 5/2000 |
| WO | WO 00/37641 | 6/2000 |
| WO | WO 00/41566 | 7/2000 |
| WO | WO 00/42219 | 7/2000 |
| WO | WO 00/44903 | 8/2000 |
| WO | WO 00/45835 | 8/2000 |
| WO | WO 01/83732 A2 | 11/2001 |
| WO | WO 01/83793 A2 | 11/2001 |
| WO | WO 01/83819 A2 | 11/2001 |
| WO | WO 01/84148 A2 | 11/2001 |

OTHER PUBLICATIONS

Barbas et al., "Assembly of combinatorial antibody libraries on phage surfaces: The gene III site," *PNAS*, 88:7978–7982 (1991).

Barbas et al., "Semisynthetic combinatorial antibody libraries: A chemical solution to the diversity problem," *PNAS*, 89:4457–4461 (1992).

Barbas, C. F., "Recent advances in phage display," *Curr. Opin. Biotech.*, 4:526–530 (1993).

Bartsevich et al., "Regulation of the MDR1 Gene by Transcriptional Repressors Selected using peptide Combinatorial Libraries," *Mol. Pharmacol.*, 58:1–10 (2000).

Beerli et al., "Positive and Negative Regulation of Endogenous Genes Designed by Transcription Factors," *PNAS*, 97: 1495–1500 (2000).

Beerli, R.R. et al. "Toward controlling gene expression at will: Specific regulation of the *erbB–2/HER–2* promoter by using polydactyl zinc finger proteins constructed from modular building blocks," *PNAS*, 95:14628–14633 (1998).

Bellefroid et al., "Clustered organization of homologous KRAB zinc–finger genes with enhanced expression in human T lymphoid cells," *EMBL J.*, 12(4):1363–1374 (1993).

Berg et al., "The Galvanization of Biology: A Growing Appreciation for the Roles of Zinc," *Science*, 271:1081–1085 (1996).

Berg, J. M., "DNA Binding Specificity of Steroid Receptors," *Cell*, 57:1065–1068 (1989).

Berg, J. M., "Sp1 and the subfamily of zinc finger proteins with guanine–rich binding sites," *PNAS*, 89:11109–11110 (1992).

Berg, J. M., "Letting your fingers do the walking," *Nature Biotechnology*, 15:323 (1997).

Bergqvist et al., "Loss of DNA–binding and new transcription trans–activation function in polyomavirus large T–antigen with mutation of zinc finger motif," *Nuc. Acids Res.*, 18(9):2715–2720 (1990).

Birkenhager, R., "Synthesis and physiological activity of heterodimers comprising different splice forms of vascular endothelial growth factor and placenta growth factor," *Biochem. J.*, 316:703–707 (1996).

Blaese et al., "Vectors in cancer therapy: how will they deliver?," *Cancer Gene Therapy*, 2(4):291–297 (1995).

Cao, Y. "Heterodimers of Placenta Growth Factor/Vascular Endothelial Growth Factor," *J. Biol. Chem.*, 271: 3154–3162 (1996).

Cao, Y. "Placenta Growth Factor: Identification and Characterization of a Novel Isoform Generated by RNA Alternative Splicing," *Biochem. Biophys. Res Commun.*, 235: 493–498 (1997).

Caponigro et al., "Transdominant genetic analysis of a growth control pathway," *PNAS*, 95:7508–7513 (1998).

Carmeliet et al., "Abnormal blood vessel development and lethality in embryos lacking a single VEGF allel.," *Nature*, 380: 435–442 (1996).

Carmeliet et al., "Impaired myocardial angiogenesis and ischemic cardiomyopathy in mice lacking the vascular endothelial growth factor isoforms VEGF 164 and VEGF 188," *Nature Med.*, 5: 495–502 (1999).

Celenza et al., "A Yeast Gene That Is Essential for Release from Glucose Repression Encodes a Protein Kinase," *Science*, 233:1175–1180 (1986).

Cheng et al., "A Single Amino Acid substitution in Zinc Finger 2 of Adr1p Changes its Binding Specificity at two Positions in UAS1," *J. Mol. Biol.*, 251:1–8 (1995).

Cheng et al., "Identification of Potential Target Genes for Adr1p through Characterization of Essential Nucleotides in UAS1," *Mol. Cellular Biol.*, 14(6):3842–3852 (1994).

Choo et al., "A role in DNA binding for the linker sequences of the first three zinc fingers of TFIIIA," *Nuc. Acids Res.*, 21(15):3341–3346 (1993).

Choo et al., "Advances in Zinc Finger Engineering," *Current Opinion in Structural Biology*, 10:33850–3860 (2000).

Choo et al., "All wrapped up," *Nature Structural Biology*, 5(4):253–255 (1998).

Choo et al., "Designing DNA–binding proteins on the surface of filamentous phage," *Curr. Opin. Biotechnology*, 6:431–436 (1995).

Choo et al., "Physical basis of a protein–DNA recognition code," *Curr. Opin. Struct. Biol.*, 7(1):117–125 (1997).

Choo et al., "Promoter–specific Activation of Gene Expression Directed by Bacteriophage–selected Zinc Fingers," *J. Mol. Biol.*, 273:525–532 (1997).

Choo, Y. and Klug, A. "Selection of DNA binding sites for zinc fingers using rationally randomized DNA reveals coded interactions." *PNAS*, 91:11168–11172 (1994).

Choo, Y. and Klug, A. Toward a code for the interactions of zinc fingers with DNA: Selection of randomized fingers displayed on phage. *PNAS*, 91:11163–11167 (1994).

Choo, Y. et al. "In vivo repression by a site–specific DNA–binding protein designed against an oncogenic sequence." *Nature*, 372:642–645 (1994).

Choo, Y., "End effects in DNA recognition by zinc finger arrays," *Nuc. Acids Res.*, 26(2):554–557 (1998).

Choo, Y., "Recognition of DNA methylation by zinc fingers," *Nature Struct. Biol.*, 5(4):264–265 (1998).

Chua et al., J. "Interleukin 6 Induces the expression of Vascular Endothelial Growth Factor," *Biol. Chem.*, 271:736–741 (1996).

Clarke et al., "Zinc Fingers in *Caernorhabditis elegans:* Finding Families and Probing Pathways," *Science*, 282:2018–2022 (1998).

Clauss, M., "The Vascular Endothelial Growth Factor Receptor Flt–1 Mediates Biological Activities," *J. Biol. Chem.*, 271: 17629–17634 (1996).

Cohen, et al., "Interleukin 6 Induces the Expression of Vascular Endothelial Growth Factor," *The Journal of Biological Chemistry*, 271(2):736–741 (1996).

"Collateral Therapeutics Inc. (CLTX) Announces Research On New Angiogenic Growth Factor Gene VEGF–138," (Nov. 30, 2000) published at BioSpace.com.

Connolly, "Vascular Permeability Factor: A Unique Regulator of Blood Vessel Funtion" *J. Cellular Biochem.*, 47: 219–223 (1991).

Corbi et al., "Synthesis of a New Zinc Finger Peptide; Comparison of Its 'Code' Deduced and 'CASTing' Derived Binding Sites," *FEBS Letters*, 417:71–74 (1997).

Crozatier et al., "Single Amino Acid Exchanges in Separate Domains of the *Drosophila serendipity* δ Zinc Finger Protein Cause Embryonic and Sex Biased Lethality," *Genetics*, 131:905–916 (1992).

Damert et al., Activator–protein–1 binding petentiates the hypoxia–inducible factor–1 mediated hypoxia–induced transcriptional activation of vascular–endothelial growth factor expression in C6 glioma cells, *Biochem. J.* 327: 419–423 (1997).

Debs et al., "Regulation of Gene Expression in Vivo by Liposome–mediated Delivery of a Purified Transcription factor," *J. Biological Chemistry*, 265(18):10189–10192 (1990).

Desjarlais et al., "Redesigning the DNA–Binding Specificity of a Zinc Finger Protein: A Data Base–Guided Approach," *Proteins: Structure, Function, and Genetics*, 12(2):101–104 (1992).

Desjarlais et al., "Redesigning the DNA–Binding Specificity of a Zinc Finger Protein: A Data Base–Guided Approach," *Proteins: Structure, Function, and Genetics*, 13(3):272 (1992).

Desjarlais, J.R. and Berg, J.M. "Length–encoded multiplex binding site determination: Application to zinc finger proteins," *PNAS*, 91:11099–11103 (1994).

Desjarlais, J.R. and Berg, J.M. "Toward rules relating zinc finger protein sequences and DNA binding site preferences," *PNAS*, 90:7345–7349 (1992).

Desjarlais, J.R. and Berg, J.M. "Use of a zinc–finger consensus sequence framework and specificity rules to design specific DNA binding proteins," *PNAS*, 90:2256–2260 (1993).

Diaz et al., "Regulation of Vascular Endothelial Growth Factor Expression in Human Keratincytes by Retinoids," *J. Biol. Chem.*, 275:642–650 (2000).

DiBello et al., "The Drosophila Broad–Complex Encodes a Family of Related Proteins Containing Zinc Fingers," *Genetics*, 129:385–397 (1991).

Dreier et al. "Insights into the Molecular Recognition of the 5'GNN–3' Family of DNA Sequences by Zinc Finger Domains," *J. Mol. Biol.*, 303:489–502 (2000).

Elrod–Erickson et al., "High–resolution structures of variant Zif268–DNA complexes: implications for understanding zinc finger–DNA recognition," *Structure*, 6(4):451–464 (1998).

Elrod–Erickson et al.,"Zif268 protein–DNA complex refined at 1.6 Å: a model system for understanding zinc finger–DNA interactions," *Structure*, 4(10):1171–1180 (1996).

Esakof et al., "Intraoperative Multiplane Transesophageal Echocardiography for Guiding Direct Myocardial Gene Transfer of Vascular Endothelial Growth Factor in Patients with Refractory Angina Pectoris," *Hum. Gene Ther.*, 10:2307–2314 (1999).

Fairall et al., "The crystal structure of a two zinc–finger peptide reveals an extension to the rules for zinc–finger/DNA recognition," *Nature*, 366:483–487 (1993).

Ferrara et al., "Heterozygous embryonic lethality induced by targeted inactivation of thte VEGF gene," *Nature*, 380: pp. 439–442 (1996).

Ferrara et al., "The Vascular Endothelial Growth Factor Family of Polypeptides," *J. Cellular Biochem.*, 47:211–218.(1991).

Forsythe et al., "Activation of Vascular Endothelial Growth Factor Gene Transcription by Hypoxia–Inducible Factor 1," *Mol. Cell. Biol.*, 16:4604–4613 (1996).

Frankel, et al., "Fingering Too Many Proteins," *Cell*, 53:675 (1988).

Friesen et al., "Phage Display of RNA Binding Zinc Fingers from Transcription Factor IIIA*," *J. Biological Chem.*, 272(17):10994–10997 (1997).

Friesen et al., "Specific RNA binding proteins constructed from zinc fingers," *Nature Structural Biology*, 5(7):543–546(1998).

Gen Bank Accession No. V41383 (6I 1134964) "*Mus musculus* Vascular Endothelial Growth Factor (VEGF) Gene, Partial eds. and Promoter Region," (Apr. 17, 1996).

GenBank Accession No. AC015837 (GI7407936) *Homo sapiens*, clone RP11–23117, (Apr. 4, 2000).

GenBank Accession No. AF 106020 (GI4139223) "A Novel Vascular Endothelial Growth factor Encoded by Orf Virus, VEGF E, mediates angiogensis via signalling through VEGFR–2 (KDR) but not VEGFR–1 (Flt–1) receptor tyrosine Kinases," (Mar. 11, 1999).

GenBank Accession No. AF020393 (GI2582366) Genomic organization of human and mouse genes for vascular endothelial growth factor C, (Nov. 2, 1997).

GenBank Accession No. AF095785 (GI4154290) "Two novel plymorphisms in the promoter region of the human vascular endothelial growth factor (VEGF)gene," (Jan. 14, 1999).

GenBank Accession No. HSU 69570 (GI 1825473) "Direct Submission," (Feb. 7, 1997).

GenBank Accession No. HSU80601 (GI 1815657) "Analysis of the Promoter Region of the Human VEGF– related Factor Gene," (Feb. 5, 1997).

GenBank Accession No. HSY 12864 (GI 2909351) "Human FIG F: cloning, gene structure, and mapping to chromosome Xp22.1 between the PIGA and the GRPR genes," (Aug. 2, 1999).

GenBank Accession No. S67520 (GI 456897) "Homologs of Vascular Endothelial Growth Factor are Encoded by the Poxvirus Orf Virus," *J. Virol.*, 68 (1):84–92 (1994).

GenBank Accession No.AF091434 (GI6002592) "*Homo sapiens* secretory growth factor–like protein fallotein mRNA, complete cds," (Jun. 22, 2000).

GenBank Acesion No. U80601 "Human novel unknown gene, partial 3'UTR, and VEGF–related factor (VRF) gene, promoter region," (Feb. 5, 1997).

Gogos et al., "Recognition of diverse sequences by class I zinc fingers: Asymmetries and indirect effects on specificity in the interaction between CF2II and A+T–rich sequence elements," *PNAS*, 93(5):2159–2164 (1996).

Gossen et al., "Tight control of gene expression in mammalian cells by tetracycline–responsive promoters," *PNAS*, 89:5547–5551 (1992).

Ghosh, D., "A relational database of transcription factors," *Nuc. Acids Res.*, 18(7):1749–1756 (1990).

Grant et al., "Exploring the Role of Glutamine 50 in the Homeodomain DNA Interface: Crystal Structure of Engraled (Gln50→Ala) Complex at 2.0Å)," *Biochemistry*, 39:8187–8192 (2000).

Greisman, H.A. and Pabo, C.O. "A general strategy for selecting high–affinity zinc finger proteins for diverse DNA target sites," *Science*, 275:657–661. (1997).

Grunstein et al., "Isoforms of Vascular Endothelial Growth Factor Act in a Coordinate Fashino to Recruit and Expand Tumor Vasculature," *Mol. Cell. Biol.*, 20:728–7291 (2000).

Hamilton et al., "Comparison of the DNA Binding Characteristics of the Related Zinc Finger Proteins WT1 and EGR1," *Biochemistry*, 37:2051–2058 (1998).

Hamilton et al., "High affinity binding sites for the Wilms' tumor suppressor protein WT1," *Nuc. Acids Res.*, 23(2):277–284 (1995).

Hanas et al., "Internal deletion mutants of Xenopus transcription factor IIIA," *Nuc. Acids Res.*, 17(23):9861–9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600–11605 (1992).

Heinzel et al., "A complex containing N–CoR, mSin3 and histone deacetylase mediates transcriptional repression," *Nature*, 387:43–48 (1997).

Hendel et al., "Effect of Intracoronary Recombinant Human Vascular Endothelial Growth Factor on Myocardial Perfusion," *Circulation* 101:118–121 (2000).

Hirst et al., "Discrimination of DNA response elements for thyroid hormone and estrogen is dependent on dimerization of receptor DNA binding domains," *PNAS*, 89:5527–5531 (1992).

Hoffman et al., "Structures of DNA–binding mutant zinc finger domains: Implications for DNA binding," *Protein Science*, 2:951–965 (1993).

Ikeda et al., "Hypoxia–induced Transcriptional Activation and Increased mRNA Stability of Vascular Endothelial Growth Factor in C6 Glioma Cells," *J. Biol.Chem.*, 270: 19, 761–19, 766 (1995).

Isalan et al., "Comprehensive DNA Recognition through Concerted Interactions from Adjacent Zinc Fingers," *Biochemistry*, 37:12026–12033 (1998).

Isalan et al., "Synergy between adjacent zinc fingers in sequence–specific DNA recognition," *PNAS*, 94(11):5617–5621 (1997).

Isner et al., "Clinical evidence of angiogenesis after arterial gene transfer of phVEGF 165 in pateint with ischaemic limb," *Lancet*, 348:370–374 (1996).

Jacobs, G. H., "Determination of the base recognition positions of zinc fingers from sequence analysis," *EMBO J.*, 11(12):4507–4517 (1992).

Jamieson et al., "A zinc finger directory for high–affinity DNA recognition," *PNAS*, 93:12834–12839 (1996).

Jamieson, A.C. et al. "In vitro selection of zinc fingers with altered DNA–binding specificity," *Biochemistry*, 33:5689–5695 (1994).

Joukov et al., "A novel vascular endothelial growth factor, VEGFC, is a ligand for the Flt4 (VEGFR–3) and KDR (VEGFR–2) receptor tyrosine kinases," *EMBO J.* 15: 290–298 (1996).

Julian et al., "Replacement of His23 by Cys in a zinc finger of HIV–1 NCp7 led to a change in 1H NMR–derived 3D structure and to a loss of biological activity," *FEBS Letters*, 331(1,2):43–48 (1993).

Kamiuchi et al., "New multi zinc finger protein: biosynthetic design and characteristics of DNA recognition," *Nucleic Acids Symposium Series*, 37:153–154 (1997).

Kang et al., "Zinc Finger Proteins as Designer Transcription Factors," *J. Biol. Chem.*, 275(12):8742–8748 (2000).

Keck et al., "Vascular Permeability Factor, an Endothelial Cell Mitogen Related to PDGF," *Science*, 246: 1309–1312 (1989).

Kim et al., "A 2.2 Å resolution crystal structure of a designed zinc finger protein bound to DNA," *Nat. Struct. Biol.*, 3(11):940–945 (1996).

Kim et al., "Design of TATA box–binding protein/zinc finger fusions for targeted regulation of gene expression," *PNAS*, 94:3616–3620 (1997).

Kim et al., "Hybrid restriction enzymes: Zinc finger fusions to *Fok* I cleavage domain," *PNAS*, 93:1156–1160 (1996).

Kim et al., "Serine at Position 2 in the DNA Recognition helix of a Cys2–His2 Zinc finger Peptide is Not, in General, Responsible for Base Recognition," *J. Mol. Biol.*, 251:1–5 (1995).

Kim et al., "Site–specific cleavage of DNA–RNA hybrids by zinc finger/*FokI* cleavage domain fusions," *Gene*, 203:43–49 (1997).

Kim, J–S. and Pabo, C.O. "Getting a handhold on DNA: Design of poly–zinc finger proteins with femtomolar dissociation constants," *PNAS*, 95:2812–2817 (1998).

Kim, J–S. and Pabo, C.O. "Transcriptional repression by zinc finger peptides," *The Journal of Biological Chemistry*, 272:29795–28000 (1997).

Kimura et al., "Hypoxia resonse element of the human vascular endothelial growth factor gene mediates transcriptional regulation by nitric oxide: control of hypoxia–inducible factor–1 activity by nitric oxide," *Blood*, 95: 189–197 (2000).

Kinzler et al., "The GLI gene is a member of the Kruppel family of zinc finger proteins," *Nature*, 332:371–4 (1988).

Klug et al., "Protein Motifs 5: Zinc Fingers," *FASEB J.*, 9:597–604 (1995).

Klug, "Zinc Finger Peptides for the Regulation of Gene Expression," *J. Mol. Biol.*, 293:215–218 (1999).

Klug, A., "Gene Regulatory Proteins and Their Interaction with DNA," *Ann. NY Acad. Sci.*, 758:143–160 (1995).

Kothekar, "Computer Simulation of Zinc Finger Motifs from Cellular Nucleic Acid Binding Proteins and their Interactions with Consensus DNA Sequences," *FEBS Letters*, 274(1,2):217–222 (1990).

Kriwacki et al., "Sequence–Specific Recognition of DNA by Zinc–Finger Peptides Derived from the Transcription Factor Sp1," *PNAS*, 89:9759–9763 (1992).

Kudla et al., "The regulatory gene area mediating nitrogen metabolite repression in *Aspergillus nidulans*. Mutations affecting specificity of gene activation after a loop residue of a putative zinc finger," *EMBO J.*, 9(5):1355–1364 (1990).

Ladoux et al., "Cobalt Stimulates the Expression of Vascular Endothelial Growth Factor mRNA in Rat Cardiac Cells," *Biochem Biophys. Res. Commun.* 204:794–798 (1994).

Laird–Offringa et al., "RNA–binding proteins tamed," *Nat. Structural Biol.*, 5(8):665–668 (1998).

Lee et al., "Vascular endothelial growth factor–related protein: A ligand and specific activator of the tyrosine kinase receptor Flt4," *PNAS*, 93: 1988–1992 (1996).

Leung et al., k "Vascular Endothelial Growth Factor Is a Secreted Angiogenic Mitogen," *Science*, 246: 1306–1309 (1989).

Levy et al., Transcriptional Regulation of the Rat Vascular Endothelial Growth Factor Gene by Hypoxia, *J. Biol. Chem.*, 270: 13,333–13, 340 (1995).

Liu et al., "Hypoxia Regulates Vascular Endothelial Growth Factor Gene Expression in Endothelial Cells," *Circ. Res.*, 77: 638–643 (1995).

Liu, Q. et al. "Design of polydactyl zinc–finger proteins for unique addressing within complex genomes," *PNAS*, 95:5525–5530 (1997).

Lyttle, D.J. et al., "Homologs of Vascular Endothelial Growth Factor are Encoded by the Poxvirsu Orf Virus," *J. Virology*, 68: 84–92 (1994).

Maglione et al., "Isolation of a human placenta cDNA coding for a prtein related to the vascular permeability factor," *PNAS*, 88: 9267–9271 (1991).

Mandel–Gutfreund et al., "Quantitative parameters for amino acid–base interaction: implications for prediction of protein–DNA binding sites," *Nuc. Acids Res.*, 26(10):2306–2312 (1998).

Margolin et al., "Kruppel–associated boxes are potent transcriptional repression domains," *PNAS*, 91:4509–4513 (1994).

McNamara et al., "A novel four zinc–finger protein targeted against p190 (BcrAbl) fusion oncogene cDNA: utilization of zinc–finger recognition codes," *Nucleic Acids Research*, 28(24):4865–4872 (2000).

Meyer et al., "A Novel Vascular Endothelial Growth Factor Encoded by Orf virus, VEGF–E, mediates angiogenesis via signalling through VEGFR–2 (KDR) bu not VEGFR 1 (flt–1) receptor Tyrosine Kinases," *EMBO J.*, 18: 363–374 (1999).

Migdal et al., "Neuropilin–1 Is a Placenta Growth Factor–2 receptor," *J.Biol. Chem.*, 273:22272–22278 (1998).

Milanini et al., "p42/p44 MAP Kinase Module Plays a Key Role in the Transcriptional Regulation of the Vascular Endothelial Growth Factor Gene in Fibroblasts," *J. Biol. Chem.*, 273: 18, 165–18,172 (1998).

Mizushima et al., "pEF–BOS, a powerful mammalian expression vector," *Nuc. Acids Res.*, 18(17):5322 (1990).

Nakagama et al., "Sequence and Structural Requirements for High–Affinity DNA Binding by the WT1 Gene Product," *Molecular and Cellular Biology*, 15(3):1489–1498 (1995).

Nardelli et al., "Base sequence discrimination by zinc–finger DNA–binding domains," *Nature*, 349:175–178 (1991).

Nardelli et al., "Zinc finger–DNA recognition: analysis of base specificity by site–directed mutagenesis," *Nuc. Acids Res.*, 20(16):4137–4144 (1992).

Nekludova et al., "Distinctive DNA conformation with enlarged major groove is found in Zn–finger—DNA and other protein—DNA complexes," *PNAS*, 91:6948–6952 (1994).

Ogawa, S. et al., A Novel Type of Vascular Endothelial Growth Factor, VEGF–E (NZ–7 VEGF), Preferentially Utilizes KDR/FLK–1 Receptor and Carries a Potent Mitotic Activity without Heparin–binding Domain, *J. Biol. Chem.*, 273:31273–31282 (1998).

Olofsson et al., "Vascular endothelial growth factor B, a novel growth factor for endothelial cells," *PNAS*, 93: 2576–2581 (1996).

Orkin et al., "Report and Recommendations of the Panel to Assess the NIH Investment in Research on Gene Therapy," *NIH Homepage*, 41 pages total (1995).

Pabo et al., "Geometric Analysis and Comparison of Protein–DNA Interfaces: Why is there no simple code for recognition," *J. Mol. Biol.*, 301:597–635 (2000).

Pabo et al., "Protein–DNA Recognition," *Ann. Rev. Biochem.*, 53:293–321 (1984).

Pabo et al., "Systematic Analysis of Possible Hydrogen Bonds between Amino Acid Side Chains and B–form DNA," *J. Biomolecular and Struct. Dynamics*, 1:1039–1049 (1983).

Pabo, C. O., "Transcription Factors: Structural Families and Principals of DNA Recognition," *Ann. Rev. Biochem.*, 61:1053–1095 (1992).

Pavletich et al., "Crystal Structure of a Five–Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 Å," *Science*, 252:809–817 (1991).

Pengue et al., "Kruppel–associated box–mediated repression of RNA polymerase II promoters is influenced by the arrangement of basal promoter elements," *PNAS*, 93:1015–1020 (1996).

Pengue et al., "Repression of transcriptional activity at a distance by the evolutionarily conserved KRAB domain present in a subfamily of zinc finger proteins," *Nuc. Acids Res.*, 22(15):2908–2914 (1994).

Pengue et al., "Transcriptional Silencing of Human Immunodeficiency Virus Type 1 Long Terminal Repeat–Driven Gene Expression by the Kruppel–Associated Box Repressor Domain Targeted to the Transactivating Response Element," *J. Virology*, 69(10):6577–6580 (1995).

Pettersson et al., "Heterogeneity of the Angiogenic Response Induced in Different Normal Adult Tissues by Vascular Permeability Factor/Vascular Endothelial Growth Factor," *Laboratory Investigation*, 80:99–115 (2000).

Pomerantz et al., "Analysis of homeodomain function by structure–based design of a transcription factor," *PNAS*, 92:9752–9756 (1995).

Pomerantz et al., "Structure–Based Design of a Dimeric Zinc Finger Protein," *Biochemistry*, 37(4):965–970 (1998).

Pomerantz, J.L. et al. "Structure–based design of transcription factors," *Science*, 267:93–96 (1995).

Qian et al., "Two–dimensional NMR Studies of Zinc Finger Motif: Solution Structures and Dynamics of Mutant ZFY Domains Containing Aromatic Substitutions in the Hydrophobic Core," *Biochemistry*, 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor in Vivo," *Molecular Endocrinology*, 6(7):1103–1112 (1992).

Rauscher et al., "Binding of the Wilms' Tumor Locus Zinc Finger Protein to the EGR–1 Consensus Sequence," *Science*, 250:1259–1262 (1990).

Ray et al., "Repressor to activator switch by mutations in the first Zn finger of the glucocoricoid receptor: Is direct DNA binding necessary?," *PNAS*, 88:7086–7090 (1991).

Rebar et al., "Phage Display Methods for Selecting Zinc Finger Proteins with Novel DNA–Binding Specificities," *Methods in Enzymology*, 267:129–149 (1996).

Rebar, E.J. and Pabo, C.O. "Zinc finger phage: Affinity selection of fingers with new DNA–binding Specificities," *Science*, 263:671–673 (1994).

Reith et al., "Cloning of the major histocompatibility complex class II promoter binding protein affected in a hereditary defect in class II gene regulation," *PNAS*, 86:4200–4204 (1989).

Rhodes et al., "Zinc Fingers: They play a key part in regulating the activity of genes in many species, from yeast to humans. Fewer than 10 years ago no one knew they existed," *Scientific American*, 268:56–65 (1993).

Rice et al., "Inhibitors of HIV Nucleocapsid Protein Zinc Fingers as Candidates for the Treatment of AIDS," *Science*, 270:1194–1197 (1995).

Rivera et al., "A humanized system for pharmacologic control of gene expression," *Nature Medicine*, 2(9):1028–1032 (1996).

Rollins et al., "Role of TFIIIA Zinc Fingers In vivo: Analysis of Single–Finger Function in Developing Xenopus Embryos," *Molecular Cellular Biology*, 13(8):4776–4783 (1993).

Rosengart et al., "Angiogenesis Gene Therapy– Phase I Assessment of Direct Intramyocardial Administration of an Adenovirus Vector expressing VEGF121 cDNA to Individuals with Clinically Significant Severe Coronary Artery Disease," *Circulation*, 100: 468–474 (1999).

Rosengart et al., "Six–Month Assessment of a Phase 1 Trial of Angiogenic Gene Therapy for the Treatment of Coronary Artery Disease Using Direct Intramyocardial Administration of an Adenovirus Vector Expression the VEGF121 cDNA," *Ann. Surg.*, 230: 466–470 (1999).

Ruben et al., "Isolation of rel–Related Human cDNA that Potentially Encodes the 65–kD Subunit of NF–κB," *Science*, 251: 1490–1493 (1991).

Ryuto et al., "Induction of Vascular Endothelial Growth Factor by Tumor Necrosis Factor α in Human Glioma Cells," *J. Biol. Chem.*, 271:28, 220–28, 228 (1996).

Sadowski et al., "GAL4–VP16 is an unusually potent transcriptional activator," *Nature*, 335: 563–568 (1998).

Saleh et al., "A Novel Zinc Finger Gene on Human Chromosome Iqter That Is Alternatively Spliced in Human Tissues and Cell Lines," *Am. J. Hum. Genet.*, 52:192–203 (1993).

Salimath et al., "Expression of the vascular endothelial growth factor gene is inhibited by p73," *Oncogene*, 19: 3470–3476 (2000).

Segal et al. "Design of Novel Sequence–specific DNA–binding proteins," *Current Opinion in Chemical Bilology*, 4:34–39 (2000).

Segal et al. "Toward controlling gene expression at will: Selection and design of zinc finger domains recognizig each of the 5'–GNN–3' DNA target sequences," *PNAS*, 96:2758–2763 (1999).

Shi et al., "A direct comparison of the properties of natural and designed finger proteins," *Chem. & Biol.*, 2(2):83–89 (1995).

Shi et al., "DNA Unwinding Induced by Zinc Finger Protein Binding," *Biochemistry*, 35:3845–3848 (1996).

Shi et al., "Specific DNA–RNA Hybrid Binding by Zinc Finger Proteins," *Science*, 268:282–284 (1995).

Singh et al., "Molecular Cloning of an Enhancer Binding Protein: Isolation by Screening of an Expression Library with a Recognition Site DNA," *Cell*, 52:415–423 (1988).

Skerka et al., "Coordinate Expression and Distinct DNA–Binding Characteristics of the Four EGR–Zinc Finger Proteins in Jurkat T Lymphocytes," *Immunobiology*, 198:179–191 (1997).

Soker et al., "Neuropilin–1 Is Expressed by Endothelial and Tumor Cells as an Isoform–Specific Receptor for Vascular Endothelial Growth Factor," *Cell*, 92: 735–745 (1998).

South et al., "The Nucleocapsid Protein Isolated from HIV–1 Particle Binds Zinc and Forms Retroviral–Type Zinc Fingers," *Biochemistry*, 29:7786–7789 (1990).

Suzuki et al. "DNA recognition code of transcription factors in the helix–turn–helix, probe helix, hormone receptor, and zinc finger families," *PNAS*, 91:12357–12361 (1994).

Suzuki et al., "Stereochemical basis of DNA recognition by Zn fingers," *Nuc. Acids Res.*, 22(16):3397–3405 (1994).

Swimoff et al., "DNA–Binding Specificity of NGFI–A and Related Zinc Finger Transcription Factors," *Mol. Cell. Biol.*, 15(4):2275–2287 (1995).

Taylor et al, "Designing Zinc–Finer ADR1 Mutants with Altered Specificity of DNA Binding to T in UAS1 Sequences," *Biochemistry*, 34:3222–3230 (1995).

Thiesen et al., "Amino Acid Substitutions in the SP1 Zinc Finger Domain Alter the DNA Binding Affinity to Cognate SP1 Target Site," *Biochem. Biophys. Res. Communications*, 175(1):333–338 (1991).

Thiesen et al., "Determination of DNA binding Specificities of mutated zinc finger domains," *FEBS Letters*, 283(1):23–26 (1991).

Thukral et al., "Alanine scanning site–directed mutagenesis of the zinc fingers of transcription factor ADR1: Residues that contact DNA and that transactivate," *PNAS*, 88:9188–9192 (1991).

Thukral et al., "Alanine scanning site–directed mutagenesis of the zinc fingers of transcription factor ADR1: residues that contact DNA and that transactivate," *PNAS*, 90:7908 (1993).

Thukral et al., "Localization of a Minimal Binding Domain and Activation Regions in Yeast Regulatory Protein ADR1," *Molecular Cellular Biology*, 9(6):2360–2369 (1989).

Thukral et al., "Mutations in the Zinc Fingers of ADR1 That Change the Specificity of DNA Binding and Transactivation," *Mol. Cell Biol.*, 12(6):2784–2792 (1992).

Thukral et al., "Two Monomers of Yeast Transcription Factor ADR1 Bind a Palindromic Sequence Symmetrically to Activate *ADH2* Expression," *Molecular Cellular Biol.*, 11(3);1566–1577 (1991).

Vortkamp et al., "Identification of Optimized Target Sequences for the GL13 Zinc Finger Protein," *DNA Cell Biol.*, 14(7):629–634 (1995).

Wang et al., "Dimerization of Zinc Fingers Mediated by Peptides Evolved In Vitro from Random Sequences," *PNAS*, 96:9568–9573 (1999).

Webster et al., "Conversion of the E1A Cys4 zinc finger to a nonfunctional His2, Cys2 zinc finger by a single point mutation," *PNAS*, 88:9989–9993 (1991).

Whyatt et al., "The two zinc finger–like domains of GATA–1 have different DNA binding specificities," *EMBO J.*, 12(13):4993–5005 (1993).

Wilson et al., "In Vivo Mutational Analysis of the NGFI–A Zinc Fingers*," *J. Biol. Chem.*, 267(6):3718–3724 (92).

Witzgall et al., "The Kruppel–associated box–A (KRAB–A) domain of zinc finger proteins mediates transcriptional repression," *PNAS*, 91:4514–4518 (1994).

Wolfe et al., "Analysis of Zinc Fingers Optimized Via Phage Display: Evaluating the Utility of a Recognition Code," *J. Mol. Biol.*, 285:1917–1934 (1999).

Wolfe et al., "Combining structure–base design with phage display to create new Cys2His2 zinc finger dimers," *Structure*, vol. 8(7):739–750 (2000).

Wolfe et al., "DNA Recognition by Cys2His2 Zinc Finger Proteins," *Annu. Rev. Biophys. Struct.*, 3:183–212 (1999).

Wright et al., "Expression of a Zinc Finger Gene in HTLV–I– and HTLV–II–transformed Cells," *Science*, 248:588–591 (1990).

Wu, H. et al. "Building zinc fingers by selection: Toward a therapeutic application." *PNAS*, 92:344–348 (1995).

Yang et al., "Surface plasmon resonance based kinetic studies of zinc finger–DNA interactions," *J. Immunol. Methods*, 183:175–182 (1995).

Yu et al., "A hairpin ribozyme inhibits expression of diverse strains of human immunodeficiency virus type 1," *PNAS*, 90:6340–6344 (1993).

Zhang et al., "Synthetic–Zinc Finger Transcription Factor Action at an Endogenous Chromosomal Site– Activation of the Human Erythropoietin gene," *J. Biol. Chem.*, 275:33850–33860 (2000).

Bonde et al., "Ontogeny of the v–erb A Oncoprotein from the Thyroid Hormone Receptor: an Alteration in the DNA Binding Domain Plays a Role Crucial for v–erb A Function," *J. Virology*, 65(4):2037–2046 (1991).

Desjardins et al., "Repeated CT Elements Bound by Zinc Finger Proteins Control the Absolute and Relative Activities of the Two Principal Human c–*myc* Promoters," *Mol. and Cellular Biol.*, 13(9):5710–5724 (1993).

Hall et al., "Functional Interaction between the Two Zinc finger Domains of the v–erb A Oncoprotein," *Clee Growth & Differentiation*, 3:207–216 (1992).

Battegay, E.J., "Angiogenesis: mechanistic insights, neovascular diseases, and therapeutic prospects," *J. Mol. Med.*, 73:333–346 (1995).

Crombleholme, T.M., "Adenoviral–mediated gene transfer in wound healing," *Wound Repair and Regeneration*, Nov.–Dec. 2000, pp. 460–472.

Liu et al., "Regulation of an Endogenous Locus Using a Panel of Designed Zinc Finger Proteins Targeted to Accessible Chromatin Regions," *J. Biol. Chem.*, 276(14):11323–11334 (2001).

Liu et al., "Regulation of the endogenous VEGF–A chromosomal locus using designed zinc finger proteins," *Biochemistry and Cell Biology*, 79(3):377 (2001).

Pollock et al., "Regulation of the endogenous VEGF gene by small molecule dimerizers," *Blood*, 98(11):746a, abstract 3108 (2001).

Richard et al., "Angiogenesis: How a Tumor Adapts to Hypoxia," *Biochem. Biophys. Res. Communications*, 266:718–722 (1999).

Yao et al., "Gene therapy in wound repair and regeneration," *Wound Repair and Regeneration*, 8(6):443–451 (2000).

Zhang et al., "Wild–Type p53 Suppresses Angiogenesis in Human Leiomyosarcoma and Synovial Sarcoma by Transcriptional Suppression of Vascular Endothelial Growth Factor Expression," *Cancer Research*, 60:3655–3661 (2001).

* cited by examiner

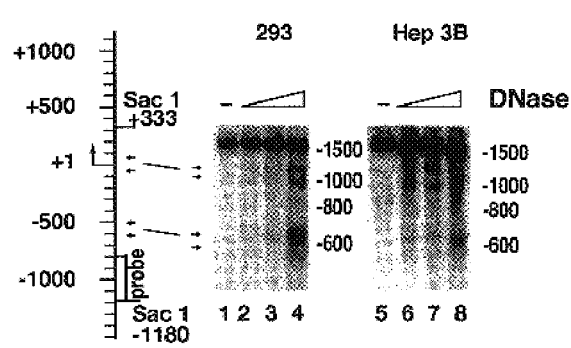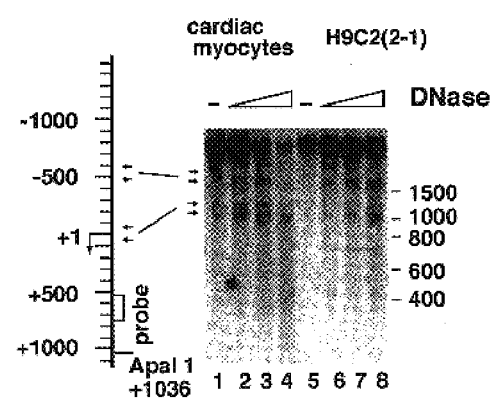
Fig. 1 A                Fig. 1 B

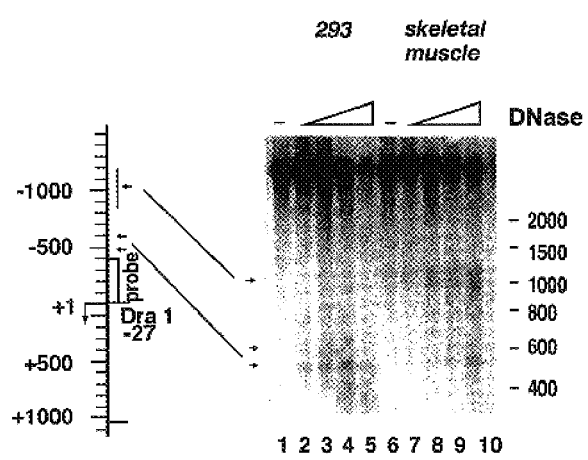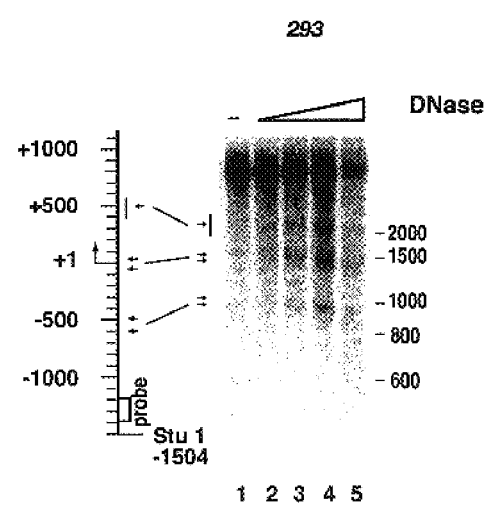
Fig. 1 C
Fig. 1 D

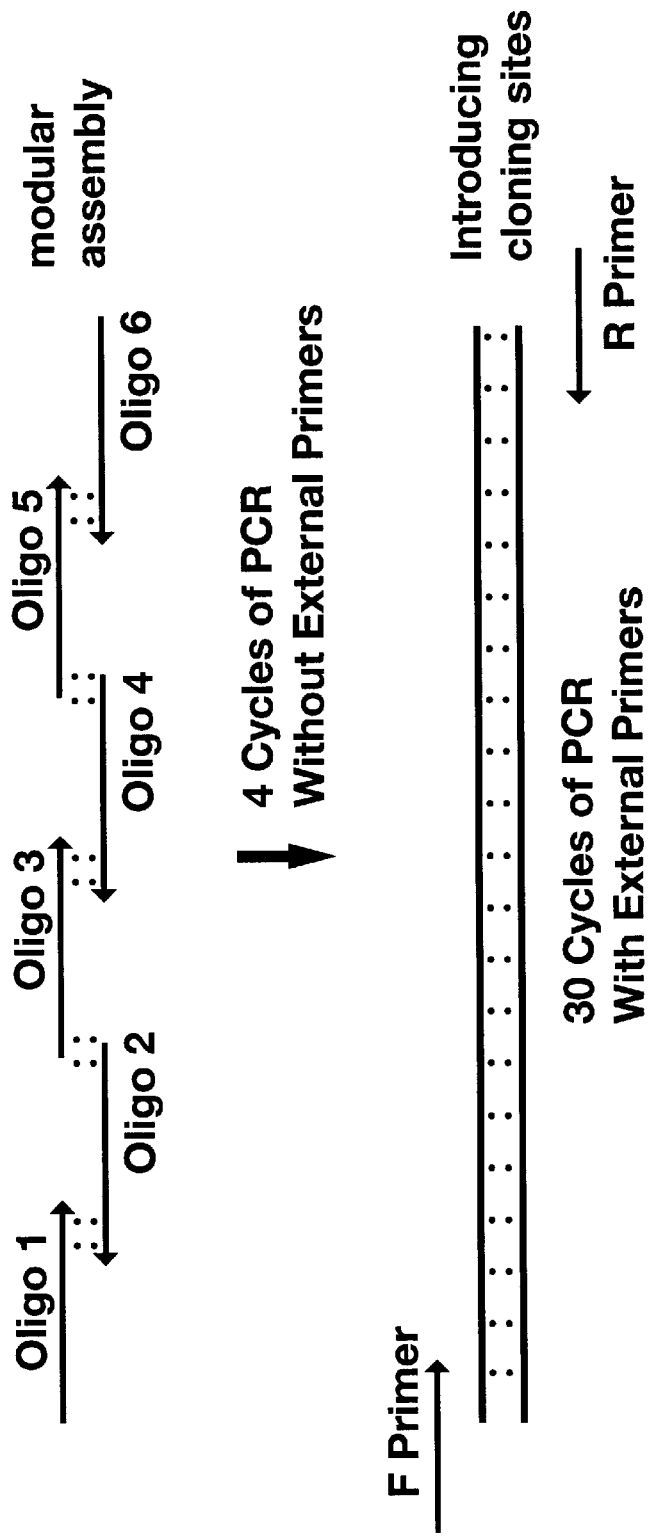

Control    +ZFP

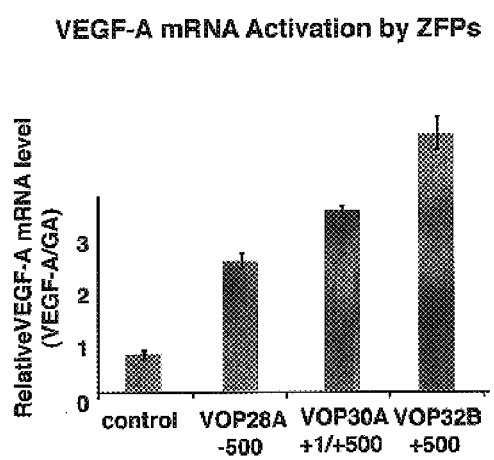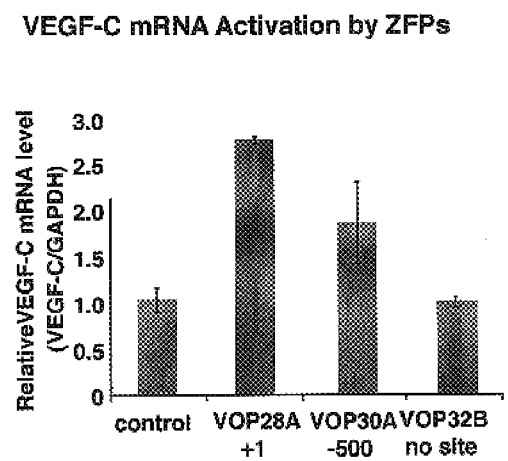
Fig. 14A                                   Fig. 14B

| ZFP Name | Target Sequence 5'- 3' | Target Subsites 5'- 3' | Finger designs -1123456 | |
|---|---|---|---|---|
| mVZ+57 | TGAGCGGCGGCAGCGGAGc | TGAg<br>GCGg<br>GCGg<br>GCAg<br>GCGg<br>GAGc | QSGHLTK<br>RSDELSR<br>RSDELTR<br>QSGSLTR<br>RSDELQR<br>RSDNLAR | F6<br>F5<br>F4<br>F3<br>F2<br>F1 |
| mVZ+426 | GGGGGTGACc | GGGg<br>GGTg<br>GACc | RSDHLSR<br>TSGHLVR<br>DRSNLTR | F3<br>F2<br>F1 |
| mVZ+509 | GCTGGGGGCg | GCTg<br>GGGg<br>GGCg | QSSDLTR<br>RSDHLTR<br>DRSHLTR | F3<br>F2<br>F1 |

Fig. 15C

| ZFP | Target | Gel shift | | Apparent $K_d$ (nM) |
|---|---|---|---|---|
| mVZ+57 | TGAGCGGCGGCAGCGGAGc | | Bound<br>Free | 0.031 |
| mVZ+426 | GGGGGTGACc | | Bound<br>Free | <0.01 |
| mVZ+509 | GCTGGGGGCg | | Bound<br>Free | <0.01 |
| SP1 | GGGGCGGGGg | | Bound<br>Free | 0.053 |

Fig. 15D

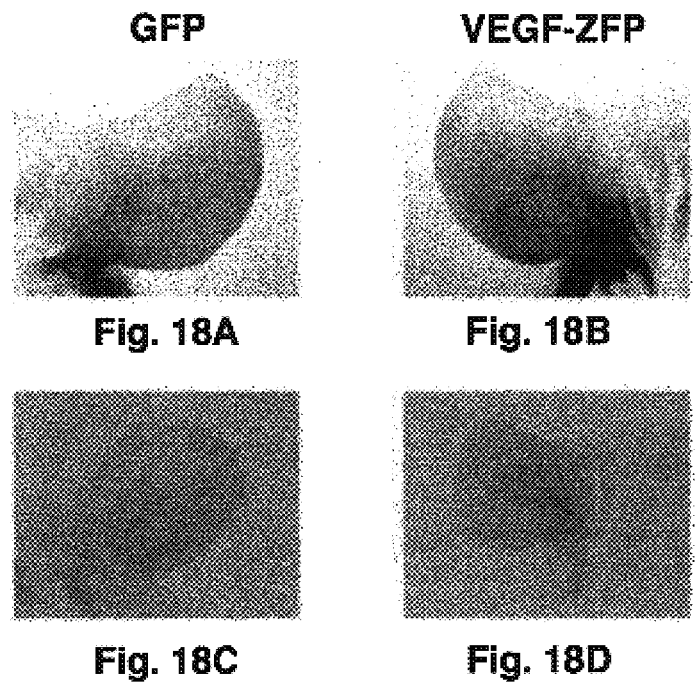
Fig. 18A  Fig. 18B
Fig. 18C  Fig. 18D
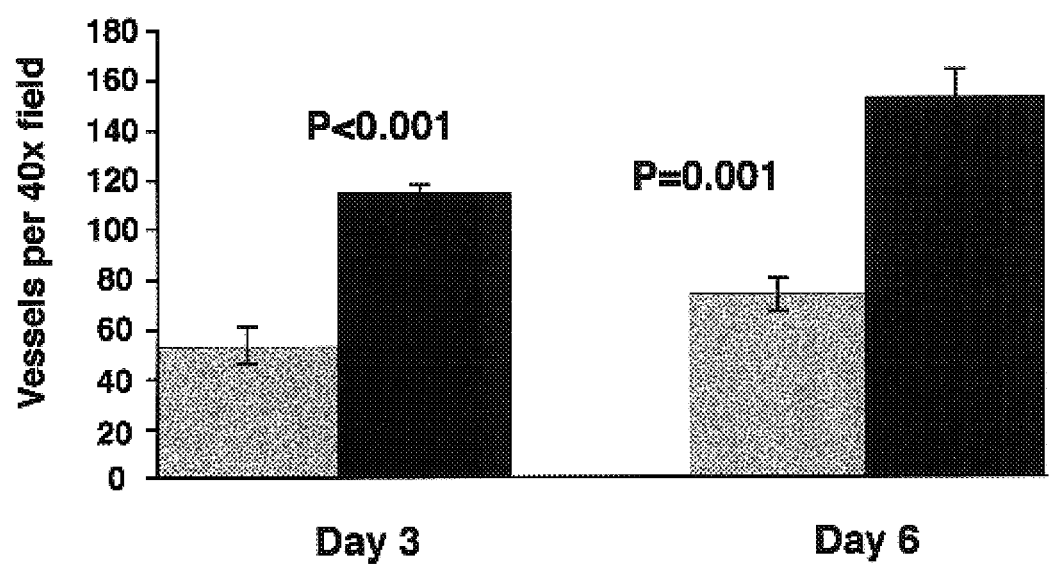
Fig. 18E

GFP

MVG

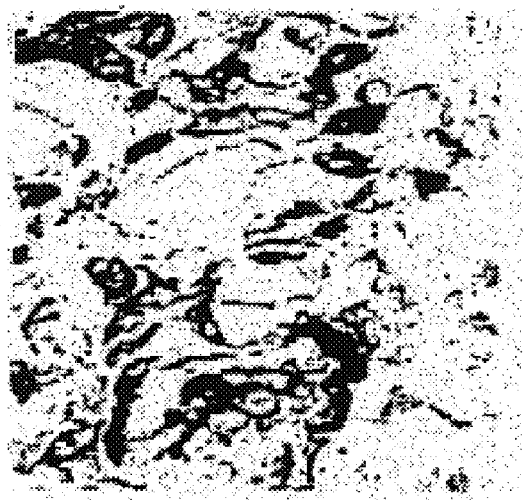 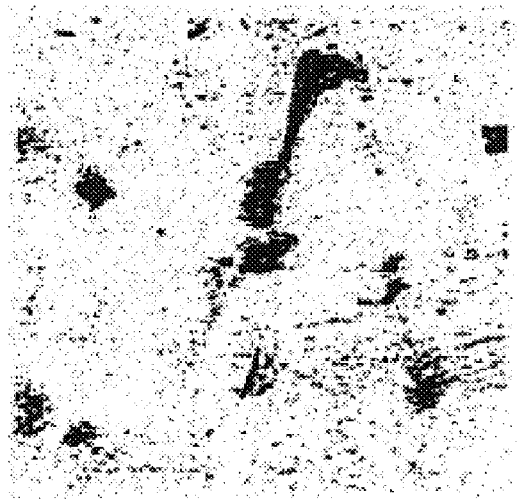
Fig. 21A     Fig. 21B
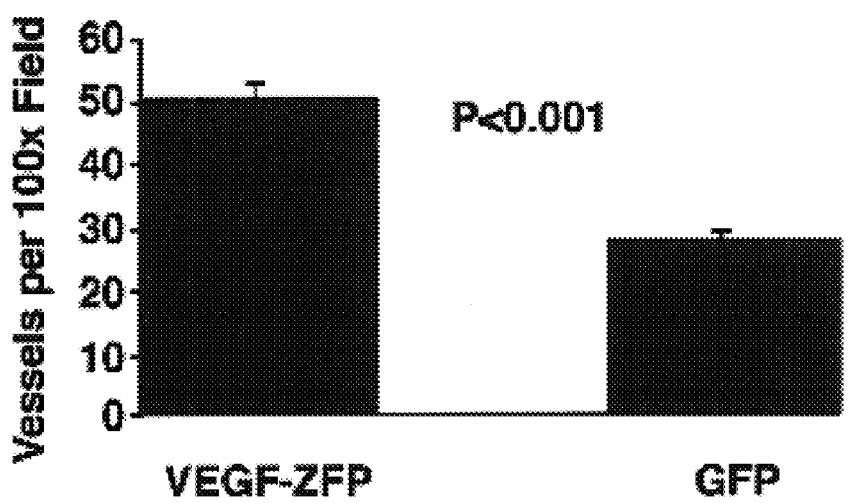
Fig. 21C

REGULATION OF ANGIOGENESIS WITH ZINC FINGER PROTEINS

CROSS-REFERENCES TO RELATED APPLICATIONS

This application is a continuation-in-part of copending U.S. application Ser. No. 09/846,033, filed Apr. 30, 2001, which is a continuation-in-part of U.S. application Ser. No. 09/736,083, filed Dec. 12, 2000 now abandoned, which is a continuation-in-part of U.S. application Ser. No. 09/733,604, filed Dec. 7, 2000 now abandoned, all of which are incorporated herein by reference in their entirety for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

The development of the vascular system (sometimes referred to as the vascular tree) involves two major processes: vasculogenesis and angiogenesis. Vasculogenesis is the process by which the major embryonic blood vessels originally develop from early differentiating endothelial cells such as angioblasts and hematopoietic precursor cells that in turn arise from the mesoderm. Angiogenesis is the term used to refer to the formation of the rest of the vascular system that results from vascular sprouting from the pre-existing vessels formed during vasculogenesis (see, e.g., Risau et al. (1988) Devel. Biol., 125:441–450). Both processes are important in a variety of cellular growth processes including developmental growth, tissue regeneration and tumor growth, as all these processes require blood flow for Given its key role in both normal physiological and pathological processes, not surprisingly considerable research effort has been directed towards identifying factors involved in the stimulation and regulation of angiogenesis. A number of growth factors have been purified and characterized. Such factors include fibroblast growth factors (FGFs), platelet-derived growth factor (PDGF), transforming growth factor alpha (TGFα), and hepatocyte growth factor (HGF) (for reviews of angiogenesis regulators, see, e.g., Klagsbrun et al. (1991) Ann. Rev. Physiol., 53:217–39; and Folkman et al. (1992) J. Biol. Chem., 267:10931–934), the delivery of necessary nutrients.

Thus, angiogenesis plays a critical role in a wide variety of fundamental physiological processes in the normal individual including embryogenesis, somatic growth, and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, such as in the healing of wounds and fractures. Thus, promotion of angiogenesis can be useful in situations in which establishment or extension of vascularization is desirable. Angiogenesis, however, is also a critical factor in a number of pathological processes, perhaps must notably tumor growth and metastasis, as tumors require continuous stimulation of new capillary blood vessels in order to grow. Other pathological processes affected by angiogenesis include conditions associated with blood vessel proliferation, especially in the capillaries, such as diabetic retinopathy, arthropathies, psoriasis and rheumatoid arthritis.

Current research indicates that a family of endothelial cell-specific growth factors, the vascular endothelial growth factors (VEGFs), together with their cognate receptors, are primarily responsible for stimulation of endothelial cell growth and differentiation. These factors are members of the PDGF family and appear to act primarily via endothelial receptor tyrosine kinases (RTKs).

The first identified and most well studied member of this particular family is the vascular endothelial growth factor (VEGF), also referred to as VEGF-A. This particular growth factor is a dimeric glycoprotein in which the two 23 kD subunits are joined via a disulfide bond. Five VEGF-A isoforms encoded by distinct mRNA splice variants appear to be equally effective in stimulating mitogenesis in endothelial cells, but tend to have differing affinities for cell surface proteoglycans.

VEGF-A acts to regulate the generation of new blood vessels during embryonic vasculogenesis and then subsequently plays an important role in regulating angiogenesis later in life. Studies showing that inactivation of a single VEGF-A allele results in embryonic lethality provide evidence as to the significant role this protein has in vascular development and angiogenesis (see, e.g., Carmeliet et al. (1996) Nature 380: 435–439; and Ferrara et al. (1996) Nature, 380: 439–442). VEGF-A has also been shown to have other activities including a strong chemoattractant activity towards monocytes, the ability to induce the plasminogen activator and the plasminogen activator inhibitor in endothelial cells, and to induce microvascular permeability. VEGF-A is sometimes also referred to as vascular permeability factor (VPF) in view of this latter activity. The isolation and properties of VEGF-A have been reviewed (see, e.g., Ferrara et al. (1991) J. Cellular Biochem. 47: 211–218; and Connolly, J. (1991) J. Cellular Biochem. 47:219–223).

Alternative mRNA splicing of a single VEGF-A gene gives rise to at least five isoforms of VEGF-A. These isoforms are referred to as VEGF-A121; VEGF-A145; VEGF-A165; VEGF-A189; and VEGF-A206. As the name implies, the VEGF-A165 isoform is a 165 amino acid species and has a molecular weight of approximately 46 kD; this isoform is the predominant molecular form found in normal cells and tissues. VEGF-A165 includes a 44 amino acid region near the carboxyl-terminal region that is enriched in basic amino acid residues. It also exhibits an affinity for heparin and heparin sulfates.

VEGF-A121 is the shortest form, with a deletion of 44 amino acids between positions 116 and 159 as compared to the VEGF A165 isoform. It is freely diffusible in the surrounding extracellular matrix. VEGF-A189 is a longer form with an insertion of 24 highly basic residues at position 116 with respect to VEGF A165. The VEGF-A206 isoform includes insertion of 41 amino acids with respect to the VEGF A165 isoform, including the 24 amino acid insertion found in VEGF-A189. VEGF-A121 and VEGF-A165 are soluble proteins, with VEGF-A165 being the predominant isoform secreted by cells. In contrast, VEGF-A189 and VEGF-A206 appear to be mostly cell-associated. All of these isoforms of VEGF-A are biologically active.

VEGF-B, also referred to as VRF, has similar angiogenic and other properties to those of VEGF-A, but is distributed and expressed in tissues differently from VEGF-A. In particular, VEGF-B is very strongly expressed in heart, and only weakly in lung, whereas the reverse is the case for VEGF-A. This suggests that VEGF-A and VEGF-B, despite the fact that they are co-expressed in many tissues, may have functional differences. The amino acid sequence of VEGF-B is approximately 44% identical to that of VEGF-A. Alternative exon splicing of the VEGF-B gene generates two isoforms encoding human proteins of 167 and 186 amino acids, and referred to as VEGF-B167 and VEGF-B186, respectively. VEGF-B167 tends to remain cell-associated, while VEGF-B186 is freely secreted. The isolation and characteristics of these isoforms are discussed in PCT/US96/02957 and in Olofsson et al. (1996) Proc. Natl. Acad. Sci. USA 93: 2576–2581.

VEGF-C is also referred to as VEGF-related protein (hence VRP) or VEGF-2. The protein is roughly 30% identical to the amino acid sequence of VEGF-A, and includes N-terminal and C-terminal extensions not present in VEGF-A, VEGF-B or P1GF (infra). Although the protein induces vascular permeability and promotes endothelial growth, it is less potent than VEGF-A. Its isolation and characteristics are disclosed in Joukov et al. (1996) EMBO J. 15: 290–298.

VEGF-D was isolated from a human breast cDNA library, commercially available from Clontech, by screening with an expressed sequence tag obtained from a human cDNA library designated "Soares Breast 3NbHBst" as a hybridization probe (Achen et al. (1998) Proc. Natl. Acad. Sci. USA 95:549–553). The protein is also referred to as FIGF, for c-fos-induced growth factor. The VEGF-D gene is expressed most abundantly in lung, heart, small intestine and fetal lung. It is found at lower levels in skeletal muscle, colon and pancreas. Its isolation and characteristics are discussed in PCT Publication WO 98/07832.

Recently several additional VEGF-like proteins have been identified from various strains of orf viruses; in the literature these viral VEGF proteins have sometimes been collectively referred to as VEGF-E. One protein, variously referred to as OV NZ2, ORFV2-VEGF, OV-VEGF2, and VEGF-ENZ2 has been isolated from the orf viral strain NZ2 (see, e.g., Lyttle, D. J. et al. (1994) J. Virology 68:84–92; and PCT Publication WO 00/25805). Another viral VEGF-like protein referred to as NZ7, OV-VEGF7, VEGF-E and VEGF-ENZ7 has been found in the NZ7 strain of orf viruses. This protein exhibits potent mitogenic activity but lacks the basic domain of certain VEGF proteins such as VEGF-A165 (see, e.g., Lyttle, D. J. et al. (1994) J. Virology 68:84–92; and Ogawa, S. et al. (1998) J. Biol. Chem. 273:31273–31282). A third VEGF-like protein has been identified in a NZ strain, specifically a NZ10 strain and is referred to simply as NZ10 (see, e.g., PCT Publication WO 00/25805). Yet another VEGF-like protein has been identified in the orf virus strain D1701 and in some instances has been referred to as VEGF-ED1701 (see, e.g., Meyer, M. et al. (1999) EMBO J. 18:363–74).

In addition to these viral VEGF-E genes, a VEGF-like growth factor isolated from mammalian sources has also been named VEGF-E. The isolation and characterization of this VEGF-like factor is discussed in PCT Publication WO 99/47677.

Another VEGF-like protein has been termed PDGF/VEGF-Like Growth Factor H, or simply VEGF-H. It is discussed in PCT Publication WO 00/44903. Additional VEGF-like proteins include one called VEGF-R (see, e.g., PCT Publication WO 99/37671) and another referred to as VEGF-X (see, e.g., PCT publication WO 00/37641). Most recently a VEGF protein referred to as VEGF-138 has been identified by Neufeld and others. A final protein related to the VEGF proteins is the Placenta Growth Factor, P1GF. This protein was isolated from a term placenta cDNA library. A segment of the protein exhibits high levels of homology with VEGF-A. Its isolation and characteristics are described by Maglione et al. (1991) Proc. Natl. Acad. Sci. USA 88:9267–9271. Its biological function is presently not well understood. Two alternatively transcribed mRNAs have been identified in humans (P1GF-1 and P1GF-2).

The foregoing PDGF/VEGF family members act primarily by binding to receptor tyrosine kinases. Five endothelial cell-specific receptor tyrosine kinases have been identified thus far, namely VEGFR-1 (also called Flt-1), VEGFR-2 (also called KDR/Flk-1), VEGFR-3 (Flt4), Tie and Tek/Tie-2. Each of these kinases have the tyrosine kinase activity necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

VEGF-A binds VEGFR-1 and VEGFR-2 with high affinity, as well as neurophilin 1. As just indicated, VEGFR-1 binds VEGF-A, but also binds VEGF-B and P1GF. VEGF-C has been shown to be the ligand for VEGFR-3, and it also activates VEGFR-2 (Joukov et al. (1996) The EMBO Journal 15: 290–298). Both VEGFR-2 and VEGFR-3 bind VEGF-D. Initial studies with the viral VEGF proteins (i.e., the viral VEGF-E group) show that these proteins selectively bind VEGFR-2 but not VEGFR-1 (see, e.g., Ogawa, S. et al. (1998) J. Biol. Chem. 273:31273–31282; and Meyer, M. et al. (1999) 18:363–74). A ligand for Tek/Tie-2 has been described in PCT Publication WO 96/11269. The ligand for Tie has not yet been identified. Additional details regarding the various VEGF receptors are provided in PCT Publication WO 00/25805.

Recently, a 130–135 kDa VEGF isoform specific receptor has been purified and cloned (Soker et al. (1998) Cell 92:735–745). The evidence indicates that this VEGF receptor specifically binds to the VEGF165 isoform via the exon 7 encoded sequence of VEGF165, which sequence shows weak affinity for heparin (Soker et al.(1998) Cell, 92:735–745). The receptor has also been found to be identical to human neurophilin-1 (NP-1), a receptor involved in early stage neuromorphogenesis. One of the splice variants of P1GF, namely P1GF-2, also appears to interact with NP-1 (Migdal et al., (1998) J. Biol. Chem. 273: 22272–22278).

Thus, a variety of cell growth factors, in particular VEGF proteins and VEGF-related proteins, have been identified. Certain receptors that bind to the VEGF proteins have also been identified. However, modulation of the expression of VEGF proteins and VEGF-related proteins so as to modulate the process of angiogenesis has not been described. The ability to modulate the process of angiogenesis in a cell or group of cells, using one or more exogenous molecules, would have utility in activating beneficial aspects associated with endothelial cell growth and in repressing non-beneficial aspects.

SUMMARY

A variety of zinc finger proteins (ZFPs) and methods utilizing such proteins are provided for use in regulating gene expression. Certain of the ZFPs are designed to bind to specific target sequences within genes and thereby modulate angiogenesis. The ZFPs can be fused to a regulatory domain as part of a fusion protein. By selecting either an activation domain or repressor domain for fusion with the ZFP, one can either activate or repress gene expression. Thus, by appropriate choice of the regulatory domain fused to the ZFP, one can selectively modulate the expression of a gene and hence various physiological processes correlated with such genes. Thus, with angiogenesis, for example, by attaching an activation domain to a ZFP that binds to a target sequence within a gene that affects angiogenesis, one can enhance certain beneficial aspects associated with angiogenesis (e.g., alleviation of ischemia). In contrast, if angiogenesis is associated with harmful processes (e.g., delivery of blood supply to tumors) one can reduce angiogenesis by using ZFPs that are fused to a repressor. Hence, binding of this type of ZFP to a gene involved in angiogenesis can significantly reduce angiogenesis.

The ZFPs provided include one or more zinc fingers with at least one finger having an amino acid sequence as shown in a row of Table 3 or 4. These ZFPs include those that bind to specific sequences within various VEGF genes. Such binding can be utilized to regulate angiogenesis and treat ischemia and various other disorders dependent upon proper blood flow. Tables 3 and 4 show the amino acid sequences of a large collection of ZFPs that bind to particular target sites within different VEGF genes. The nucleotide target site is shown in column 2 of these tables. Thus, certain ZFPs disclosed herein recognize a target site that has a nucleotide sequence as specified in Tables 3 and 4. Some of these ZFPs include 1–6 fingers (although other ZFPs can have more fingers) and these fingers are occupied by the amino acids shown in a row of Table 3 or 4. These amino acids can occupy positions −1 to +6 of a zinc finger.

Certain of the ZFPs provided herein recognize a target site that typically has 9 nucleotides. In general, such target sites include three target subsites bound by respective zinc finger components of a multifinger protein. Examples of such target sites are listed in Table 3. The amino acid sequences of portions of the zinc finger components involved in recognition are shown in columns 4, 6 and 8. For some proteins that have three zinc fingers, the fingers are occupied by first, second and third segments of seven contiguous amino acids as shown in Table 3.

Other ZFPs that are disclosed herein bind target sequences that typically include 18 nucleotides. These target sequences can be recognized by ZFPs that include six fingers. Examples of such ZFPs are listed in Table 4. Hence, certain of the present ZFPs include the six finger ZFPs shown in Table 4, with positions −1 to +6 in each of the fingers being occupied by a segment of seven contiguous amino acids as specified in a row of Table 4.

As indicated above, some of the ZFPs provided herein are useful in methods for modulating angiogenesis. In some methods, the modulation of angiogenesis comprises inhibition of new blood vessel formation. In some methods, the modulation of angiogenesis comprises stimulation of new blood vessel formation. In some such methods the blood vessels are nonpermeable or nonhyperpermeable.

Thus, also provided are ZFPs that bind to a target site having a nucleotide sequence as specified in Table 3 or 4, thereby modulating angiogenesis when introduced into an animal having a genome comprising a VEGF gene comprising the target site. Often any of the foregoing types of ZFPs are part of a fusion protein that includes a regulatory domain. This regulatory domain can be an activator or a repressor.

In like manner, certain of the methods for modulating angiogenesis as provided herein involve introducing a ZFP that binds to a target site specified in Table 3 or 4 into an animal having a genome comprising a VEGF gene that includes the target site, with binding of the ZFP to the target site resulting in modulation of angiogenesis in the animal. Related methods involve contacting a target site of a nucleic acid within a cell with a zinc finger protein, wherein the target site has a nucleotide sequence as specified in Table 3 or 4 and binding of the zinc finger protein to the target site modulates expression of the VEGF gene in the cell.

The ZFPs provided herein can be used to treat a number of different diseases that are correlated with regulating the formation of blood vessels. Thus, certain methods are designed to treat ischemia. Some of these methods involve administering a ZFP that binds to a target site as specified in Table 3 or 4 into an animal having ischemia, wherein the ZFP is administered in an amount effective to treat ischemia. The ZFPs can also be utilized, for example, in wound treatment, a variety of surgical applications and in promoting the growth of lymphatic endothelial cells and the activation of myelopoiesis. Other ZFPs find use in preventing unwanted processes by repressing vessel formation. Thus, for example, ZFPs can be used in treating diabetic retinopathy, psoriasis, arthropathies and tumor growth.

By selecting certain ZFPs one can tailor the extent to which a physiological process (e.g., angiogenesis) can be modulated and tailor treatment. This can be achieved because multiple target sites in any given gene can be acted upon by the ZFPs provided herein and because a single ZFP can bind to a target site located in a plurality of genes. Thus, in some methods, a plurality of ZFPs are administered. These ZFPs can then bind to different target sites located within the same gene. Such ZFPs can in some instances have a synergistic effect. In certain methods, the plurality of fusion proteins include different regulatory sequences. In contrast, with some of the ZFPs provided herein, administration of a single ZFP can modulate gene expression of multiple genes because each gene includes the target site.

Also provided herein are nucleotides that encode the ZFPs disclosed herein. Additionally, pharmaceutical compositions containing the nucleic acids and/or ZFPs are also provided. For example, certain compositions include a nucleic acid that encodes one of the ZFPs described herein operably linked to a regulatory sequence and a pharmaceutically acceptable carrier or diluent, wherein the regulatory sequence allows for expression of the nucleic acid in a cell. Protein based compositions include a ZFP as disclosed herein and a pharmaceutically acceptable carrier or diluent.

BRIEF DESCRIPTION OF THE DRAWINGS

FIGS. 1A and 1B show analysis of constitutive accessible sites. Chromatin from the indicated human (FIG. 1A) or rat (FIG. 1B) cells was partially digested with DNAse I in permeabilized nuclei (see "Experimental Procedures"), followed by Southern blot analysis using the indicated restriction enzymes and probes. The vertical bar represents genomic DNA in the VEGF-A promoter region. A hooked arrow denotes the transcription start site, and tick marks indicate units of 100 bp. Positions of restriction enzyme recognition sites are indicated in base pairs relative to the start site of VEGF-A transcription. The migration pattern for a set of DNA standard fragments is indicated at the right side of each gel, with the size of each fragment given in bp.

Arrows are used to highlight the relationship of the observed bands to location of accessible chromatin regions relative to the transcription start sites of VEGF-A. DNAse I concentrations (in Worthington Units/ml) were as follows: HEK 293 nuclei (FIG. 1A, lanes 1–4): 0, 7.5, 15, 60; HEP3B nuclei (FIG. 1A, lanes 5–8): 0, 7.5, 15, 30; cardiac myocyte nuclei (FIG. 1B, lanes 1–4): 0, 3.75, 7.5, 15; H9c2(2-1) nuclei (FIG. 1B, lanes 5–8): 0, 15, 30, 60.

FIG. 1C shows the results of an experiment indicating the presence of an accessible region~1000 base pairs upstream of the VEGF-A transcription start site in primary skeletal muscle cells but not HEK 293 cells. Details as in FIGS. 1A and 1B, except that nuclei were isolated from HEK 293 cells or human primary skeletal muscle cells; DNAse I concentrations (Units/ml) were as follows: HEK 293 nuclei (lanes 1–5): 0, 7.5, 15, 30, 60; primary skeletal muscle cell nuclei (lanes 6–10): 0, 3.75, 7.5, 15, 30.

FIG. 1D shows the results of an experiment indicating the presence of an accessible region 500 bp downstream of the VEGF-A transcription start site in HEK 293 cells. Details as in FIGS. 1A and 1B. DNAse I concentrations (Units/ml) were as follows (lanes 1–5): 0, 15, 30, 60, 120.

FIG. 1E shows a summary of DNAse I accessible regions observed in these studies. Cell types tested are indicated at left. Observation of a particular open region in a given cell type is denoted by a an arrow. The '–550' and '+1' hypersensitive regions occur in all cell types tested, while the '–1000' and '+500' sites appear only in a subset of tested cells. A schematic representation of the VEGF-A promoter, encompassing bases –1000 to +1000 relative to the principal transcription start site, is provided at bottom. The filled arrow denotes the principal site of transcription initiation, while an alternate start site is highlighted by an open arrow. Key regulatory elements are also shown (HRE: hypoxia response element; binding sites for the SP1 and AP2 transcription factors are also shown). DNAse I accessible regions are indicated by gradient-shaded rectangles above the map.

FIG. 1F shows an analysis of the extent of sequence conservation between man, mouse and rat in the promoter region of the VEGF-A gene. Each point in the gray profile indicates the fractional conservation of human VEGF-A sequence in both rat and mouse within a 50 bp window centered on that point. The black profile is identical except that it indicates the fractional conservation of 5 bp blocks.

FIGS. 2A–2D show the scheme for targeting construction of VEGF-A targeted ZFPs.

Figure 2A:
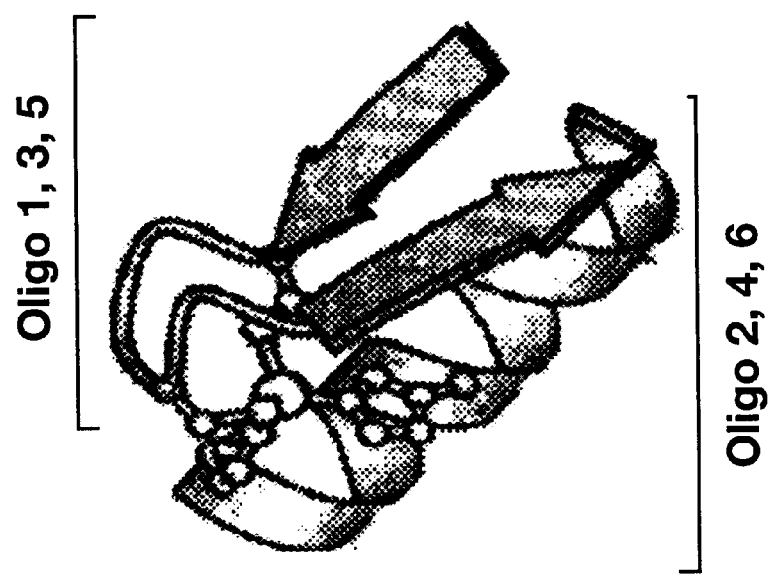

FIG. 2A shows a schematic diagram depicting the structure of an individual zinc finger with two β-sheets linked to the DNA-binding α-helix. The diagram is based on Pavletich et al. (1991) Science 252: 809–817. Oligos 1, 3 and 5 encode the β-sheet regions, and oligos 2, 4, and 6 encode the DNA-binding α-helix regions.

FIG. 2B shows the scheme for assembly of ZFP-encoding nucleic acids. Six overlapping oligonucleotides were annealed, gaps were filled, and the resulting duplex was amplified using a pair of external oligonucleotides. The PCR products were then cut with Kpn I and BamHI, and the digestion product was cloned into the pMalC2 bacterial expression vector.

FIG. 2C shows a schematic diagram of the maltose binding protein-VEGF-A-targeted ZFP fusions.

Figure 2D:
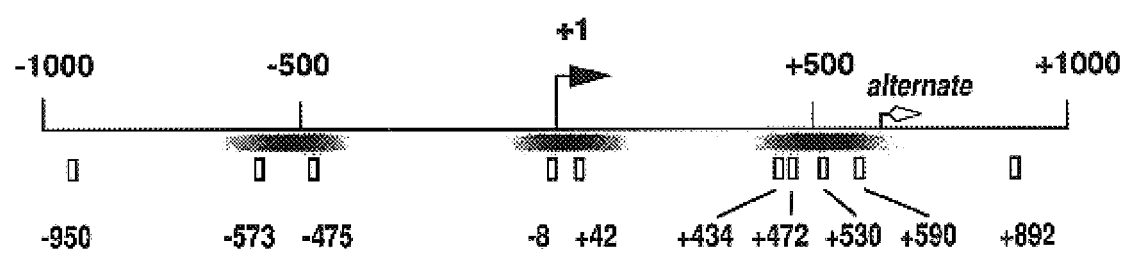

FIG. 2D shows a schematic representation of the human VEGF-A gene, showing the location of transcription initiation sites (hooked arrows), DNAse I-accessible regions in HEK293 cells (gradient-filled rectangles), and target site locations for the VEGF-A-targeted ZFPs (vertical rectangles). The position of the upstream-most nucleotide of each ZFP target site is indicated by the number below it. Numbering is relative to the start site of transcription (+1).

FIGS. 3A–3F show an analysis of the transcriptional activation properties of ZFPs targeted to DNAse I-accessible regions of VEGF-A.

Figure 3A:
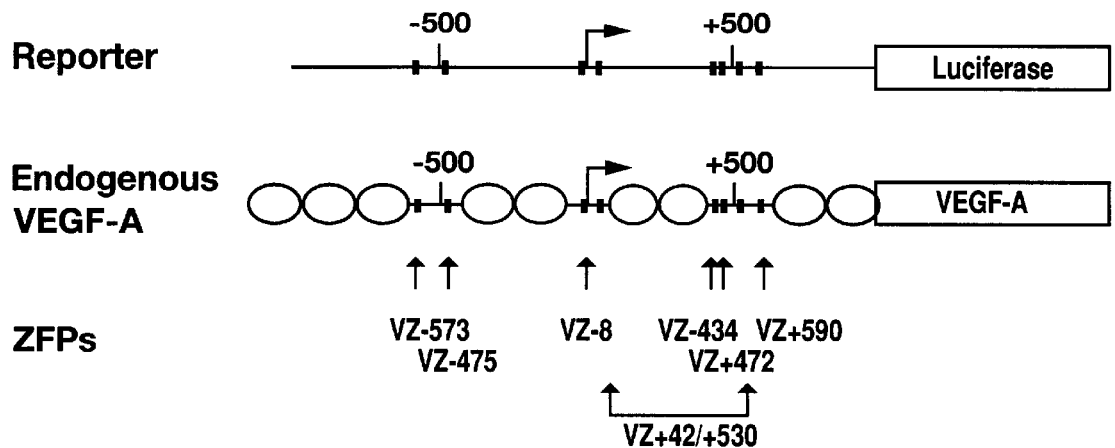

FIG. 3A gives a schematic representation of the VEGF-A promoter reporter construct (top) and the endogenous VEGF-A chromosomal (bottom) targets. Coverage of portions of the endogenous promoter with white circles indicates the presence of nucleosomes in these regions. ZFP targets are indicated by white vertical rectangles, and arrows connect each target with the name of its corresponding ZFP below.

Figure 3B:
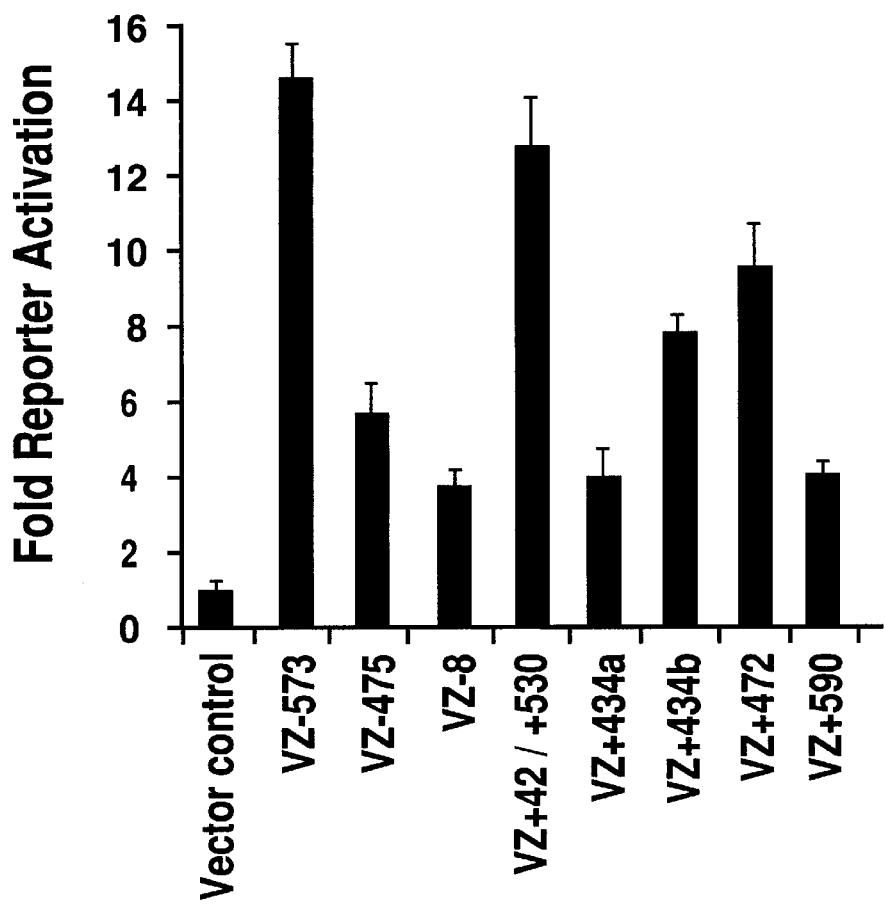

FIG. 3B shows results of assay for activation of the human VEGF-A promoter reporter by ZFP-VP16 fusions. ZFP-VP16 fusion plasmids were co-transfected into HEK293 cells with a VEGF-A reporter construct containing a luciferase gene under the control of a 3.4 kbp fragment of the human VEGF-A promoter, and reporter activity was assayed 40 hours post-transfection as described in "Experimental Procedures." A constitutive Renilla luciferase construct was also co-transfected to serve as transfection control for normalization. The fold reporter activation by the ZFPs was calculated based on the normalized luciferase reporter activity, in comparison with that of the control vector which encodes a VP16-FLAG fusion lacking a ZFP domain.

Figure 3C:
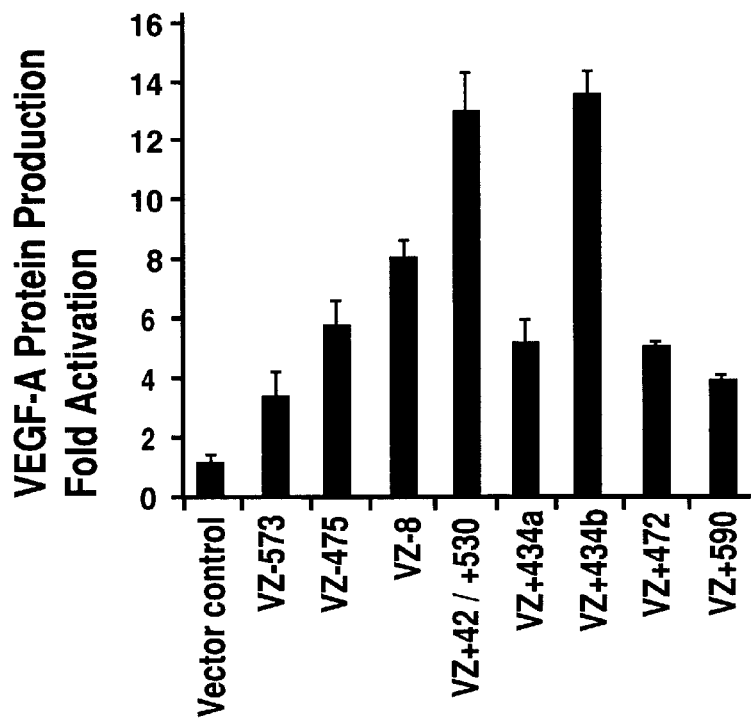
Figure 3D:
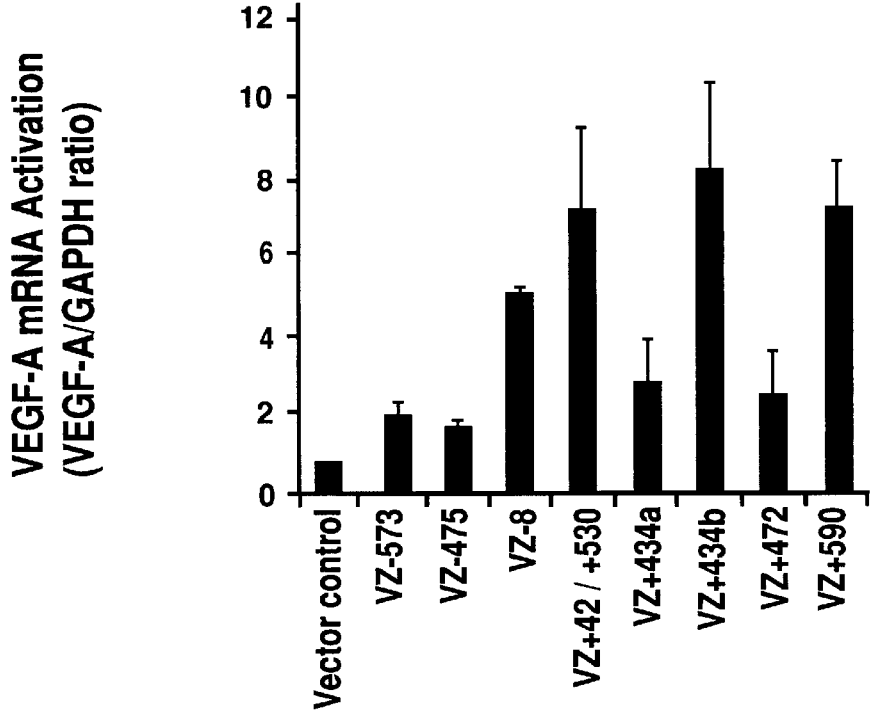

FIGS. 3C and 3D show the results of assays for activation of the endogenous human VEGF-A gene by ZFP-VP16 fusions. Plasmids encoding ZFP-VP16 fusions were transfected into HEK 293 cells via LipofectAMINE reagent as described in "Experimental Procedures." The control vector expressed VP16-FLAG fused with green fluorescent protein (GFP) instead of ZFP. Forty hours after transfection, the culture medium and the cells were harvested and assayed for endogenous VEGF-A expression. FIG. 3C shows the results of measurement of VEGF-A protein content in the culture medium, by ELISA using a human VEGF ELISA kit (R&D Systems, Minneapolis, Minn.). The VEGF-A protein production induced by the ZFPs was compared with that of the control vector, and the fold activation was plotted. FIG. 3D shows results of assays for steady-state VEGF-A mRNA levels in transfected cells, measured by quantitative RT-PCR using Taqman chemistry as described in "Experimental Procedures." The levels of VEGF-A mRNA were normalized with respect to GAPDH (glyceraldehyde-phosphate dehydrogenase) mRNA levels.

Figure 3E:
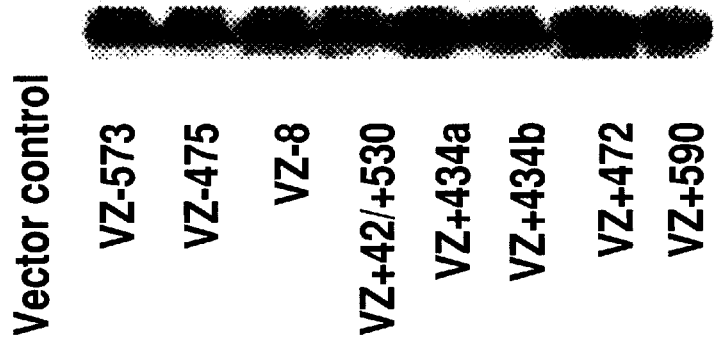

FIG. 3E shows analysis of ZFP protein content in the transfected cells by protein immunoblotting ("Western" blotting) using an anti-FLAG antibody (Sigma, St. Louis, Mo.) which recognizes the FLAG epitope tag of the engineered ZFPs.

Figure 3F:
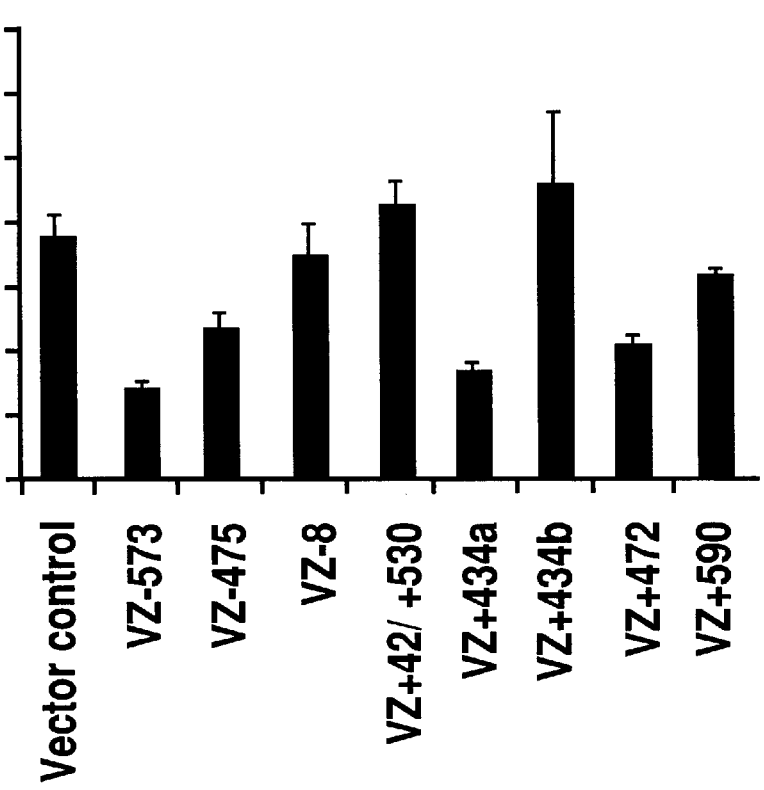

FIG. 3F shows the results of analysis of levels of ZFP mRNA in transfected cells, as determined by Taqman, and normalized to GAPDH mRNA levels. The primers and probe were designed to recognize the sequence encoding the VP16 activation domain and FLAG tag.

Figure 4A:
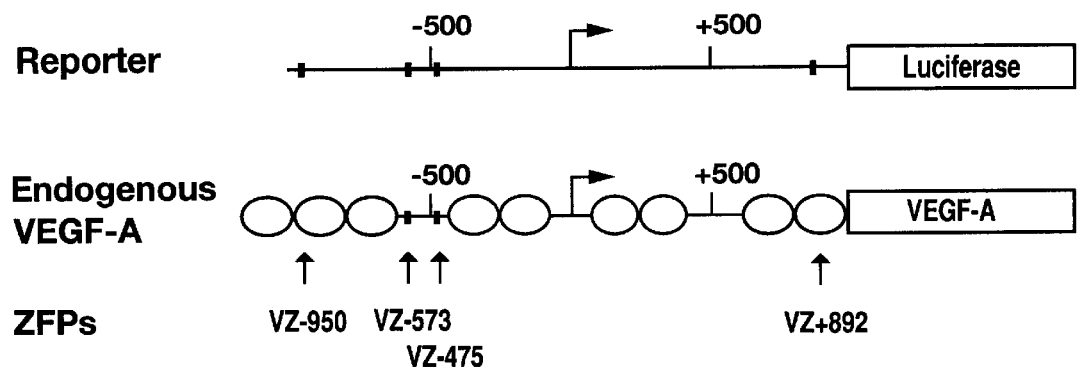
Figure 4B:
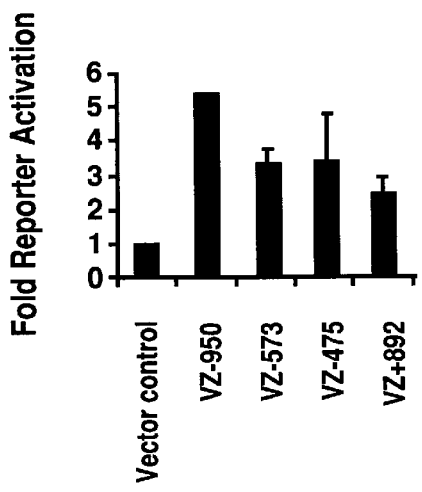
Figure 4C:
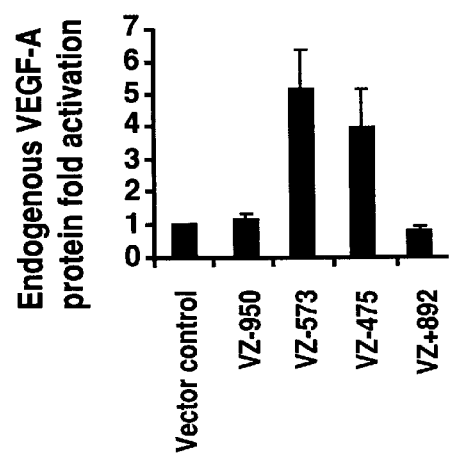

FIGS. 4A–4C show an analysis of the effects of ZFP fusions, targeted to accessible and inaccessible regions of the VEGF-A gene, on a VEGF-A reporter construct and on the endogenous VEGF-A gene.

FIG. 4A provides a schematic representation of the VEGF-A promoter reporter construct (top) and the endogenous VEGF-A chromosomal (bottom) targets used in this experiment. Coverage of portions of the endogenous promoter with white circles indicates the presence of nucleosomes in these regions. ZFP target sites are indicated by white vertical rectangles, and arrows connect each target with the name of its corresponding ZFP below.

FIG. 4B shows activation of a human VEGF-A promoter reporter. The indicated ZFP-VP16 fusion plasmids were co-transfected with the VEGF-A-luciferase reporter construct as described in "Experimental Procedures." The fold-activation of luciferase activity by the ZFPs was calculated in comparison with that of a control vector encoding VP16-FLAG without a ZFP domain.

FIG. 4C shows activation of the endogenous human VEGF-A gene. Plasmids encoding the indicated ZFP-VP16 fusions were transfected into HEK 293 cells, and the amount of VEGF-A protein secreted into the culture medium, 40 hrs after transfection, was measured by ELISA as described in the legend to FIG. 3C. VEGF-A protein production induced by the ZFPs was compared with that of the control vector, and the fold activation was plotted.

FIGS. 5A–5D show activation of the endogenous human VEGF-A gene by ZFPs with different activation domains. Various ZFPs were fused with either a VP16 activation domain or the activation domain from NF-κB (p65). All fusions also contained a C-terminal FLAG epitope tag.

Figures 5A, 5B:
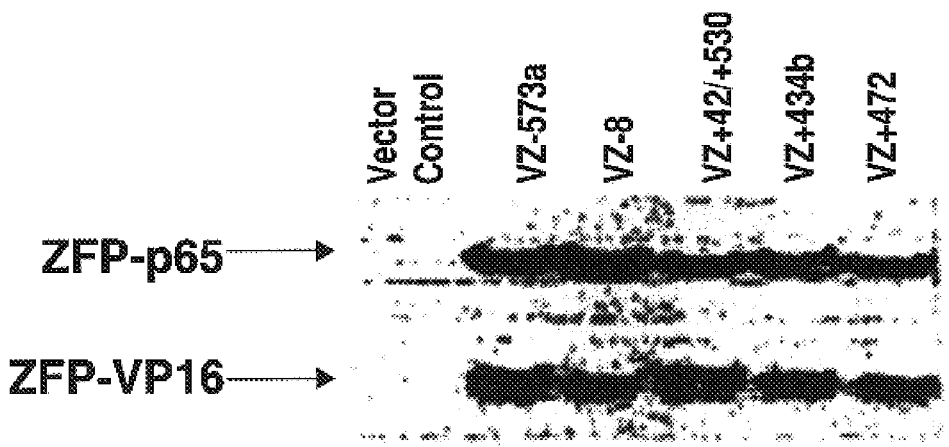

FIG. 5A shows schematic diagrams of VEGF-A targeted ZFP fusions containing either a VP16- or a p65 activation domain (AD). NLS: nuclear localization sequence; ZFP: zinc finger DNA-binding domain; FLAG: Flag epitope tag.

FIG. 5B shows an analysis of ZFP protein content in transfected cells, analyzed by western blotting using anti-FLAG antibody. Identity of the transfected ZFP domain is indicated above each lane of the gel.

Figure 5C:
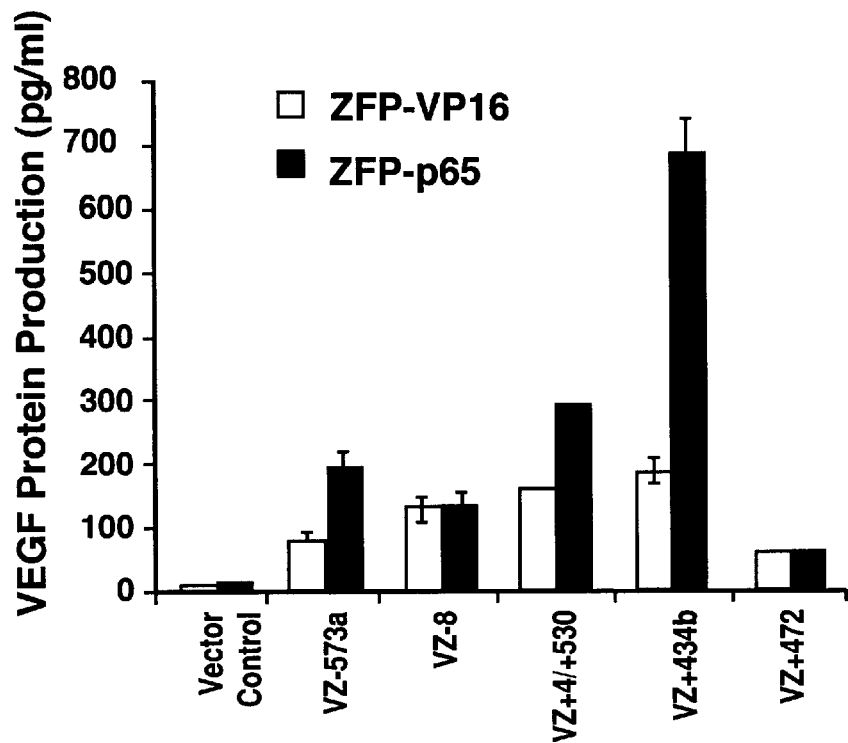

FIG. 5C shows VEGF-A protein content in the culture medium of transfected cells, measured by ELISA. Results from transfection of ZFP fusions comprising a VP16 activation domain are represented by open bars; results from transfection of ZFP fusions comprising a p65 activation domain are represented by filled bars.

Figure 5D:
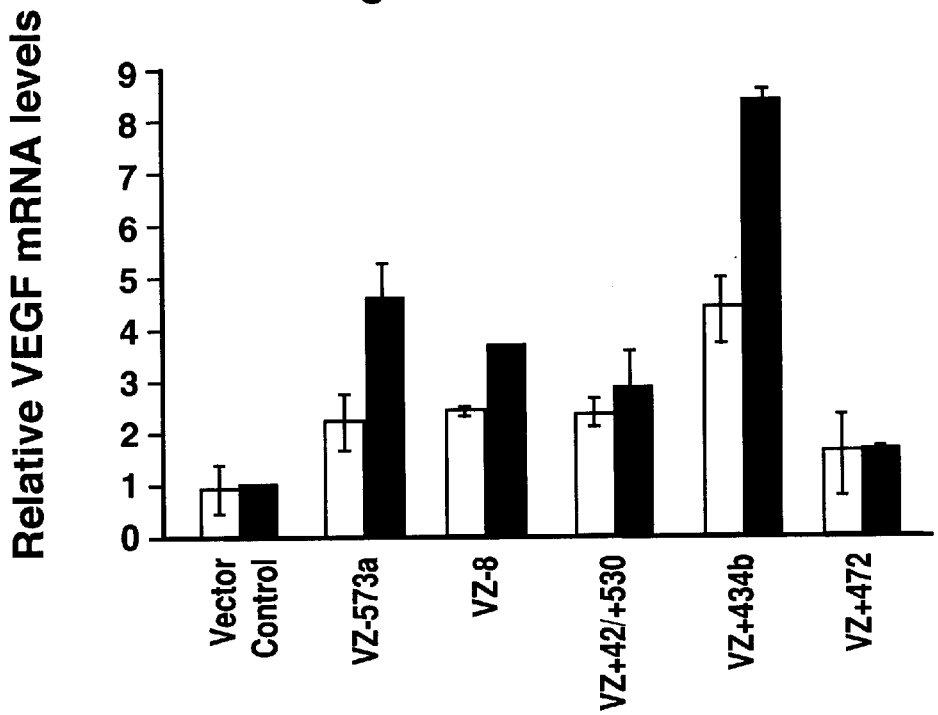

FIG. 5D shows measurement of steady-state VEGF-A mRNA levels in the transfected cells by Taqman. Results from transfection of ZFP fusions comprising a VP16 activation domain are represented by open bars; results from transfection of ZFP fusions comprising a p65 activation domain are represented by filled bars.

FIGS. 6A–6D show an analysis of cooperativity, in VEGF-A gene activation, between ZFPs with different activation domains. Plasmids containing different ZFP-activation domain fusions were cotransfected at a 1:1 ratio into HEK 293 cells, and endogenous VEGF-A activation was measured 40 hours after transfection.

Figure 6A:
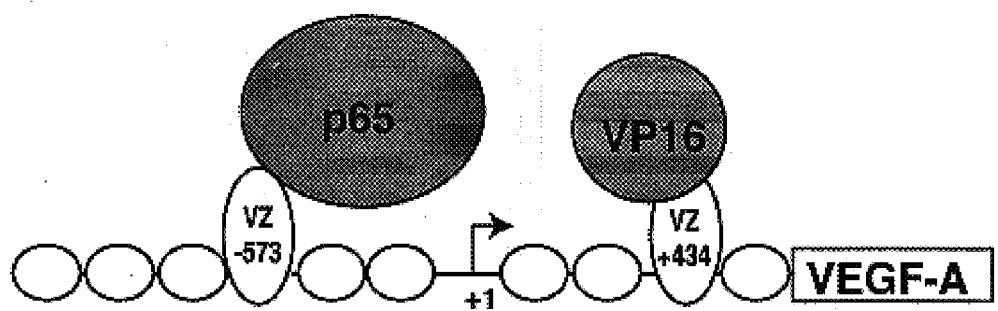

FIG. 6A shows the scheme of the experiment.

Figure 6B:
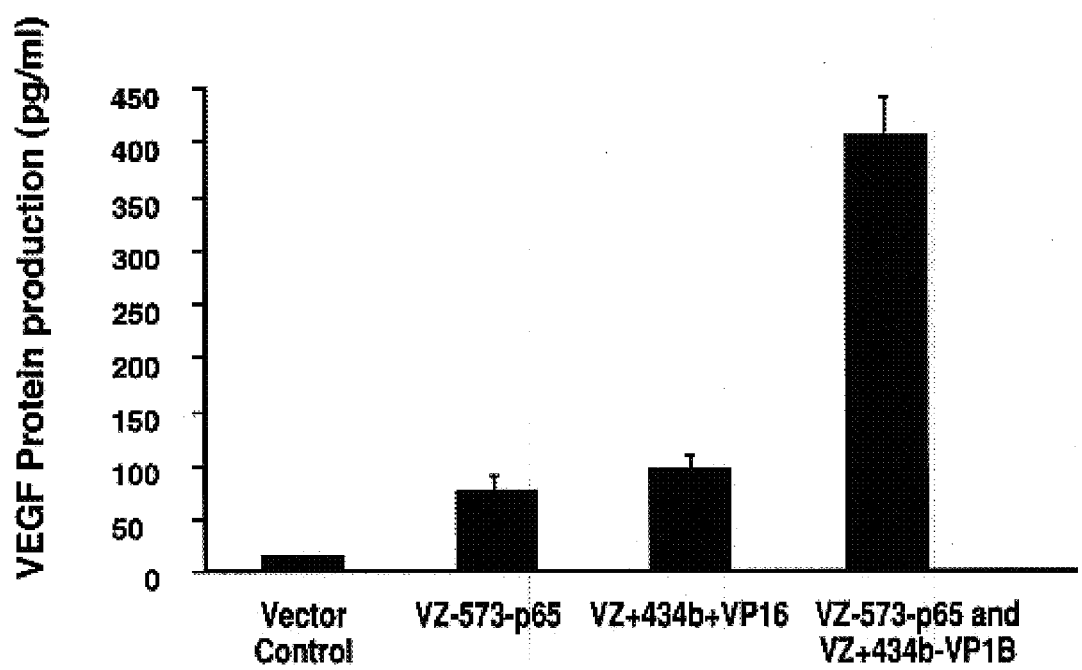

FIG. 6B shows analysis of VEGF-A protein content in the culture medium, assayed by ELISA.

Figure 6C:
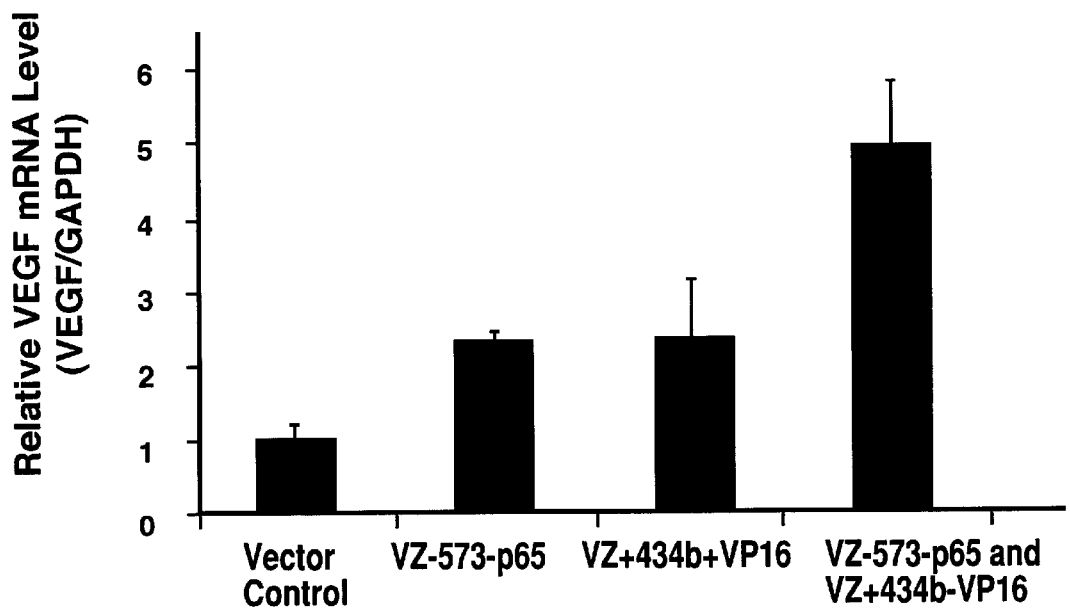

FIG. 6C shows analysis of VEGF-A mRNA levels in transfected cells, measured by Taqman.

Figure 6D:
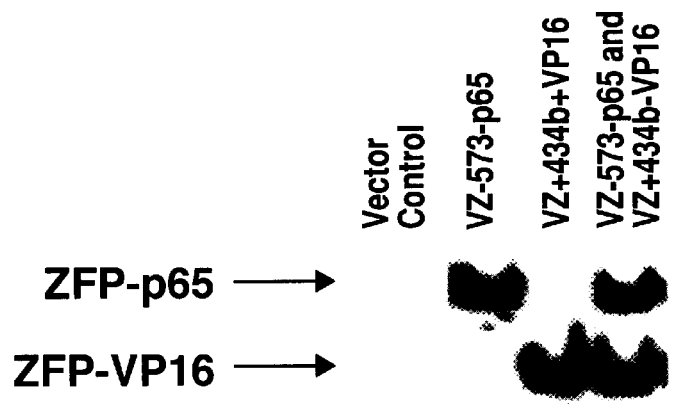

FIG. 6D shows analysis of ZFP protein contents in the transfected cells, by western blotting using anti-FLAG antibody.

FIGS. 7A–7D show a comparison of the activation of the endogenous human VEGF-A gene by ZFP VZ+434b and by hypoxia. HEK 293 cells were transfected with plasmids encoding the ZFP VZ+434b fused with VP16 or p65, transfected with a control vector expressing no ZFP, or exposed to hypoxic conditions (0.5% O2) in a hypoxic incubator for 24 hours. Endogenous VEGF-A gene activation was measured as described in FIG. 6 and "Experimental Procedures."

Figure 7A:
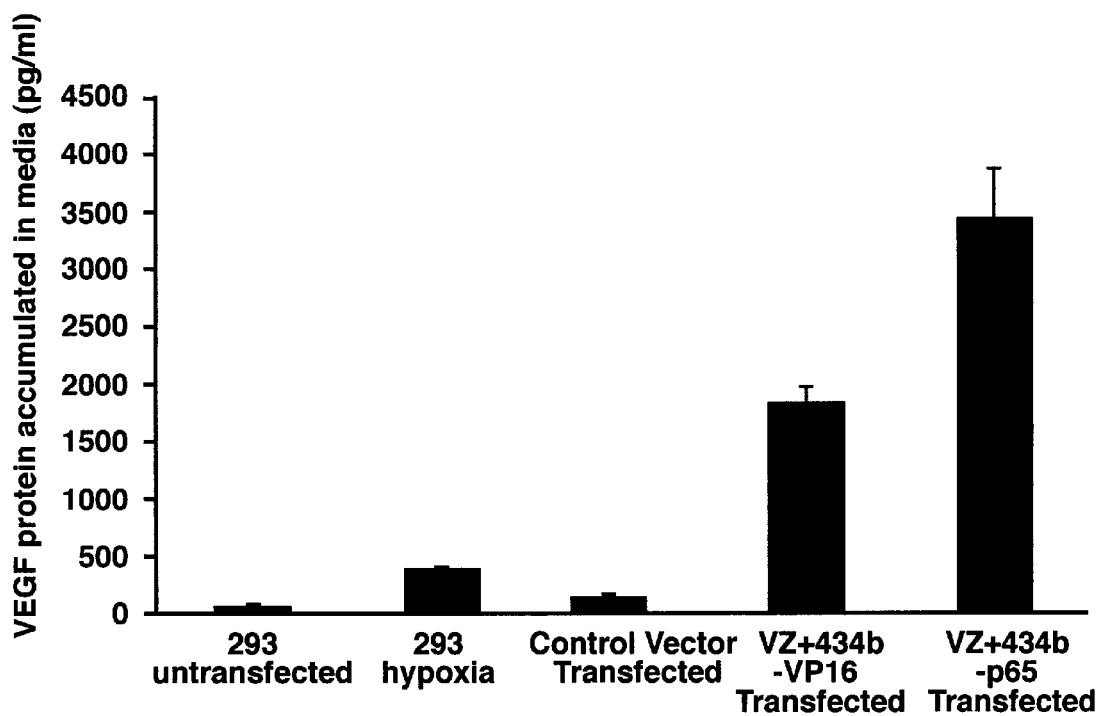

FIG. 7A show analysis of VEGF-A protein content in the culture medium, measured by ELISA.

Figure 7B:
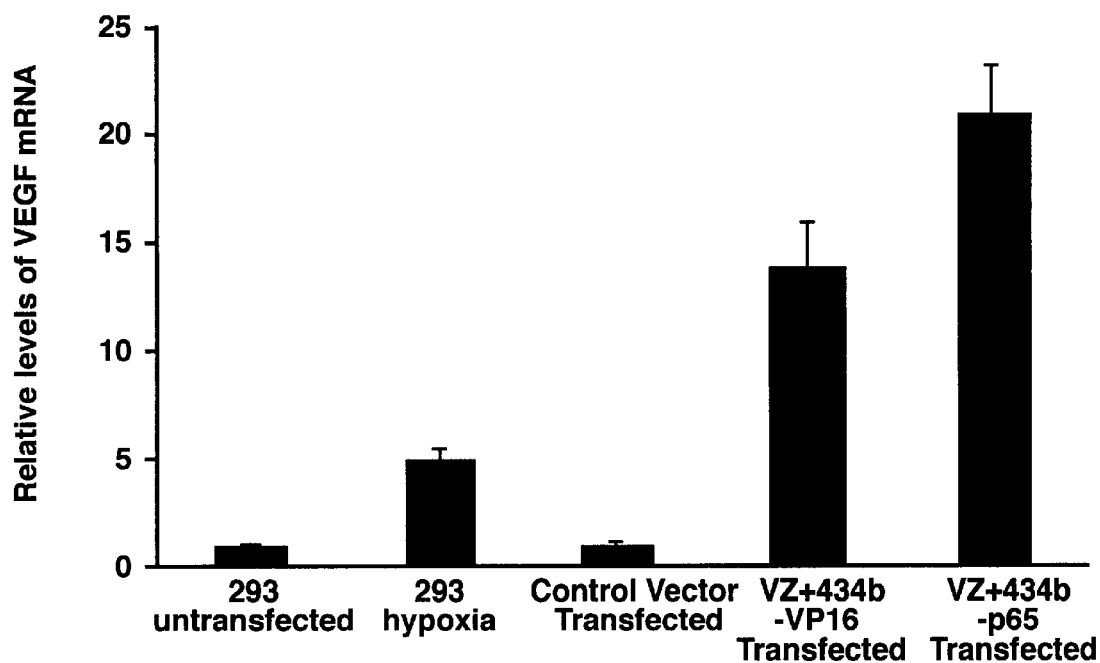

FIG. 7B shows analysis of steady-state VEGF-A mRNA levels, measured by Taqman, and normalized to levels of 18S RNA.

Figure 7C:
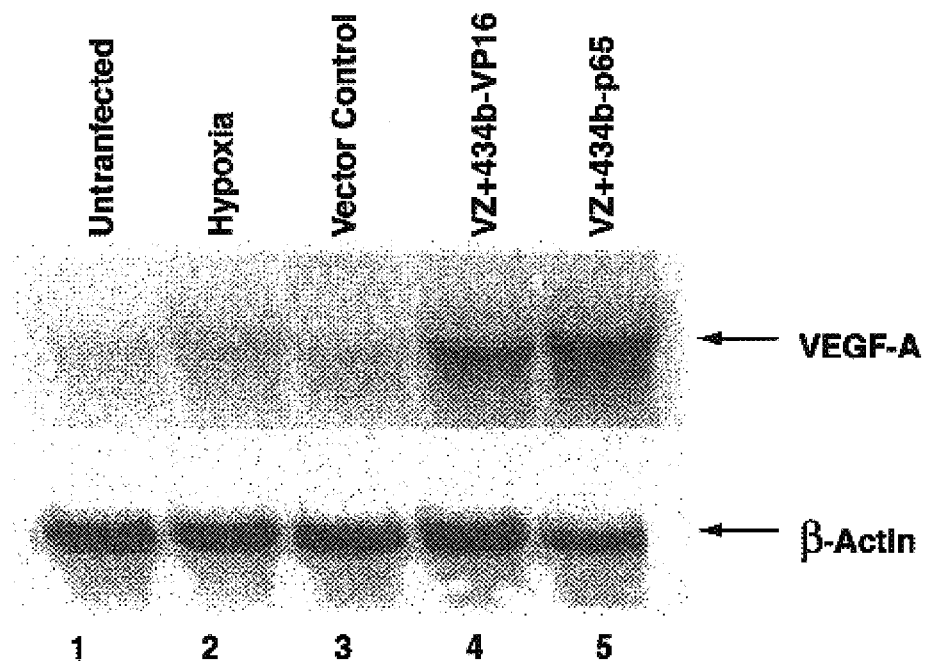

FIG. 7C shows analysis of VEGF-A mRNA by RNA blot ("Northern") hybridization using a 32P-labeled VEGF165 riboprobe.

Figure 7D:
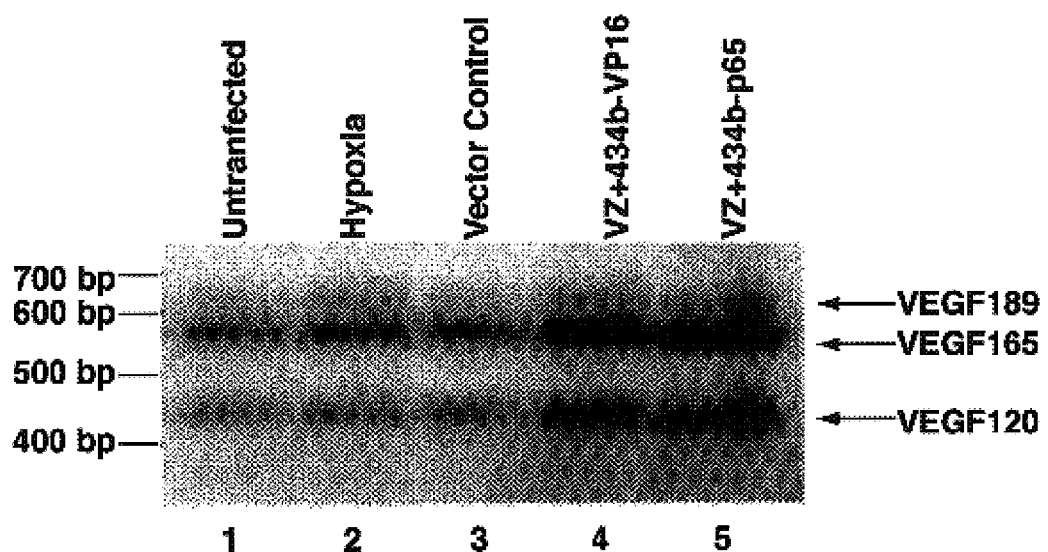

FIG. 7D shows analysis of VEGF-A splice variants by RT-PCR and Southern hybridization as described in "Experimental Procedures."

Figure 8:
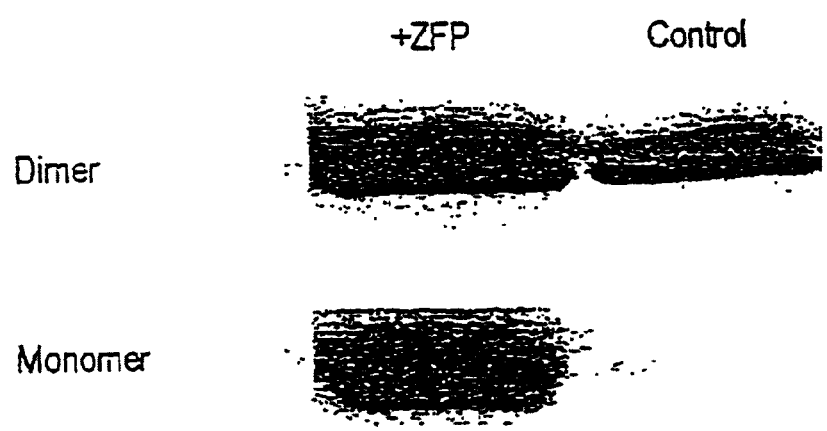

FIG. 8 shows immunoblot analyses of VEGF in ZFP-injected and control-injected mouse quadriceps muscle. Positions of the VEGF monomer and VEGF dimer are indicated.

Figure 9A:
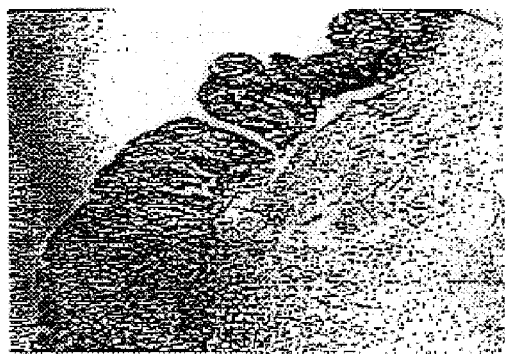
Figure 9B:
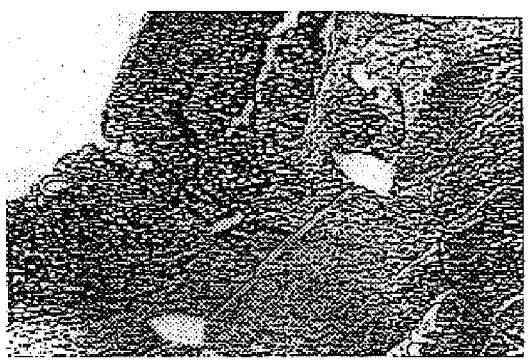
Figure 9C:
Figure 9D:
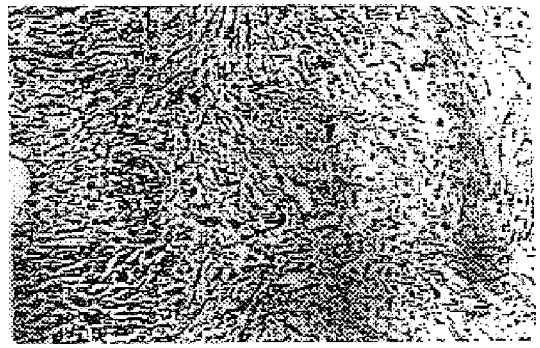
Figure 9E:
Figure 9F:
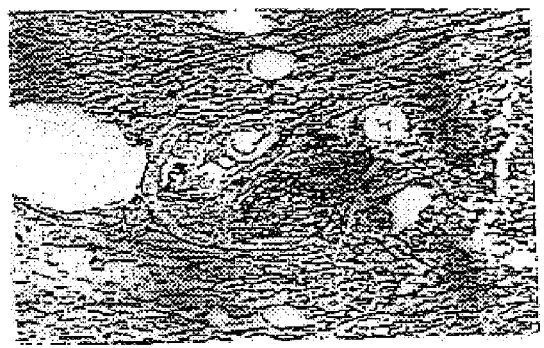

FIGS. 9A–9F show micrographs of H&E-stained thin sections of wound tissue from a mouse that had been injected with a plasmid encoding a ZFP-VP16 fusion. FIGS. 9A and 9B are low-power magnification; FIGS. 9C–9F are high-power. FIGS. 9A, 9C and 9E show sections of wound tissue that was injected with a control plasmid. FIGS. 9B, 9D and 9F show sections of wound tissue that was injected with a plasmid encoding a ZFP-VP16 fusion.

Figure 10:
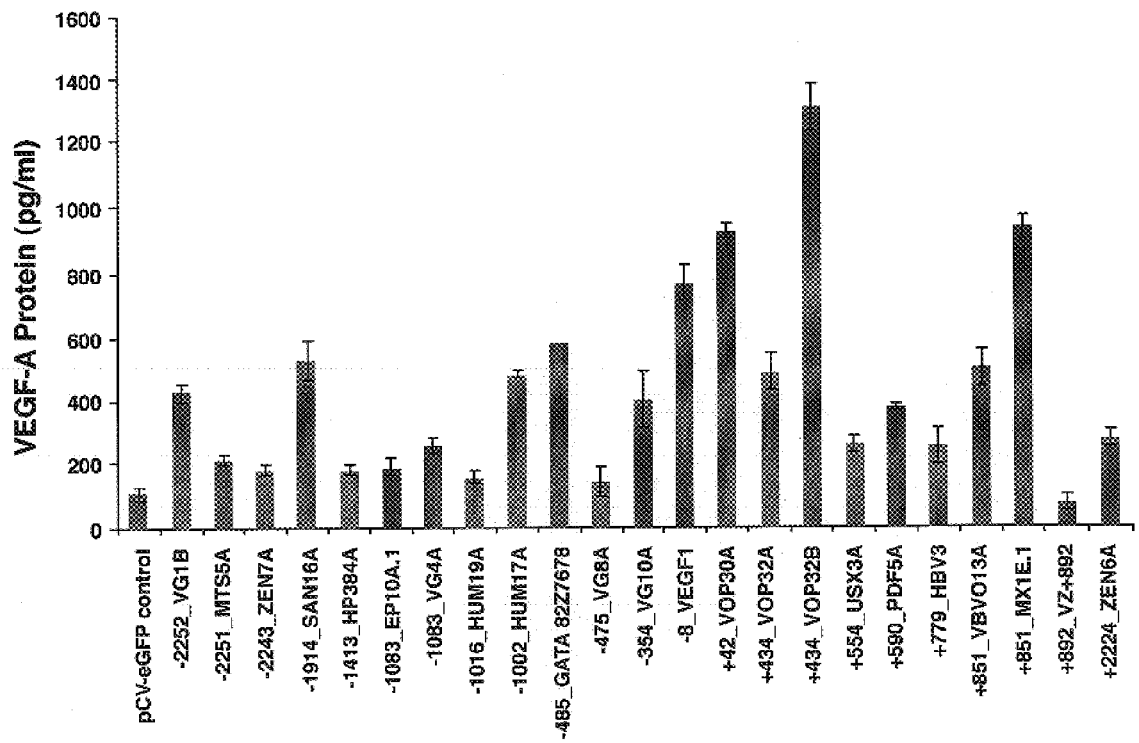

FIG. 10 shows levels of human VEGF-A protein, detected by ELISA, in HEK 293 cells transfected with different ZFP-encoding plasmids. See Tables 2–4 for the identities of the target sites and ZFP binding domains.

Figure 11:
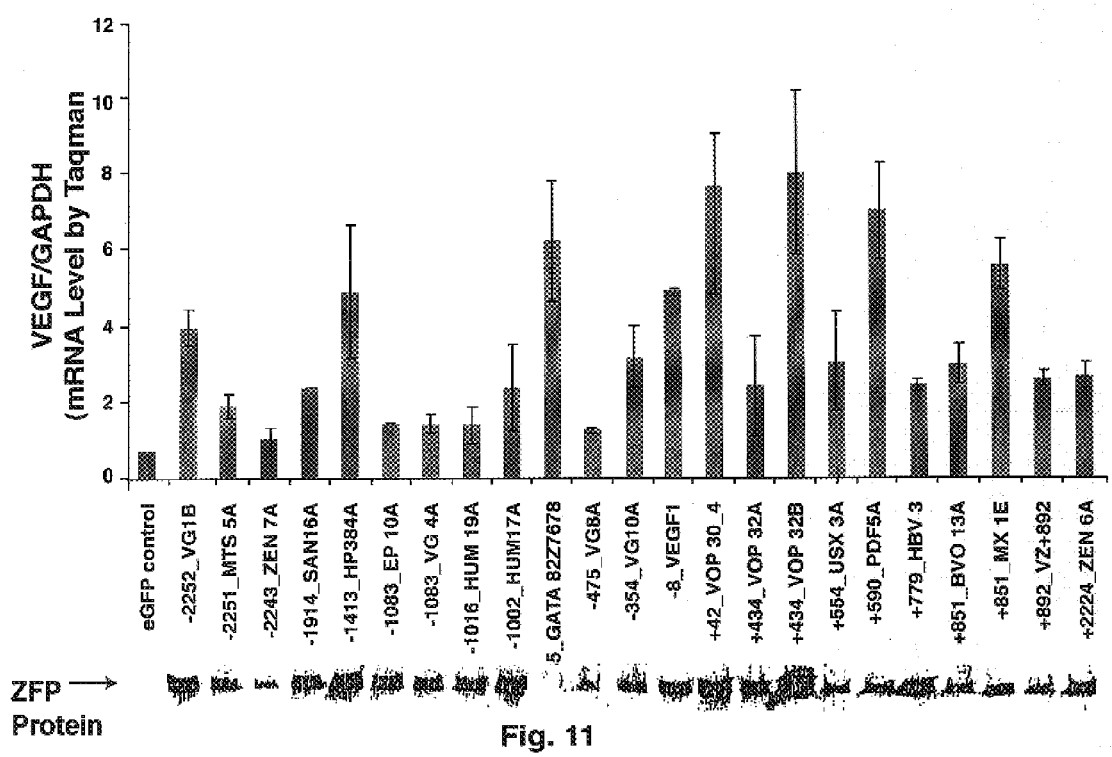

FIG. 11 shows levels of human VEGF-A mRNA, detected by real-time PCR (Taqman), in HEK 293 cells transfected with different ZFP-encoding plasmids. See Tables 3 and 4 for the identities of the ZFP binding domains. The lower portion of the figure shows immunoblot analysis of ZFP expression in transfected cells, using an anti-FLAG antibody.

Figure 12:
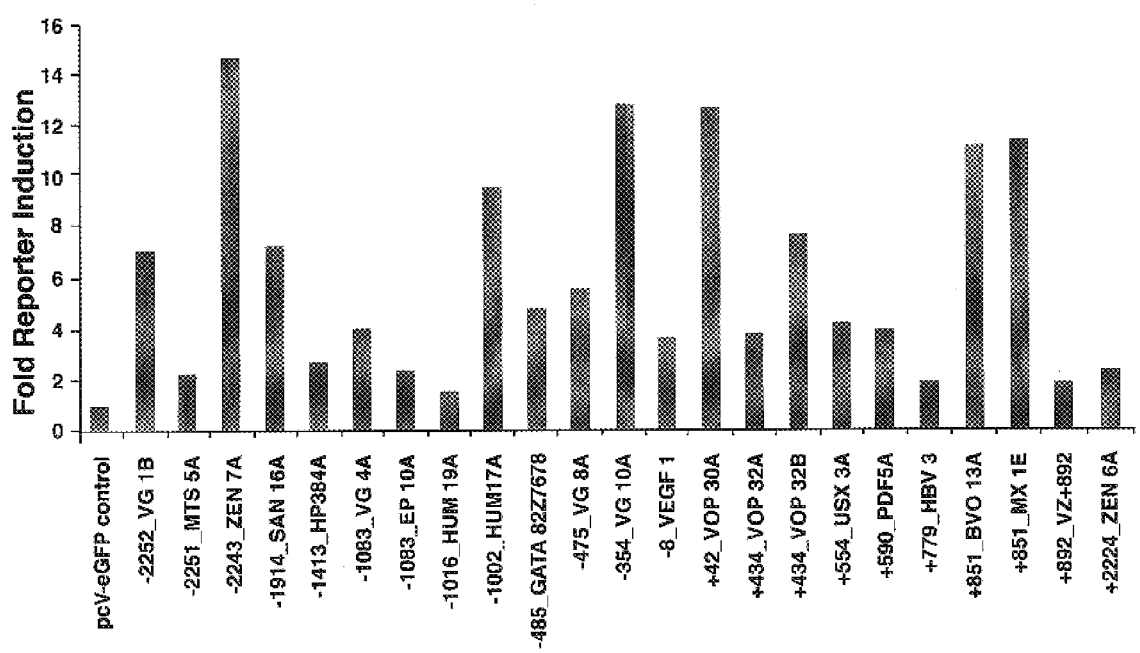

FIG. 12 shows an analysis of reporter gene activity in HEK 293 cells that were co-transfected with a plasmid encoding a luciferase reporter gene under the transcriptional control of a VEGF promoter and different ZFP-encoding plasmids. Fold-induction of luciferase activity is presented relative to a control plasmid in which ZFP-encoding sequences were replaced by sequences encoding green fluorescent protein.

Figure 13:
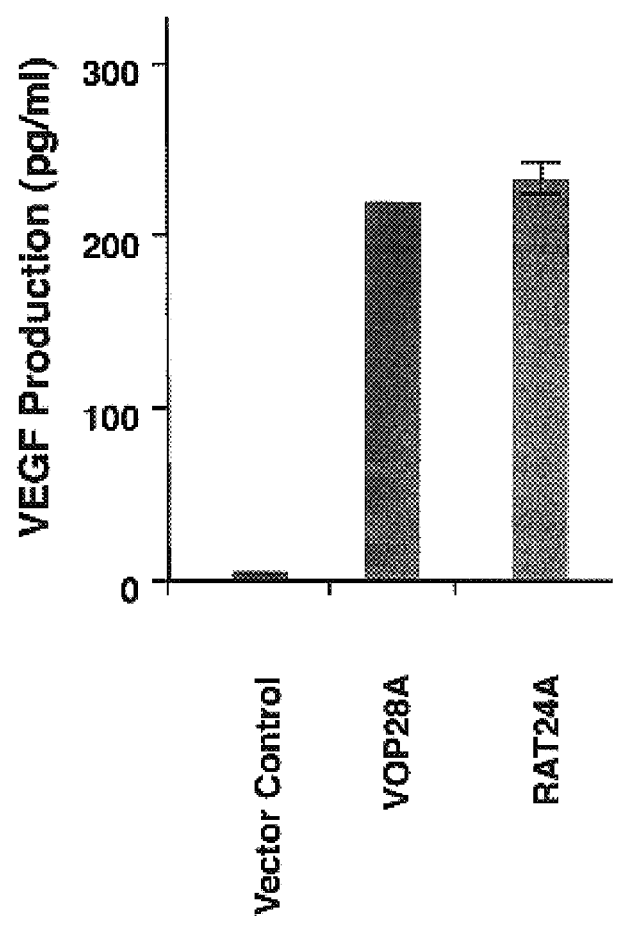

FIG. 13 shows levels of human VEGF-A protein, detected by ELISA, in HEK 293 cells transfected with different ZFP-encoding plasmids. See Tables 2–4 for the identities of the target sites and ZFP binding domains.

FIGS. 14A–14B show analysis of VEGF-A and VEGF-C mRNA in cells that had been transfected with different plasmids encoding ZFP-VP16 fusions. VEGF mRNA levels were analyzed and normalized with respect to GAPDH mRNA levels as described in Example 1. FIG. 14A shows analysis of VEGF-A mRNA levels; FIG. 14B shows analysis of VEGF-C mRNA levels. The name of the transfected ZFP binding domain (see Table 2) and the approximate location of its target site are indicated along the abscissa.

FIGS. 15A–D illustrate the targeting, design, and results of DNA binding analyses conducted with zinc finger proteins targeted to the mouse VEGF-A locus.

Figure 15A:
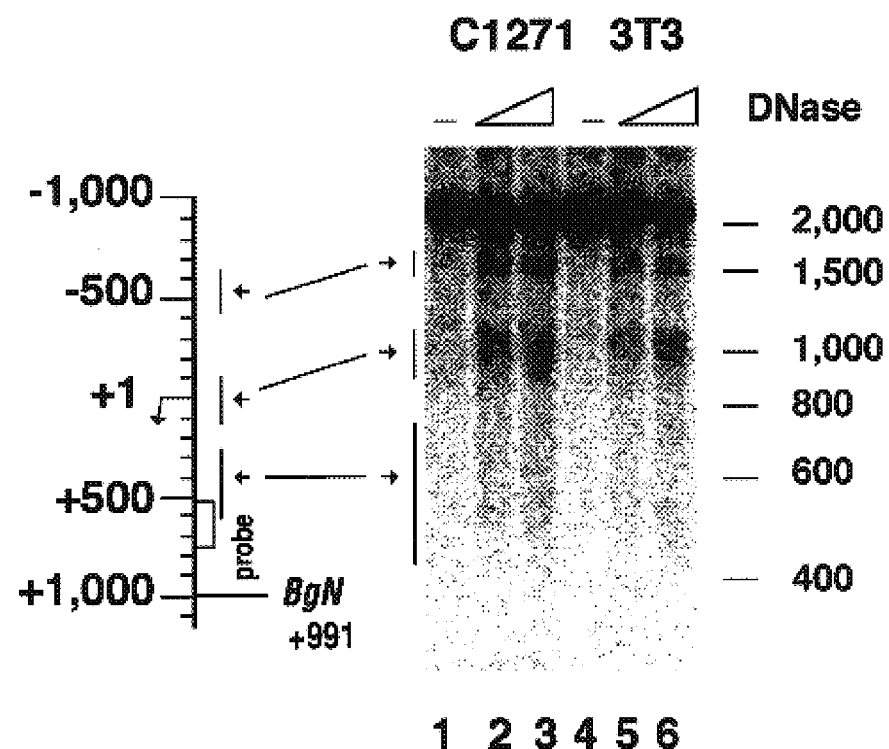

FIG. 15A depicts the results of mapping of DNase 1—accessible regions in the mouse VEGF-A promoter region. Nuclei from the indicated cell lines were partially digested with DNase I (see "Experimental Procedures"), followed by Southern blot analysis using Bgl 1 and the indicated probe. The vertical bar represents the promoter region of the VEGF-A locus. A hooked arrow denotes the transcription start site, and tick marks indicate units of 100 bp. The migration pattern for a set of DNA standard fragments is indicated at the right side of the gel, with the size of each fragment given in base pairs. Arrows are used to highlight the relationship of observed bands to location of accessible chromatin regions relative to the transcription start site of VEGF-A. DNAse I concentrations (U/ml) in lanes 1–6 were as follows: 0, 32, 64, 0, 8, and 16, respectively.

Figure 15B:
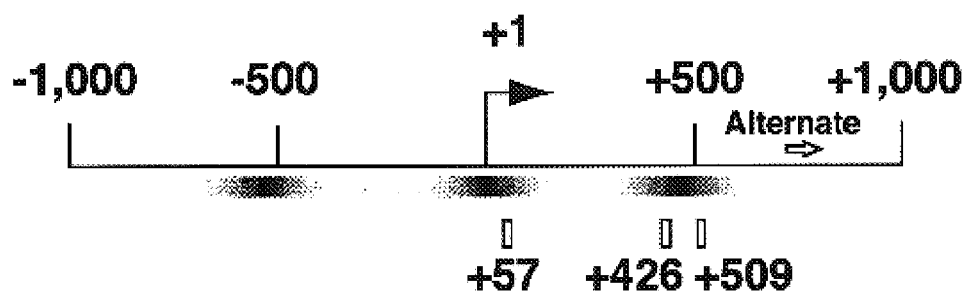

FIG. 15B shows the location of ZFP target sites used for one set of binding studies. A schematic representation of the human VEGF-A gene is provided, showing the location of the principal (filled arrow) and a reported alternate (open arrow) transcription initiation site, and the DNAse I accessible regions (gradient-filled rectangles) determined in these studies. ZFP target locations are indicated by vertical open rectangles, and the position of the 5'-most nucleotide of each ZFP target is indicated by the number below it. Numbering is relative to the start site of transcription.

FIG. 15C lists ZFP target sequences (SEQ ID NOS:207, 144, and 240, respectively) and finger designs (SEQ ID NOS:239, 238, 122, 57, 159, 35, 64, 85, 36, 112, 66, and 54, respectively). ZFPs are named according to target site location and the suffix mVZ (for mouse VEGF-A ZFP). Finger designs indicate the identity of amino acid residues at positions −1 to +6 of the alpha helix of each finger.

FIG. 15D shows gel-shift assays of binding affinity. A three-fold dilution series of each protein was tested for binding to its DNA target (SEQ ID NOS:207, 144, 240, and 141, respectively), with the highest concentration in lane 10 and the lowest concentration in lane 2. Lane 1 contains probe alone. Apparent Kd's, derived from the average of 3 such studies, are indicated at right. For mVZ+426 and mVZ+509, Kd's are provided as upper bounds (<0.01 nM), since the use of 0.01 nM of probe has probably led to an underestimate of the affinity of these proteins.

Figure 16:
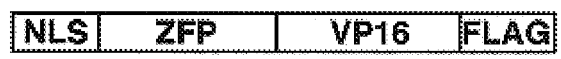
Figure 16:
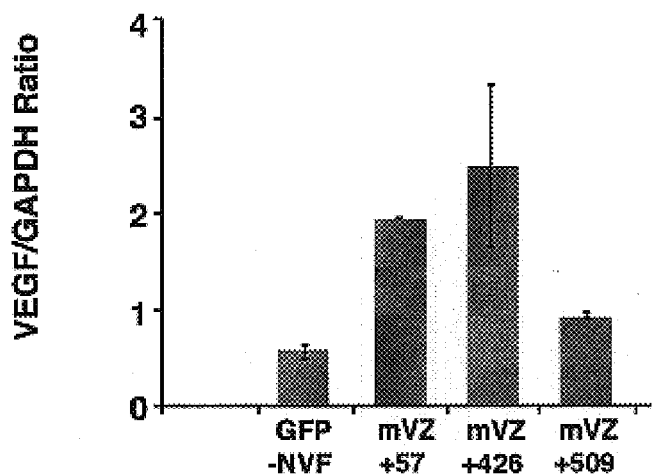
Figure 16:
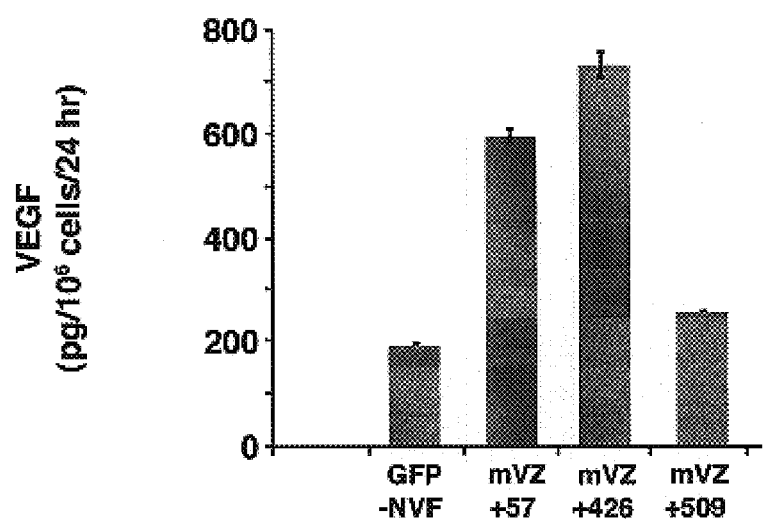

FIGS. 16A–16C depict ZFP-mediated activation of the mouse VEGF-A locus in C127I cells. Cells were transduced with retroviral vectors expressing each ZFP transcriptional activator or a control protein in which green fluorescent protein (GFP) was substituted for the ZFP DNA-binding domain. After selection for drug resistance, the resultant cell population was assayed for expression of VEGF-A by Taq-Man or ELISA.

FIG. 16A is a schematic representation of the ZFP transcriptional activators used in these studies. 'NLS', 'ZFP,' 'VP16' and 'FLAG' indicate the relative locations of, respectively, a nuclear localization signal, a ZFP binding domain, VP16 activation domain, and FLAG tag. See "Experimental Procedures" for a detailed description of the constructs.

FIG. 16B shows the measurement of ZFP-mediated activation of the VEGF-A locus in C127 I cells by TaqMan™ analysis. Expression of VEGF-A mRNA is normalized to GAPDH mRNA level.

FIG. 16C shows results of ZFP-mediated activation of VEGF-A locus by quantitating the level of secreted VEGF-A protein via ELISA (R&D systems).

FIGS. 17A–17D show Western blots that demonstrate induction of VEGF A expression by ZFPs.

Figure 17A:
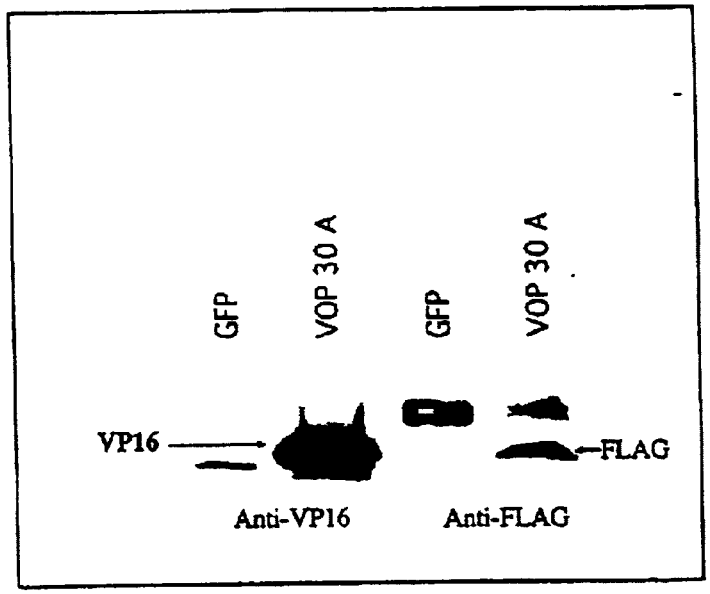

FIG. 17A shows the results of a Western blot that demonstrates expression of a ZFP fusion protein in cultured smooth muscle cells transduced with a recombinant adenovirus construct encoding a fusion protein comprising an NLS, ZFP VOP 30A, a VP16 activation domain and a FLAG epitope. Both anti-VP16 and anti-FLAG antibodies were used, as indicated. Cells transduced with a recombinant adenovirus encoding green fluorescent protein were used as control.

Figure 17B:
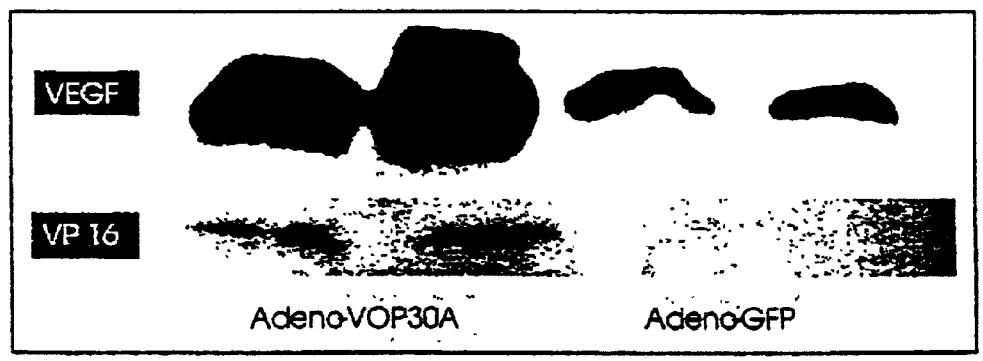

FIG. 17B presents a Western blot demonstrating a marked increase in VEGF-A expression in the hindlimb adductor muscle of CD-1 mice when injected with recombinant adenovirus encoding VOP 30A as compared to an adenovirus encoding green fluorescent protein (GFP) as control. Duplicate samples are shown.

Figure 17C:
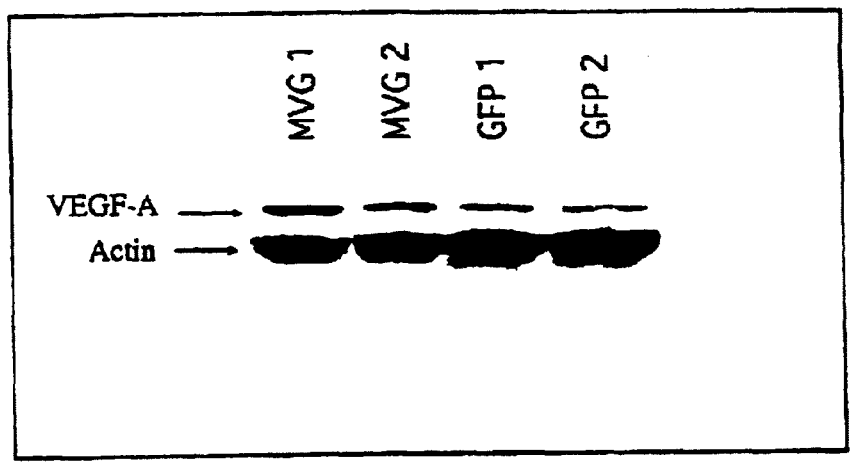

FIG. 17C is a Western blot showing induction of VEGF-A protein expression following injection of adeno-MVG (see Example 6) into mouse skeletal muscle relative to a control injection of an adenovirus encoding green fluorescent protein (GFP). Two different mice were injected with MVG and two separate mice with control as indicated. Levels of actin were also determined on the immunoblot as a loading control.

Figure 17D:
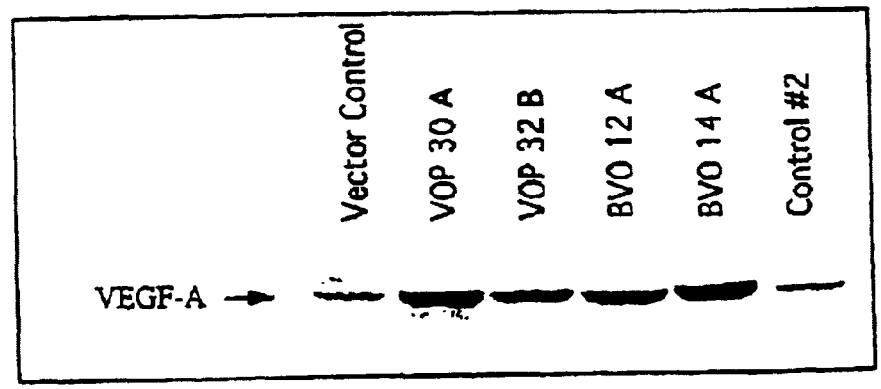

FIG. 17D shows a Western blot illustrating induction of VEGF-A in rat skeletal muscle after injection of plasmids encoding the VEGF-A modulating ZFPs VOP 30A, VOP 32B, BVO12A, BVO14A as compared to a control plasmid encoding a ZFP backbone but lacking the DNA recognition domain.

FIGS. 18A–E show results demonstrating induction of angiogenesis using an established model system.

FIGS. 18A and 18B are photographs of vascularization in mouse ears following injection with a recombinant adenovirus encoding either green fluorescent protein (GFP) as control (FIG. 18A) or a ZFP VOP 30A (FIG. 18B).

FIGS. 18C and 18D show similar photographs as those presented in FIGS. 18A and 18B but with an adenovirus encoding either green fluorescent protein (GFP) (FIG. 18C) or ZFP VOP 32 B (FIG. 18D).

FIG. 18E is a chart of the number of blood vessels as determined using immunostaining techniques (see Experimental Procedures section infra) at either three or six days after injection of a mouse ear with adenovirus of the type described in FIGS. 18C and 18D. The chart demonstrates increased vascularity and is consistent with the results shown in FIGS. 18A and 18B.

Figure 19A:
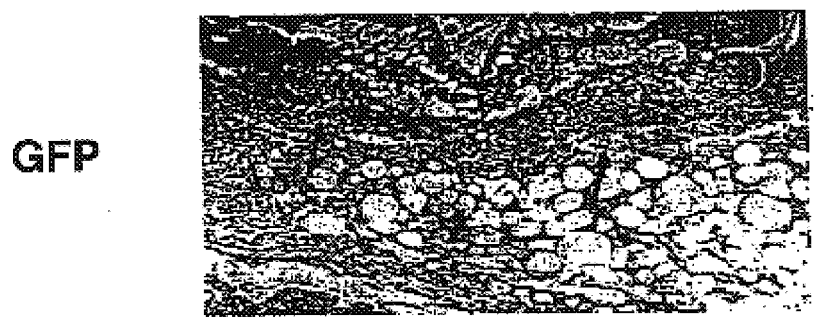
Figure 19B:
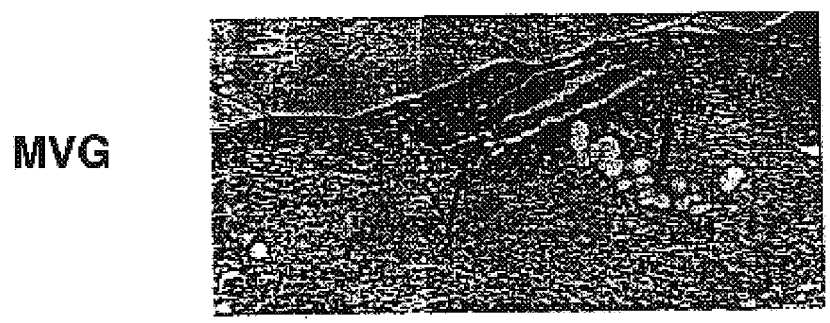
Figure 19C:
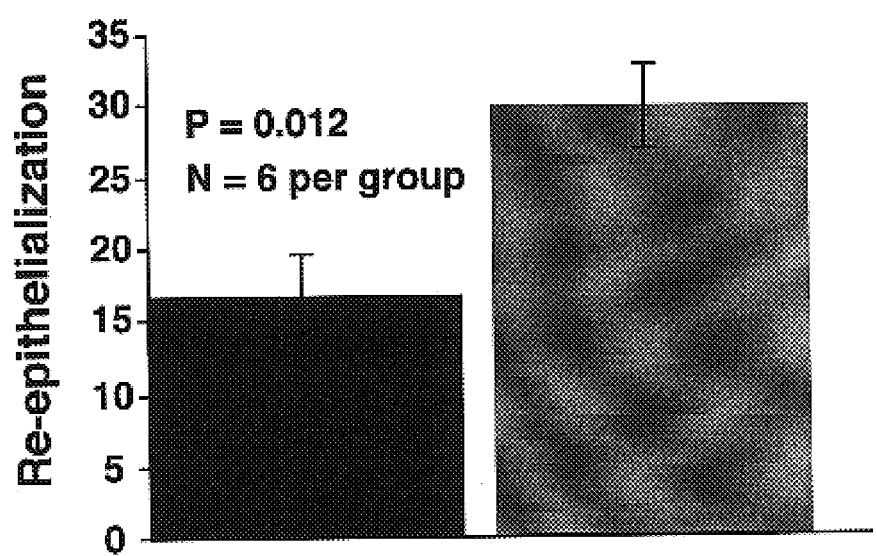

FIGS. 19A–19C present results showing that cutaneous wound healing is accelerated by VEGF-A regulating ZFPs. Bilateral cutaneous wounds were created in the backs of CD-1 mice by excising a 5 mm circle of skin. At the time of wounding, adenovirus encoding a VEGF-A regulating zinc finger protein or a control adenovirus encoding green fluorescent protein (GFP) was applied topically to the wound. Wounds were excised whole 5 days later, the tissue was fixed and paraffin embedded for histologic and immunohistologic analysis.

FIG. 19A illustrates the extent of reepithelialization following wounding and subsequent treatment by adenovirus encoding green fluorescent protein (GFP).

FIG. 19B illustrates how treatment with the adenovirus MVG augments the degree of reepithelialization noted at day 5 post-wounding. The arrows denote the leading edge of keratinocyte ingrowth into the wound. As this figure illustrates, the distance between the edges of keratinocyte ingrowth is decreased by VEGF-ZFP treatment; thus reepithelialization is augmented.

FIG. 19C is a chart summarizing the distance between leading edges of keratinocyte ingrowth in wounds treated with either adenovirus encoding a ZFP (dark shading) or green fluorescent protein (GFP) (light shading) and shows a significant reduction in distance for treatment with the VEGF-ZFP treatment as compared to the control.

Figure 20A:
Figure 20B:

FIGS. 20A and 20B show that wound reepithelialization is augmented by treatment with the adenovirus MVG. The lower arrowhead in each photograph marks the wound edge and the upper arrow marks the extent of keratinocyte ingrowth at day 5 post-wounding with a recombinant adenoviruses encoding MVG (FIG. 20B) or green fluorescent protein (GFP) as control (FIG. 20B).

FIGS. 21A–21C show that treatment of cutaneous wounds by topical application of recombinant adenovirus encoding a VEGF-A regulating ZFP (MVG) increases vascularity (FIG. 21A) as compared to an adenovirus encoding green fluorescent protein (GFP) (FIG. 21B). The presence of vessels is visualized with an immunostain containing antibodies specific for endothelial cells. FIG. 21C is a chart that summarizes vessel counts performed with digitally captured images when wounds were treated with adenovirus encoding a ZFP (dark box) or green fluorescent protein (GFP) (light box).

Figure 22:
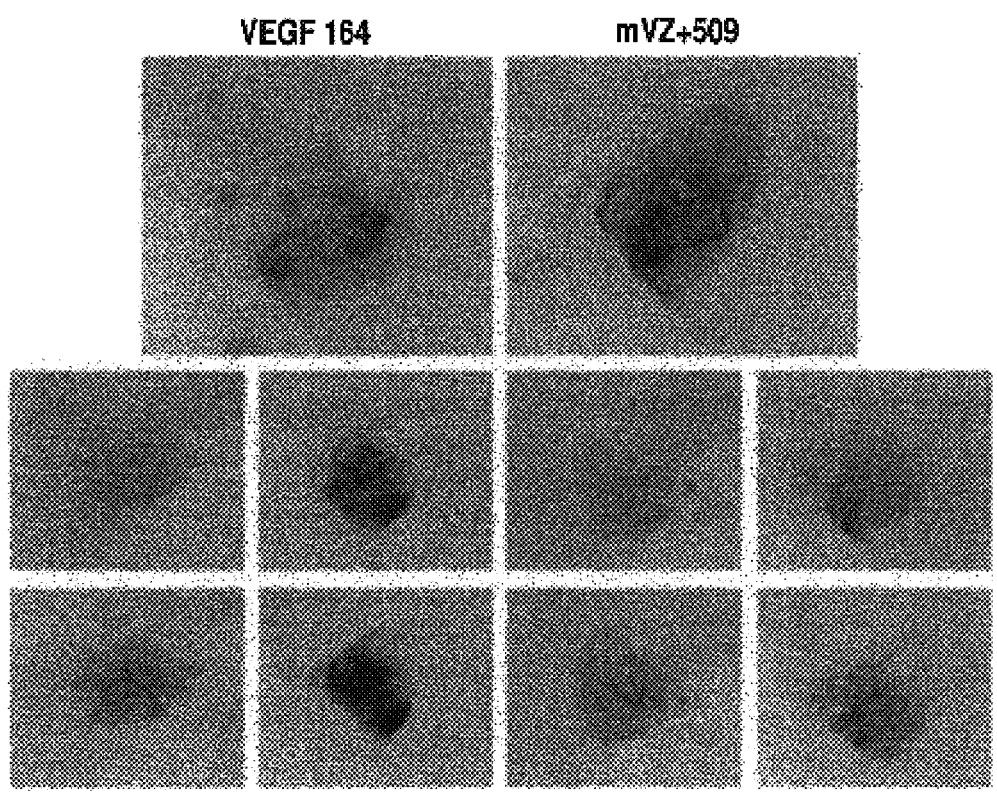

FIG. 22 shows angiogenesis stimulated by MVZ+509 (top and middle right panels) does not produce a hyperpermeable neovasculature as determined by Evans blue dye extravasation (bottom right). The neovasculature induced by VEGF164 adenovirus transduction (left panels) exhibit spontaneous hemorrhage and Evans blue extravasation.

DETAILED DESCRIPTION

I. Definitions

The practice of conventional techniques in molecular biology, biochemistry, cell culture, recombinant DNA, and related fields are well-known to those of skill in the art and are discussed, for example, in the following literature references: Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; and METHODS IN MOLECULAR BIOLOGY, Vol. 119, "Chromatin Protocols" (P. B. Becker, ed.) Humana Press, Totowa, 1999, all of which are incorporated by reference in their entireties.

The term "zinc finger protein" or "ZFP" refers to a protein having DNA binding domains that are stabilized by zinc. The individual DNA binding domains are typically referred to as "fingers" A ZFP has least one finger, typically two, three, four, five, six or more fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins (C2H2 class) is -Cys-(X)2-4-Cys-(X)12-His-(X)3-5-His (where X is any amino acid) (SEQ ID NO:208). Additional classes of zinc finger proteins are known and are useful in the practice of the methods, and in the manufacture and use of the compositions disclosed herein (see, e.g., Rhodes et al. (1993) Scientific American 268:56–65). Studies have demonstrated that a single zinc finger of this class consists of an alpha helix containing the two invariant histidine residues coordinated with zinc along with the two cysteine residues of a single beta turn (see, e.g., Berg & Shi, Science 271:1081–1085 (1996)).

A "target site" is the nucleic acid sequence recognized by a ZFP. A single target site typically has about four to about ten base pairs. Typically, a two-fingered ZFP recognizes a four to seven base pair target site, a three-fingered ZFP recognizes a six to ten base pair target site, and a six fingered ZFP recognizes two adjacent nine to ten base pair target sites.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (i.e., a "D-able subsite," see co-owned WO 00/42219) a subsite is four nucleotides in length and overlaps with another 3- or 4-nucleotide subsite.

"Kd" refers to the dissociation constant for a binding molecule, i.e., the concentration of a compound (e.g., a zinc finger protein) that gives half maximal binding of the compound to its target (i.e., half of the compound molecules are bound to the target) under given conditions (i.e., when [target]<<Kd), as measured using a given assay system (see, e.g., U.S. Pat. No. 5,789,538). The assay system used to measure the Kd should be chosen so that it gives the most accurate measure of the actual Kd of the ZFP. Any assay system can be used, as long is it gives an accurate measurement of the actual Kd of the ZFP. In one embodiment, the Kd for a ZFP is measured using an electrophoretic mobility shift assay ("EMSA"). Unless an adjustment is made for ZFP purity or activity, the Kd calculations may result in an overestimate of the true Kd of a given ZFP. Preferably, the Kd of a ZFP used to modulate transcription of a gene is less than about 100 nM, more preferably less than about 75 nM, more preferably less than about 50 nM, most preferably less than about 25 nM.

The term "VEGF gene" refers generally to any member of the VEGF family of genes as described supra or collection of genes from the VEGF family having a native VEGF nucleotide sequence, as well as variants and modified forms regardless of origin or mode of preparation. The VEGF genes can be from any source. Typically, the VEGF genes refer to VEGF genes in mammals, particularly humans. A VEGF gene having a native nucleotide sequence is a gene having the same nucleotide sequence as a VEGF gene as obtained from nature (i.e., a naturally occurring VEGF gene). More specifically, the term includes VEGF-A (including the isoforms VEGF-A121, VEGF-A145, VEGF-A165, VEGF-A189, and VEGF-A206); VEGF-B (including the isoforms VEGF-B167, and VEGF-B186); VEGF-C; VEGF-D; VEGF-E (various VEGF-like proteins from orf virus strains as described in the Background section); VEGF-H; VEGF-R; VEGF-X; VEGF-138; and P1GF (both P1GF-1 and P1GF-2). The term also includes variants of specific isoforms. For example, the term includes not only the isoform VEGF-145, but also VEGF-145-I, VEGF-145-II, and VEGF-145-III. The term also encompasses allelic variants, other isoforms resulting from alternative exon splicing, forms that are functionally equivalent to native sequences, and nucleic acids that are substantially identical to a native VEGF gene. More specifically, the term encompasses the following VEGF genes.

VEGF (VEGF-A) has been described by a number of researchers (see, e.g., Leung, et al. (1989) Science 246:1306–1309; Keck, et al. (1989) Science 246:1309–1312; and Conn et al. (1990) Proc. Natl. Acad. Sci. USA 87:2628–2632, each of which is incorporated herein in its entirety). The VEGF-A189 isoform is disclosed in U.S. Pat. No. 5,240,848, the VEGF-A121 isoform in U.S. Pat. Nos. 5,194,596 and 5,219,739; and the VEGF-A165 isoform in U.S. Pat. No. 5,332,671, each of which is incorporated by reference in its entirety.

VEGF-B is described in PCT Publication WO 96/26736, in U.S. Pat. Nos. 5,840,693, 5,607,918, and 5,928,939, each of which is incorporated herein in its entirety. See also, PCT Publications WO 96/27007 and WO 00/09148, and Olofsson et al. (1996) Proc. Natl. Acad. Sci. USA 93:2576–2581, each of which is incorporated herein by reference in its entirety.

VEGF-C is disclosed by Joukov et al., (1996) EMBO J. 15:290–298, and Lee et al. (1996) Proc. Natl. Acad. Sci. USA 93:1988–1992, as well as in U.S. Pat. Nos. 5,935,820; and 6,130,071, each of which is incorporated herein in its entirety. See also U.S. Pat. Nos. 5,776,755 and 5,932,540, as well as PCT Publications WO 95/24473; WO 96/39515; WO 97/05250; WO 97/09427; WO 97/17442; WO 98/33917; and WO 99/46364, each of which is incorporated herein by reference in its entirety. Other forms are discussed in EP 0 476 983 B1; U.S. Pat. Nos. 5,994,300 and 6,040,157; and PCT publication WO 00/45835, each of which are incorporated by reference in its entirety.

VEGF-D is described in PCT Publications WO 98/07832, WO 98/24811; and WO 99/33485. It is further described by Achen et al. (1988) Proc. Natl. Acad. Sci. USA 95:548–553, each of the foregoing being incorporated herein in its entirety. See also EP 0 935 001 A1, which is incorporated herein in its entirety.

The term also includes the various viral forms described in the Background section that are collectively referred to herein as VEGF-E. Such viral VEGF-like genes include the gene isolated from the orf viral strain NZ2 that is referred to in the literature variously as OV NZ2, ORFV2-VEGF, OV-VEGF2 and VEGF-ENZ2A (see, e.g., Lyttle, D. J. et al. (1994) J. Virology 68:84–92; and PCT Publication WO 00/25805). Also included are the gene identified in strain NZ7 (called NZ7, OV-VEGF7, VEGF-E and VEGF-ENZ7). This gene is discussed in Lyttle, D. J. et al. (1994) J. Virology 68:84–92; and Ogawa, S. et al. (1998) J. Biol. Chem. 273:31273–31282. Also included is the NZ10 gene which is disclosed in PCT Publication WO 00/25805. The gene from orf viral strain D1701 is also included (see, e.g., Meyer et al. (1999) EMBO J. 18:363–74, which is incorporated herein by reference in its entirety). Another viral VEGF-like protein from para-poxvirus has been disclosed in PCT Publication WO 99/50290.

The term further includes the mammalian VEGF-like protein that has also been referred to as VEGF-E (see, e.g., WO 99/4767)

The term also includes the gene called PDGF/VEGF-Like Growth Factor H, or simply VEGF-H that is discussed in PCT Publication WO 00/44903 (incorporated by reference in its entirety). VEGF-R (see, e.g., PCT Publication WO 99/37671, incorporated by reference in its entirety) and VEGF-X (see, e.g., PCT publication WO 00/37641, incorporated herein by reference in its entirety) are also included, as is the recently identified VEGF-138 gene. The various isoforms (P1GF1 and P1GF2) of the Placenta Growth Factor, P1GF, are further included in the term. Methods for isolating and characterizing this gene and the protein it encodes are set forth in Maglione et al. (1991) Proc. Natl. Acad. Sci. USA 88:9267–9271, which is incorporated herein by reference in its entirety. See also, Birkenhager, R. (1996) Biochem. J. 316:703–707; Kao, Y. (1997) Biochem. Biophys. Res. Commun. 235:493–498; Kao, Y. (1996) J. Biol. Chem. 271:3154–3162; and Klauss, M. (1996) J. Biol. Chem. 271:17629–17634, each of which is incorporated by reference in its entirety.

As indicated supra, the term VEGF gene includes nucleic acids that are substantially identical to a native sequence VEGF gene. The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40–60 residues in length or any integral value therebetween, preferably over a longer region than 60–80 residues, more preferably at least about 90–100 residues, and most preferably the sequences are substantially identical over the full length of the sequences being compared, such as the coding region of a nucleotide sequence for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987–1999, including supplements such as supplement 46 (April 1999)]. Use of these programs to conduct sequence comparisons are typically conducted using the default parameters specific for each program.

Another example of an algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. This is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For determining sequence similarity the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Hybridizes substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) Proteins, W.H. Freeman and Company. In addition, individual substitutions, deletions or additions which alter, add or delete a single amino acid or a small percentage of amino acids in an encoded sequence are also "conservatively modified variations."

The term "VEGF protein" refers to a protein encoded by a VEGF gene and includes functional equivalents of such proteins.

A "functional fragment" or "functional equivalent" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid, binding to a regulatory molecule) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245–246; U.S. Pat. No. 5,585,245 and PCT WO 98/44350.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. Thus, the term polynucleotide sequence is the alphabetical representation of a polynucleotide molecule. This alphabetical representation can be input into databases in a computer having a central processing unit and used for bioinformatics applications such as functional genomics and homology searching. The terms additionally encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). The nucleotide sequences are displayed herein in the conventional 5'-3' orientation.

Chromatin is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

A "fusion molecule" is a molecule in which two or more subunit molecules are linked, typically covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" refers to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene activation can constitute, for example, inhibition of repression as well as stimulation of expression above an existing level. Examples of gene activation processes which increase translation include those that increase translational initiation, those that increase translational elongation and those that increase mRNA stability. In general, gene activation comprises any detectable increase in the production of a gene product, in some instances an increase in production of a gene product by about 2-fold, in other instances from about 2- to about 5-fold or any integer therebetween, in still other instances between about 5- and about 10-fold or any integer therebetween, in yet other instances between about 10- and about 20-fold or any integer therebetween, sometimes between about 20- and about 50-fold or any integer therebetween, in other instances between about 50- and about 100-fold or any integer therebetween, and in yet other instances between 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, in some instances a decrease in production of a gene product by about 2-fold, in other instances from about 2- to about 5-fold or any integer therebetween, in yet other instances between about 5- and about 10-fold or any integer therebetween, in still other instances between about 10- and about 20-fold or any integer therebetween, sometimes between about 20- and about 50-fold or any integer therebetween, in other instances between about 50- and about 100-fold or any integer therebetween, in still other instances 100-fold or more. In yet other instances, gene repression results in complete inhibition of gene expression, such that no gene product is detectable.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961–964 (1997)); changes in signal transduction, phosphorylation and dephosphorylation, receptor-ligand interactions, second messenger concentrations (e.g., cGMP, cAMP, IP3, and Ca2+), cell growth, and neovascularization. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" or "functional domain" refers to a protein or a protein domain that has transcriptional modulation activity when tethered to a DNA binding domain, i.e., a ZFP. Typically, a regulatory domain is covalently or non-covalently linked to a ZFP (e.g., to form a fusion molecule) to effect transcription modulation. Regulatory domains can be activation domains or repression domains. Activation domains include, but are not limited to, VP16, VP64 and the p65 subunit of nuclear factor Kappa-B. Repression domains include, but are not limited to, KRAB MBD2B and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498–502 (1998)). Alternatively, a ZFP can act alone, without a regulatory domain, to effect transcription modulation.

The term "operably linked" or "operatively linked" is used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operably linked" or "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette," "expression cassette" or "expression construct" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV") thymidine kinase ("tk") promoter or a mutated HSV tk promoter, as described in Eisenberg & McKnight, Mol. Cell. Biol. 5:1940–1947 (1985).

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains an expression vector or nucleic acid, either of which optionally encodes a ZFP or a ZFP fusion protein. The host cell typically supports the replication or expression of the expression vector. Host cells can be prokaryotic cells such as, for example, *E. coli*, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

The term "naturally occurring," as applied to an object, means that the object can be found in nature, as distinct from being artificially produced by humans.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The term "ischemia" broadly refers to a condition of localized anemia due to an inadequate blood supply to the particular area (e.g., a tissue or organ), usually due to a blockage. Ischemia can be associated with a variety of diseases that involve a blockage of blood flow such as coronary artery disease and peripheral vascular disease, for example.

"Angiogenesis" broadly refers to the process of developing new blood vessels. The process involves proliferation, migration and tissue infiltration of capillary endothelial cells from pre-existing blood vessels. Angiogenesis is important in normal physiological processes, including for example, follicular growth, embryonal development and wound healing and in pathological processes such as tumor growth and metastasis. The term "modulation" refers to a change in extent, duration, levels, or properties of a physiologic process. For example modulation of angiogenesis could comprise an increase in the formation of new blood vessels or a decrease in the formation of new blood vessels. Modulation of angiogenesis could also refer to the stimulation of the formation of nonpermeable or nonhyperpermeable blood vessels. Various assays for angiogenesis are described infra.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

By an "effective" amount (or "therapeutically effective" amount) of a pharmaceutical composition is meant a sufficient, but nontoxic amount of the agent to provide the desired effect. The term refers to an amount sufficient to treat a subject. Thus, the term therapeutic amount refers to an amount sufficient to remedy a disease state or symptoms, by preventing, hindering, retarding or reversing the progression of the disease or any other undesirable symptoms whatsoever. The term prophylactically effective amount refers to an amount given to a subject that does not yet have the disease, and thus is an amount effective to prevent, hinder or retard the onset of a disease.

A "wound" refers broadly to trauma to any tissue. A wound can result from an injury such as caused by violence, accident or surgery. A wound can include laceration or breakage of a epithelial layer (e.g., the skin) with damage to underlying tissue.

II. Overview

A variety of methods are provided herein for modulating angiogenesis and treating ischemia. In some instances, such methods involve contacting a cell or population of cells such as in an organism, with one or more zinc finger proteins (ZFPs) that bind to specific sequences in one or more VEGF genes. In certain methods, one ZFP is administered and is able to bind to a target site in different VEGF genes (e.g., a target site in VEGF-A, VEGF-B and VEGF-C). Other methods involve administering a plurality of different ZFPs that bind to a multiple target sites within a particular gene.

Thus, also provided herein are a variety of zinc finger proteins that are engineered to specifically recognize and bind to particular nucleic acid segments (target sites), thereby modulating the expression of one or more VEGF genes. In one embodiment, the ZFPs are linked to regulatory domains to create chimeric transcription factors to activate or repress transcription of VEGF genes. With such ZFPs, expression of certain VEGF genes can be enhanced; with certain other ZFPs, expression can be repressed. In general, the target sites to which the ZFPs bind are sites that result in activation or repression of expression of VEGF gene. The target site can be adjacent to, upstream of, and/or downstream of the transcription start site (defined as nucleotide 0). As indicated above, some of the present ZFPs modulate the expression of a single VEGF gene. Other ZFPs modulate the expression of a plurality of VEGF genes. Thus, depending upon the particular ZFP(s) utilized, one can tailor the level at which one or more VEGF genes are expressed. In addition, multiple ZFPs or ZFP fusion molecules, having distinct target sites, can be used to regulate a single VEGF gene.

By virtue of the ability of the ZFPs to bind to target sites and influence expression of VEGF genes, coupled with the diverse functions of VEGF genes, the ZFPs provided herein can be used in a wide variety of applications. In general, the ZFPs can be used to regulate the growth of a variety of endothelial cells, either by activating or repressing growth. In certain applications, the ZFPs can be used to activate expression of VEGF genes to trigger beneficial angiogenesis in cell populations, both in vitro and in vivo. Such activation can be utilized for example to promote the formation of new blood vessels and capillaries in treatments for ischemic conditions. For instance, the ZFPs can be used to stimulate the development of collateral circulation in individuals having any of a variety of arterial or venous obstructions, such as individuals having arthrosclerosis. The ZFPs can also be used to promote lymphogenesis (the formation of lymphatic vessels) and myelopoiesis (the formation of the tissue elements of bone marrow and/or types of blood cells derived from bone marrow), and can be used to regenerate blood vessels and tissue in wounds.

Other methods involve repression of angiogenesis. Hence, the ability to utilize certain of the ZFPs provided herein to repress the expression of VEGF genes can be useful in other instances. For example, the ZFPs can be administered to prevent endothelial growth when such growth is undesirable, such as in blocking the formation of additional blood vessels to tumors, in preventing proliferation of the microvascular system in pathologies such as diabetic retinopathy and pathological angiogenesis associated with arthritis.

The ZFPs can also be employed in applications other than therapeutic applications. For instance, the ZFPs can be used to screen for agents capable of countering either activation or repression of VEGF gene expression. Also described herein are nucleic acids that encode the zinc finger proteins. Additionally, agents identified through the screening methods, the nucleic acids encoding the ZFPs and/or the ZFPs themselves can be utilized in pharmaceutical compositions to treat a variety of disorders, such as those just described.

III. Zinc Finger Proteins for Regulating Gene Expression

A. General

The zinc finger proteins (ZFPs) disclosed herein are proteins that can bind to DNA in a sequence-specific manner. As indicated supra, these ZFPs can be used in a variety of applications, including modulating angiogenesis and in treatments for ischemia. An exemplary motif characterizing one class of these proteins, the C2H2 class, is -Cys-(X)2-4-Cys-(X)12-His-(X)3-5-His (where X is any amino acid) (SEQ. ID. NO:208). Several structural studies have demonstrated that the finger domain contains an alpha helix containing the two invariant histidine residues and two invariant cysteine residues in a beta turn coordinated through zinc. However, the ZFPs provided herein are not limited to this particular class. Additional classes of zinc finger proteins are known and can also be used in the methods and compositions disclosed herein (see, e.g., Rhodes, et al. (1993) Scientific American 268:56–65). In certain ZFPs, a single finger domain is about 30 amino acids in length. Zinc finger domains are involved not only in DNA-recognition, but also in RNA binding and in protein-protein binding.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1, 2, 3 and 6 on each recognition helix making contacts with their respective DNA triplet subsites. The amino terminus of Zif268 is situated at the 3' end of the DNA strand with which it makes most contacts. Some zinc fingers can bind to a fourth base in a target segment. If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

B. Exemplary ZFPs

ZFPs that bind to particular target sites on a nucleic acid that includes a VEGF gene are disclosed herein. Thus, the ZFPs can include a variety of different component fingers of varying amino acid composition, provided the ZFP binds to the target sites provided herein. Locations of target sites in several VEGF genes are given in Table 2 and the sequences of the target sites are listed in Tables 3 and 4 below in column 2 labeled "Target" in each of these two tables. Transcription start sites for certain of the VEGF genes have not yet been precisely established. Thus, the site location listed in Table 2 for the following VEGF genes assumes that the transcription start site is at the location indicted for a particular GenBank entry as follows:

| Gene | Assumed Transcription Start Site |
| --- | --- |
| VEGF A | bp 2363 of GenBank entry AF095785 |
| VEGF B | bp 400 of GenBank entry U80601 |
| VEGF-C | bp 600 of GenBank entry AF020393 |
| VEGF-D | bp 18727 of GenBank entry U69570 |
| VEGF-E | bp 30278 (antisense strand) of GenBank entry AC015837 |
| Viral VEGFs | bp 230 of GenBank entry S67520 |

As indicated supra, the target sites can be located upstream or downstream of the transcriptional start site (defined as nucleotide 0). Some of the target sites include 9 nucleotides (see Table 3), whereas other sites include 18 nucleotides (see Table 4). One feature of these target sites is that binding of a ZFP, or a fusion protein including a ZFP and one or more regulatory domains, to the target site can affect the level of expression of one or more VEGF genes. As defined supra, VEGF genes that can be regulated by the ZFPs provided herein include, but are not limited to, VEGF-A (including isoforms VEGF-A121, VEGF-A145, VEGF-A165, VEGF-A189, and VEGF-A206), VEGF B (including isoforms VEGF-B167, and VEGF-B186), VEGF C, VEGF D, the viral VEGF-like proteins (viral VEGF-E) and mammalian VEGF-E, VEGF-H, VEGF-R, VEGF-X, VEGF-138 and P1GF (including P1GF-1 and P1GF-2). The target sites can be located adjacent the transcription start site or be located significantly upstream or downstream of the transcription start site. Some target sites are located within a single VEGF gene such that binding of a ZFP to the target affects the expression of a single VEGF gene. Other target sites are located within multiple VEGF genes such that the binding of a single ZFP can modulate the expression of multiple genes. In still other instances multiple ZFPs can be used, each recognizing targets in the same gene.

The ZFPs that bind to these target sites typically include at least one zinc finger but can include a plurality of zinc fingers (e.g., 2, 3, 4, 5, 6 or more fingers). Usually, the ZFPs include at least three fingers. Certain of the ZFPs include six fingers. The ZFPs that include three fingers typically recognize a target site that includes 9 or 10 nucleotides; ZFPs having six fingers can recognize target sites that include 18 to 20 nucleotides. The ZFPs can also be fusion proteins that include one or more regulatory domains, which domains can be transcriptional activation or repressor domains.

Tables 3 and 4 show the amino acid sequences of a number of different ZFPs and the corresponding target sites to which they bind. Table 3 lists ZFPs that bind to target sites that include 9 nucleotides. The first column in this table lists an internal reference name of the ZFP. Column 2 includes the 9 base target site bound by a three-finger zinc finger protein, with the target sites listed in 5' to 3' orientation. The corresponding SEQ ID NO. for the target site is listed in column 3. The amino acid sequences of portions of the three zinc finger components involved in recognition are listed in columns 4, 6 and 8, and their corresponding SEQ ID NOs. are listed in columns 5, 7 and 9, respectively. The numbering convention for zinc fingers is defined below. Column 10 lists the dissociation constants for some of the ZFP/target site complexes. Methods for determining such constants are described infra. Excluding cross-strand interactions, each finger binds to a triplet of bases (a target subsite) within a corresponding target sequence. The first finger binds to the first triplet starting from the 3' end of a target site, the second finger binds to the second triplet, and the third finger binds the third (i.e., the 5'-most) triplet of the target sequence. Thus, for example, the RSDHLAR finger (SEQ ID NO30) of the ZFP BVO 13A (first column of Table 3) binds to 5'GGG3', the DRSNLTR finger (SEQ ID NO: 36) binds to 5'GAC3' and the RSDALTQ finger (SEQ ID NO:88) binds to 5'ATG3'.

Table 4 provides information on six-finger ZFPs targeting VEGF genes. Table 4 has a similar format to Table 3, with column 1 indicating the internal reference name of the ZFP. In contrast to Table 3, however, column 2 of Table 4 includes the 18 base target site recognized by a six-finger protein (here, too, targets are listed in a 5' to 3' orientation), with the corresponding SEQ ID NO. listed in column 3. The amino acid sequences of portions of the six zinc finger components involved in recognition are listed in columns 4, 6, 8, 10, 12 and 14, with associated SEQ ID NOs. being listed in columns 5, 7, 9, 11, 13 and 15, respectively. In ZFPs of this type, the first finger binds to the first triplet starting from the 3' end of a target site, the second finger binds to the second triplet, the third finger binds the third triplet, the fourth finger binds to the fourth triplet, the fifth finger binds to the fifth triplet and the sixth finger binds to the sixth (i.e., the 5'-most) triplet of the target sequence (again excluding cross-strand interactions). Hence, for the ZFP named BVO 10A-9A, the first finger QSSDLRR (SEQ ID NO:120) binds 5'GCT3', the second finger RSDHLTR (SEQ ID NO:123) binds 5'GGG3', the third finger DRSALAR (SEQ ID NO:126) binds 5'GTC3', the fourth finger RSDHLAR (SEQ ID NO: 129) binds 5'GGG3', the fifth finger RSDNLAR (SEQ ID NO:132) binds 5'GAG3' and the sixth finger RSDALTR (SEQ ID NO:135) binds 5'GTG3'.

Accordingly, some of the target sites for the ZFPs provided herein, as well as specific examples of such ZFPs are disclosed in Tables 3 and 4. The segments or regions of the VEGF genes that were examined for potential target sites are indicated in Table 1. The numbers listed in Table 1 refer to the starting and ending base (in kbp) relative to the transcription start site for various VEGF genes that were examined to identify target sites. Negative numbers refer to kbp upstream of the transcription start site and positive numbers refer to kbp downstream of the transcription start site, where the transcription start site is defined as nucleotide 0. The VEGF sequences examined for target sites include the sequences for VEGF-A (see GenBank accession number AF095785), VEGF-B (see GenBank accession number U80601—from −0.4 kb to +0.32 kb), VEGF-C (see GenBank accession number AF020393) and VEGF-D genes (see, HSU69570 and HSY12864), as well as the sequences for P1GF (see, GenBank accession number AC015837) and viral VEGF-E genes (see, GenBank accession number AF106020 and Meyer, M., et al. (1999) EMBO J. 18:363–74; GenBank accession number S67520 and Lyttle, D. J. et al. (1994) J. Virol. 68:84–92; and GenBank accession number AF091434). References providing the sequences for each of these genes are listed supra. Thus, for example and with reference to Table 1, the nucleotide sequence of the VEGF-A gene examined for target sites extended from 2.3 kb upstream of the transcriptional start site to 1.1 kb downstream of the transcriptional start site.

The location(s) of the target site(s) for a particular ZFP in the various VEGF genes is summarized in Table 2. The first column in this table is an internal reference name for a ZFP and corresponds to the same name in column 1 of Tables 3 and 4. The location of the 5' end of the target site in various VEGF gene sequences is listed in the remaining columns. Again, negative numbers refer to the number of nucleotides upstream of the transcriptional start site (defined as nucleotide 0), whereas positive numbers indicate the number of nucleotides downstream of the transcriptional start site. Hence, the target site (5' end) for the ZFP named BVO 13A (row 1 of Table 2) in the VEGF A nucleotide sequence begins at the nucleotide located 851 bases downstream of the principal transcriptional start site for VEGF A. Certain target sites appear in multiple VEGF genes. For instance, the target site (5' end) for the ZFP named VG 4A in the VEGF A nucleotide sequence begins at the nucleotide located 1083 bases upstream of the transcriptional start site for VEGF A. The same target site (5' end) also begins at nucleotide 31 upstream of the transcriptional start site for VEGF B and 252 bases upstream of the transcription start site for VEGF C. Certain ZFPs, have more than one target site in a single VEGF gene; e.g., EP 10A has two target sites in the VEGF A gene (see Table 2).

Consequently, as indicated supra, certain ZFPs described herein can be utilized to modulate angiogenesis by modulating the activity of single VEGF genes, while other ZFPs can be utilized to regulate expression of a plurality of genes. The ZFP referred to as VG 8A, for example, has a binding site for each of the VEGF genes listed in Table 2, and thus can be utilized to regulate expression of a variety of VEGF genes simultaneously. By judicious selection of the various ZFPs provided herein and/or combinations thereof, one can tailor which VEGF genes are modulated.

IV. Characteristics of ZFPs

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand. In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. For example, if a zinc finger protein comprises from N-terminal to C-terminal first, second and third fingers that individually bind, respectively, to triplets 5' GAC3', 5'GTA3' and 5"GGC3' then the zinc finger protein binds to the target segment 3'CAGATGCGG5' (SEQ ID NO: 209). If the zinc finger protein comprises the fingers in another order, for example, second finger, first finger, third finger, then the zinc finger protein binds to a target segment comprising a different permutation of triplets, in this example, 3'ATG-CAGCGG5' (SEQ ID NO: 210). See Berg & Shi, Science 271, 1081–1086 (1996). The assessment of binding properties of a zinc finger protein as the aggregate of its component fingers may, in some cases, be influenced by context-dependent interactions of multiple fingers binding in the same protein.

Two or more zinc finger proteins can be linked to have a target specificity that is the aggregate of that of the component zinc finger proteins (see e.g., Kim & Pabo, Proc. Natl. Acad. Sci. U.S.A. 95, 2812–2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZZ__AAABBBCCC5', where the underline indicates a short intervening region (typically 0–5 bases of any type). In this situation, the target site can be viewed as comprising two target segments separated by an intervening segment.

Linkage can be accomplished using any of the following peptide linkers.

T G E K P: (SEQ ID NO:211) (Liu et al., 1997, supra.); (G4S)n (SEQ ID NO:212) (Kim et al., Proc. Natl. Acad. Sci. U.S.A. 93:1156–1160 (1996.); GGRRGGGS; (SEQ ID NO:213) LRQRDGERP; (SEQ ID NO:214) LRQKDGGGSERP; (SEQ ID NO:215) LRQKD(G3S) 2ERP (SEQ ID NO:216) Alternatively, flexible linkers can be rationally designed using computer programs capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

Linkage of two zinc finger proteins is advantageous for conferring a unique binding specificity within a mammalian genome. A typical mammalian diploid genome consists of 3×10$^9$ bp. Assuming that the four nucleotides A, C, G, and T are randomly distributed, a given 9 bp sequence is present ~23,000 times. Thus a ZFP recognizing a 9 bp target with absolute specificity would have the potential to bind to ~23,000 sites within the genome. An 18 bp sequence is present once in 3.4×10$^{10}$ bp, or about once in a random DNA sequence whose complexity is ten times that of a mammalian genome.

A component finger of zinc finger protein typically contains about 30 amino acids and, in one embodiment, has the following motif (N-C):

$$\text{Cys-(X)2-4-Cys-X.X.X.X.X.X.X.X.X.X.X.X-His-(X)3-5-His}\atop{-1\ 1\ \ 2\ 3\ 4\ 5\ 6\ 7}$$
(SEQ ID NO:208)

The two invariant histidine residues and two invariant cysteine residues in a single beta turn are coordinated through zinc atom (see, e.g., Berg & Shi, Science 271, 1081–1085 (1996)). The above motif shows a numbering convention that is standard in the field for the region of a zinc finger conferring binding specificity. The amino acid on the left (N-terminal side) of the first invariant His residue is assigned the number +6, and other amino acids further to the left are assigned successively decreasing numbers. The alpha helix begins at residue 1 and extends to the residue following the second conserved histidine. The entire helix is therefore of variable length, between 11 and 13 residues.

V. Design of ZFPs

The ZFPs provided herein are engineered to recognize a selected target site in a VEGF gene such as shown in Tables 3, 4 and 6. The process of designing or selecting a ZFP typically starts with a natural ZFP as a source of framework residues. The process of design or selection serves to define nonconserved positions (i.e., positions −1 to +6) so as to confer a desired binding specificity. One suitable ZFP is the DNA binding domain of the mouse transcription factor Zif268. The DNA binding domain of this protein has the amino acid sequence:

YACPVESCDRRFSRSDELTRHIRIHTGQKP (F1) (SEQ ID NO:217)

FQCRICMRNFSRSDHLTTHIRTHTGEKP (F2) (SEQ ID NO:218)

FACDICGRKFARSDERKRHTKIHLRQK (F3) SEQ ID NO:219)

and binds to a target 5' GCG TGG GCG 3' (SEQ ID NO:220).

Another suitable natural zinc finger protein as a source of framework residues is Sp-1. The Sp-1 sequence used for construction of zinc finger proteins corresponds to amino acids 531 to 624 in the Sp-1 transcription factor. This sequence is 94 amino acids in length. The amino acid sequence of Sp-1 is as follows:

```
PGKKKQHICHIQGCGKVYGKTSHLRAHLRWHTGE  (SEQ ID NO:221)
RPFMCTWSYCGKRFTRSDELQRHKRTHTGEKKFA
CPECPKRFMRSDHLSKHIKTHQNKKG
```

Sp-1 binds to a target site 5'GGG GCG GGG3' (SEQ ID No:222).

An alternate form of Sp-1, an Sp-1 consensus sequence, has the following amino acid sequence:

```
meklrngsgdPGKKKQHACPECGKSFSKSSHLRA  (SEQ ID NO:223)
HQRTHTGERPYKCPECGKSFSRSDELQRHQRTHT
GEKPYKCPECGKSFSRSDHLSKHQRTHQNKKG
```

(lower case letters are a leader sequence from Shi & Berg, Chemistry and Biology 1, 83–89. (1995). The optimal binding sequence for the Sp-1 consensus sequence is 5'GGGGCGGGG3' (SEQ ID NO:222). Other suitable ZFPs are described below.

There are a number of substitution rules that assist rational design of some zinc finger proteins. For example, ZFP DNA-binding domains can be designed and/or selected to recognize a particular target site as described in co-owned WO 00/42219; WO 00/41566; and U.S. Ser. No. 09/444,241 filed Nov. 19, 1999; Ser. No. 09/535,088 filed Mar. 23, 2000; as well as U.S. Pat. Nos. 5,789,538; 6,007,408; 6,013,453; 6,140,081; and 6,140,466; and PCT publications WO 95/19431, WO 98/54311, WO 00/23464 and WO 00/27878. In one embodiment, a target site for a zinc finger DNA-binding domain is identified according to site selection rules disclosed in co-owned WO 00/42219. In a preferred embodiment, a ZFP is selected as described in co-owned U.S. Ser. No. 09/716,637, filed Nov. 20, 2000, titled "Iterative Optimization in the Design of Binding Proteins." See also WO 96/06166; Desjarlais & Berg, PNAS 90, 2256–2260 (1993); Choo & Klug, PNAS 91, 11163–11167 (1994); Desjarlais & Berg, PNAS 89, 7345–7349 (1992); Jamieson et al., Biochemistry 33:5689–5695 (1994); and Choo et al., WO 98/53057, WO 98/53058; WO 98/53059; WO 98/53060.

Many of these rules are supported by site-directed mutagenesis of the three-finger domain of the ubiquitous transcription factor, Sp-1 (Desjarlais and Berg, 1992; 1993). One of these rules is that a 5' G in a DNA triplet can be bound by a zinc finger incorporating arginine at position 6 of the recognition helix. Another substitution rule is that a G in the middle of a subsite can be recognized by including a histidine residue at position 3 of a zinc finger. A further substitution rule is that asparagine can be incorporated to recognize A in the middle of a triplet, aspartic acid, glutamic acid, serine or threonine can be incorporated to recognize C in the middle of a triplet, and amino acids with small side chains such as alanine can be incorporated to recognize T in the middle of a triplet. A further substitution rule is that the 3' base of a triplet subsite can be recognized by incorporating the following amino acids at position -1 of the recognition helix: arginine to recognize G, glutamine to recognize A, glutamic acid (or aspartic acid) to recognize C, and threonine to recognize T. Although these substitution rules are useful in designing zinc finger proteins they do not take into account all possible target sites. Furthermore, the assumption underlying the rules, namely that a particular amino acid in a zinc finger is responsible for binding to a particular base in a subsite is only approximate. Context-dependent interactions between proximate amino acids in a finger or binding of multiple amino acids to a single base or vice versa can cause variation of the binding specificities predicted by the existing substitution rules. Accordingly, in certain embodiments, a ZFP DNA-binding domain of predetermined specificity is obtained according to the methods described in co-owned U.S. Ser. No. 09/716,637, filed Nov. 20, 2000, titled "Iterative Optimization in the Design of Binding Proteins."

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., PNAS 92:344–348 (1995); Jamieson et al., Biochemistry 33:5689–5695 (1994); Rebar & Pabo, Science 263:671–673 (1994); Choo & Klug, PNAS 91:11163–11167 (1994); Choo & Klug, PNAS 91: 11168–11172 (1994); Desjarlais & Berg, PNAS 90:2256–2260 (1993); Desjarlais & Berg, PNAS 89:7345–7349 (1992); Pomerantz et al., Science 267:93–96 (1995); Pomerantz et al., PNAS 92:9752–9756 (1995); and Liu et al., PNAS 94:5525–5530 (1997); Griesman & Pabo, Science 275:657–661 (1997); Desjarlais & Berg, PNAS 91:11–99–11103 (1994)).

In certain preferred embodiments, the binding specificity of a DNA-binding domain (e.g., a ZFP DNA-binding domain) is determined by identifying accessible regions in the sequence in question (e.g., in cellular chromatin). Accessible regions can be determined as described in co-owned U.S. patent application Ser. No. 60/228,556 entitled "Databases of Accessible Region Sequences; Methods of Preparation and Use Thereof," filed Aug. 28, 2000, the disclosure of which is hereby incorporated by reference herein. See also Example 1. A DNA-binding domain is then designed and/or selected as described herein to bind to a target site within the accessible region VI. Production of Zinc Finger Proteins A. Synthesis and Cloning ZFP polypeptides and nucleic acids encoding the same can be made using routine techniques in the field of recombinant genetics. Basic texts disclosing general methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). In addition, nucleic acids less than about 100 bases can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.). Similarly, peptides can be custom ordered from any of a variety of sources, such as PeptidoGenic (pkim@ccnet.com), HTI Bio-products, inc. (http://www.htibio.com), BMA Biomedicals Ltd (U.K.), Bio.Synthesis, Inc.

Oligonucleotides can be chemically synthesized according to the solid phase phosphoramidite triester method first described by Beaucage & Caruthers, Tetrahedron Letts. 22:1859–1862 (1981), using an automated synthesizer, as described in Van Devanter et al., Nucleic Acids Res. 12:6159–6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., Gene 16:21–26 (1981).

Two alternative methods are typically used to create the coding sequences required to express newly designed DNA-binding peptides. One protocol is a PCR-based assembly procedure that utilizes six overlapping oligonucleotides. Three oligonucleotides correspond to "universal" sequences that encode portions of the DNA-binding domain between the recognition helices. These oligonucleotides typically remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the above-mentioned protocol. Oligonucleotides complementary to oligos 1 and 6 are engineered to leave overhanging sequences specific for the restriction sites used in cloning into the vector of choice in the following step. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created using conventional site-directed mutagenesis methods.

Both assembly methods require that the resulting fragment encoding the newly designed ZFP be ligated into a vector. Ultimately, the ZFP-encoding sequence is cloned into an expression vector. Expression vectors that are commonly utilized include, but are not limited to, a modified pMAL-c2 bacterial expression vector (New England BioLabs, Beverly, Mass.) or an eukaryotic expression vector, pcDNA (Promega, Madison, Wis.). The final constructs are verified by sequence analysis.

Any suitable method of protein purification known to those of skill in the art can be used to purify ZFPs (see, Ausubel, supra, Sambrook, supra). In addition, any suitable host can be used for expression, e.g., bacterial cells, insect cells, yeast cells, mammalian cells, and the like.

Expression of a zinc finger protein fused to a maltose binding protein (MBP-ZFP) in bacterial strain JM109 allows for straightforward purification through an amylose column (New England BioLabs, Beverly, Mass.). High expression levels of the zinc finger chimeric protein can be obtained by induction with IPTG since the MBP-ZFP fusion in the pMal-c2 expression plasmid is under the control of the tac promoter (New England BioLabs, Beverly, Mass.). Bacteria containing the MBP-ZFP fusion plasmids are inoculated into 2×YT medium containing 10 µM ZnCl2, 0.02% glucose, plus 50 µg/ml ampicillin and shaken at 37° C. At mid-exponential growth IPTG is added to 0.3 mM and the cultures are allowed to shake. After 3 hours the bacteria are harvested by centrifugation, disrupted by sonication or by passage through a french pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 µM ZnCl2, then eluted with maltose in essentially the same buffer (purification is based on a standard protocol from New England BioLabs. Purified proteins are quantitated and stored for biochemical analysis.

The dissociation constant of a purified protein, e.g., Kd, is typically characterized via electrophoretic mobility shift assays (EMSA) (Buratowski & Chodosh, in Current Protocols in Molecular Biology pp. 12.2.1–12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2×9 bp +intervening bases for a six finger ZFP. The annealed oligonucleotide targets possess a 1 base 5' overhang which allows for efficient labeling of the target with T4 phage polynucleotide kinase. For the assay the target is added at a concentration of 1 nM or lower (the actual concentration is kept at least 10-fold lower than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM MgCl2, 0.1 mM ZnCl2, 5 mM DTT, 10% glycerol, 0.02% BSA.

The equilibrated reactions are loaded onto a 10% polyacrylamide gel, which has been pre-run for 45 min in Tris/glycine buffer, then bound and unbound labeled target is resolved by electrophoresis at 150V. Alternatively, 10–20% gradient Tris-HCl gels, containing a 4% polyacrylamide stacking gel, can be used. The dried gels are visualized by autoradiography or phosphorimaging and the apparent Kd is determined by calculating the protein concentration that yields half-maximal binding.

The assays can also include a determination of the active fraction in the protein preparations. Active fraction is determined by stoichiometric gel shifts in which protein is titrated against a high concentration of target DNA. Titrations are done at 100, 50, and 25% of target (usually at micromolar levels).

B. Phage Display

The technique of phage display provides a largely empirical means of generating zinc finger proteins with a desired target specificity (see e.g., Rebar, U.S. Pat. No. 5,789,538; Choo et al., WO 96/06166; Barbas et al., WO 95/19431 and WO 98/543111; Jamieson et al., supra). The method can be used in conjunction with, or as an alternative to rational design. The method involves the generation of diverse libraries of mutagenized zinc finger proteins, followed by the isolation of proteins with desired DNA-binding properties using affinity selection methods. To use this method, the experimenter typically proceeds as follows. First, a gene for a zinc finger protein is mutagenized to introduce diversity into regions important for binding specificity and/or affinity. In a typical application, this is accomplished via randomization of a single finger at positions −1, +2, +3, and +6, and sometimes accessory positions such as +1, +5, +8 and +10. Next, the mutagenized gene is cloned into a phage or phagemid vector as a fusion with gene III of a filamentous phage, which encodes the coat protein pIII. The zinc finger gene is inserted between segments of gene III encoding the membrane export signal peptide and the remainder of pIII, so that the zinc finger protein is expressed as an amino-terminal fusion with pIII or in the mature, processed protein. When using phagemid vectors, the mutagenized zinc finger gene may also be fused to a truncated version of gene III encoding, minimally, the C-terminal region required for assembly of pIII into the phage particle. The resultant vector library is transformed into $E.\ coli$ and used to produce filamentous phage which express variant zinc finger proteins on their surface as fusions with the coat protein pIII. If a phagemid vector is used, then the this step requires superinfection with helper phage. The phage library is then incubated with a target DNA site, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which disrupt zinc finger—DNA binding. Recovered phage are used to infect fresh $E.\ coli.$, which is then amplified and used to produce a new batch of phage particles. Selection and amplification are then repeated as many times as is necessary to enrich the phage pool for tight binders such that these may be identified using sequencing and/or screening methods. Although the method is illustrated for pIII fusions, analogous principles can be used to screen ZFP variants as pVIII fusions.

In certain embodiments, the sequence bound by a particular zinc finger protein is determined by conducting binding reactions (see, e.g., conditions for determination of Kd, supra) between the protein and a pool of randomized double-stranded oligonucleotide sequences. The binding reaction is analyzed by an electrophoretic mobility shift assay (EMSA), in which protein-DNA complexes undergo retarded migration in a gel and can be separated from unbound nucleic acid. Oligonucleotides which have bound the finger are purified from the gel and amplified, for example, by a polymerase chain reaction. The selection (i.e. binding reaction and EMSA analysis) is then repeated as many times as desired, with the selected oligonucleotide sequences. In this way, the binding specificity of a zinc finger protein having a particular amino acid sequence is determined.

C. Regulatory Domains

Zinc finger proteins are often expressed with an exogenous domain (or functional fragment thereof) as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is a KRAB repression domain from the human KOX-1 protein (Thiesen et al., New Biologist 2, 363–374 (1990); Margolin et al., Proc. Natl. Acad. Sci. USA 91, 4509–4513 (1994); Pengue et al., Nucl. Acids Res. 22:2908–2914 (1994); Witzgall et al., Proc. Natl. Acad. Sci. USA 91, 4514–4518 (1994). Preferred domains for achieving activation include the HSV VP16 activation domain (see, e.g., Hagmann et al., J. Virol. 71, 5952–5962 (1997)) nuclear hormone receptors (see, e.g., Torchia et al., Curr. Opin. Cell. Biol. 10:373–383 (1998)); the p65 subunit of nuclear factor kappa B (Bitko & Barik, J. Virol. 72:5610–5618 (1998) and Doyle & Hunt, Neuroreport 8:2937–2942 (1997)); Liu et al., Cancer Gene Ther. 5:3–28 (1998)), or artificial chimeric functional domains such as VP64 (Seifpal et al., EMBO J. 11, 4961–4968 (1992)).

The identification of novel sequences and accessible regions (e.g., DNase I hypersensitive sites) in VEGF genes allows for the design of fusion molecules which facilitate modulation of angiogenesis. Thus, in certain embodiments, the compositions and methods disclosed herein involve fusions between a DNA-binding domain specifically targeted to one or more regulatory regions of a VEGF gene and a functional (e.g., repression or activation) domain (or a polynucleotide encoding such a fusion). In this way, the repression or activation domain is brought into proximity with a sequence in the VEGF gene that is bound by the DNA-binding domain. The transcriptional regulatory function of the functional domain is then able to act on VEGF regulatory sequences.

In additional embodiments, targeted remodeling of chromatin, as disclosed in co-owned U.S. patent application entitled "Targeted Modification of Chromatin Structure," can be used to generate one or more sites in cellular chromatin that are accessible to the binding of a DNA binding molecule.

Fusion molecules are constructed by methods of cloning and biochemical conjugation that are well-known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) Proc. Natl. Acad. Sci. USA 97:3930–3935.

The fusion molecules disclosed herein comprise a DNA-binding domain which binds to a target site in a VEGF gene. In certain embodiments, the target site is present in an accessible region of cellular chromatin. Accessible regions can be determined as described, for example, in co-owned U.S. patent application Ser. No. 60/228,556. If the target site is not present in an accessible region of cellular chromatin, one or more accessible regions can be generated as described in co-owned U.S. patent application entitled "Targeted Modification of Chromatin Structure." In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) Cell 48:261–270; Pina et al. (1990) Cell 60:719–731; and Cirillo et al. (1998) EMBO J. 17:244–254.

For such applications, the fusion molecule is typically formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

An exemplary functional domain for fusing with a DNA-binding domain such as, for example, a ZFP, to be used for repressing expression of a gene is a KRAB repression domain from the human KOX-1 protein (see, e.g., Thiesen et al., New Biologist 2, 363–374 (1990); Margolin et al., Proc. Natl. Acad. Sci. USA 91, 4509–4513 (1994); Pengue et al., Nucl. Acids Res. 22:2908–2914 (1994); Witzgall et al., Proc. Natl. Acad. Sci. USA 91, 4514–4518 (1994). Another suitable repression domain is methyl binding domain protein 2B (MBD-2B) (see, also Hendrich et al. (1999) Mamm Genome 10:906–912 for description of MBD proteins). Another useful repression domain is that associated with the v-ErbA protein. See, for example, Damm, et al. (1989) Nature 339:593–597; Evans (1989) Int. J. Cancer Suppl. 4:26–28; Pain et al. (1990) New Biol. 2:284–294; Sap et al. (1989) Nature 340:242–244; Zenke et al. (1988) Cell 52:107–119; and Zenke et al. (1990) Cell 61:1035–1049.

Suitable domains for achieving activation include the HSV VP16 activation domain (see, e.g., Hagmann et al., J. Virol. 71, 5952–5962 (1997)) nuclear hormone receptors (see, e.g., Torchia et al., Curr. Opin. Cell. Biol. 10:373–383 (1998)); the p65 subunit of nuclear factor kappa B (Bitko & Barik, J. Virol. 72:5610–5618 (1998) and Doyle & Hunt, Neuroreport 8:2937–2942 (1997)); Liu et al., Cancer Gene Ther. 5:3–28 (1998)), or artificial chimeric functional domains such as VP64 (Seifpal et al., EMBO J. 11, 4961–4968 (1992)).

Additional exemplary activation domains include, but are not limited to, VP16, VP64, p300, CBP, PCAF, SRC1 PvALF, AtHD2A and ERF-2. See, for example, Robyr et al. (2000) Mol. Endocrinol. 14:329–347; Collingwood et al. (1999) J. Mol. Endocrinol. 23:255–275; Leo et al. (2000) Gene 245:1–11; Manteuffel-Cymborowska (1999) Acta Biochim. Pol. 46:77–89; McKenna et al. (1999) J. Steroid Biochem. Mol. Biol. 69:3–12; Malik et al. (2000) Trends Biochem. Sci. 25:277–283; and Lemon et al. (1999) Curr. Opin. Genet. Dev. 9:499–504. Additional exemplary activation domains include, but not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21–29; Okanami et al. (1996) Genes Cells 1:87–99; Goff et al. (1991) Genes Dev. 5:298–309; Cho et al. (1999) Plant Mol. Biol. 40:419–429; Ulmason et al. (1999) Proc. Natl. Acad. Sci. USA 96:5844–5849; Sprenger-Haussels et al. (2000) Plant J. 22:1–8; Gong et al. (1999) Plant Mol. Biol. 41:33–44; and Hobo et al. (1999) Proc. Natl. Acad. Sci. USA 96:15,348–15,353.

Additional exemplary repression domains include, but are not limited to, KRAB, SID, MBD2, MBD3, members of the DNMT family (e.g., DNMT1, DNMT3A, DNMT3B), Rb, and MeCP2. See, for example, Bird et al. (1999) Cell 99:451–454; Tyler et al. (1999) Cell 99:443–446; Knoepfler et al. (1999) Cell 99:447–450; and Robertson et al. (2000) Nature Genet. 25:338–342. Additional exemplary repression domains include, but are not limited to, ROM2 and AtHD2A. See, for example, Chem et al. (1996) Plant Cell 8:305–321; and Wu et al. (2000) Plant J. 22:19–27.

Additional functional domains are disclosed, for example, in co-owned WO 00/41566.

D. Expression Vectors

The nucleic acid encoding the ZFP of choice is typically cloned into intermediate vectors for transformation into prokaryotic or eukaryotic cells for replication and/or expression, e.g., for determination of Kd. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994). Bacterial expression systems for expressing the ZFP are available in, e.g., *E. coli, Bacillus sp.*, and *Salmonella* (Palva et al., Gene 22:229–235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491–496 (1998); Wang et al., Gene Ther. 4:432–441 (1997); Neering et al., Blood 88:1147–1155 (1996); and Rendahl et al., Nat. Biotechnol. 16:757–761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and exogenous spliced intronic signals.

The particular expression vector used to transport the genetic information into the cell is selected with regard to the intended use of the ZFP. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., J. Biol. Chem. 264:17619–17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349–351 (1977); Clark-Curtiss & Curtiss, Methods in Enzymology 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

VII. Assays

Once a ZFP has been designed and prepared according to the procedures just set forth, an initial assessment of the activity of the designed ZFP is undertaken. ZFP proteins showing the ability to modulate the expression of a gene of interest can then be further assayed for more specific activities depending upon the particular application for which the ZFPs have been designed. Thus, for example, the ZFPs provided herein can be initially assayed for their ability to modulate VEGF expression. More specific assays of the ability of the ZFP to modulate angiogenesis and/or to treat ischemia are then typically undertaken. A description of these more specific assays are set forth infra in section IX.

The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, Ca2+); cytokine and hormone production levels; and neovascularization, using, e.g., immunoassays (e.g., ELISA and immunohistochemical assays with antibodies), hybridization assays (e.g., RNase protection, Northerns, in situ hybridization, oligonucleotide array studies), colorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to untreated control samples, to examine the extent of modulation. As described above, for regulation of endogenous gene expression, the ZFP typically has a Kd of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as tumor growth, wound healing, neovascularization, hormone release, transcriptional changes to both known and uncharacterized genetic markers (e.g., Northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with a vector lacking ZFP-encoding sequences or a vector encoding an unrelated ZFP that is targeted to another gene.

In another embodiment, ZFP regulation of endogenous gene expression is determined in vitro by measuring the level of target gene mRNA expression. The level of gene expression is measured using amplification, e.g., using PCR, LCR, or hybridization assays, e.g., Northern hybridization, dot blotting and RNase protection. The use of quantitative RT-PCR techniques (i.e., the so-called TaqMan assays) can also be utilized to quantitate the level of transcript. The level of protein or mRNA is detected using directly or indirectly labeled detection agents, e.g., fluorescently or radioactively labeled nucleic acids, radioactively or enzymatically labeled antibodies, and the like, as described herein. Such methods are also described in U.S. Pat No. 5,210,015 to Gelfand, U.S. Pat. No. 5,538,848 to Livak, et al., and U.S. Pat. No. 5,863,736 to Haaland, as well as Heid, C. A., et al., Genome Research, 6:986–994 (1996); Gibson, U. E. M, et al., Genome Research 6:995–1001 (1996); Holland, P. M., et al., Proc. Natl. Acad. Sci. USA 88:7276–7280, (1991); and Livak, K. J., et al., PCR Methods and Applications 357–362 (1995), each of which is incorporated by reference in its entirety.

Alternatively, a reporter gene system can be devised using a VEGF gene promoter operably linked to a reporter gene such as luciferase, green fluorescent protein, CAT, or β-gal. The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining genes such as VEGF involved in tumor support via neovascularization. In this assay, cultured tumor cells expressing the ZFP of choice are injected subcutaneously into an immune compromised mouse such as an athymic mouse, an irradiated mouse, or a SCID mouse. After a suitable length of time, preferably 4–8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used for examining regulation of VEGF gene expression in vivo. Transgenic animals typically express the ZFP of choice. Alternatively, animals that transiently express the ZFP of choice, or to which the ZFP has been administered in a delivery vehicle, can be used. Regulation of endogenous gene expression is tested using any one of the assays described herein.

VIII. Pharmaceutical Compositions

The ZFPs provided herein, and more typically the nucleic acids encoding them, can optionally be formulated with a pharmaceutically acceptable carrier as a pharmaceutical composition.

A. Nucleic Acid Based Compositions

Conventional viral and non-viral based gene transfer methods can be used to introduce nucleic acids encoding the present ZFPs in mammalian cells or target tissues. Such methods can be used to administer nucleic acids encoding ZFPs to cells in vitro. In some instances, the nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808–813 (1992); Nabel & Felgner, TIBTECH 11:211–217 (1993); Mitani & Caskey, TIBTECH 11:162–166 (1993); Dillon, TIBTECH 11: 167–175 (1993); Miller, Nature 357:455–460 (1992); Van Brunt, Biotechnology 6(10):1149–1154 (1988); Vigne, Restorative Neurology and Neuroscience 8:35–36 (1995); Kremer & Perricaudet, British Medical Bulletin 51(1):31–44 (1995); Haddada et al., in Current Topics in Microbiology and Immunology Doerfler and Bohm (eds) (1995); and Yu et al., Gene Therapy 1:13–26 (1994).

Methods of non-viral delivery of nucleic acids encoding the ZFPs provided herein include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404–410 (1995); Blaese et al., Cancer Gene Ther. 2:291–297 (1995); Behr et al., Bioconjugate Chem. 5:382–389 (1994); Remy et al., Bioconjugate Chem. 5:647–654 (1994); Gao et al., Gene Therapy 2:710–722 (1995); Ahmad et al., Cancer Res. 52:4817–4820 (1992); U.S. Pat. Nos. 4,186,183, 4,217,344, 4,235,871, 4,261,975, 4,485,054, 4,501,728, 4,774,085, 4,837,028, and 4,946, 787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs can include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system can therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731–2739 (1992); Johann et al., J. Virol. 66:1635–1640 (1992); Sommerfelt et al., Virol. 176:58–59 (1990); Wilson et al., J. Virol. 63:2374–2378 (1989); Miller et al., J. Virol. 65:2220–2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38–47 (1987); U.S. Pat. No. 4,797,368; WO 93/24641; Kotin, Human Gene Therapy 5:793–801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251–3260 (1985); Tratschin, et al., Mol. Cell. Biol. 4:2072–2081 (1984); Hermonat & Muzyczka, PNAS 81:6466–6470 (1984); and Samulski et al., J. Virol. 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., Blood 85:3048–305 (1995); Kohn et al., Nat. Med. 1:1017–102 (1995); Malech et al., PNAS 94:22 12133–12138 (1997)). PA317/pLASN was the first therapeutic vector used in a gene therapy trial. (Blaese et al., Science 270:475–480 (1995)). Transduction efficiencies of 50% or greater have been observed for MFG-S packaged vectors. (Ellem et al., Immunol Immunother. 44(1):10–20 (1997); Dranoff et al., Hum. Gene Ther. 1:111–2 (1997).

Recombinant adeno-associated virus vectors (rAAV) is another alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702–3 (1998), Kearns et al., Gene Ther. 9:748–55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083–9 (1998)). Additional examples of the use of adenovirus vectors for gene transfer in clinical trials include Rosenecker et al., Infection 24:1 5–10 (1996); Sterman et al., Hum. Gene Ther. 9:7 1083–1089 (1998); Welsh et al., Hum. Gene Ther. 2:205–18 (1995); Alvarez et al., Hum. Gene Ther. 5:597–613 (1997); Topfet al., Gene Ther. 5:507–513 (1998); Sterman et al., Hum. Gene Ther. 7:1083–1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some instances, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., J. Exp. Med. 176:1693–1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., J. Exp. Med. 176:1693–1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below (see, e.g., Remington's Pharmaceutical Sciences, 17th ed., 1989).

B. Protein Compositions

An important factor in the administration of polypeptide compounds, such as the present ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629–634 (1996)). Another subsequence, the h (hydrophobic) domain of signal peptides, was found to have similar cell membrane translocation characteristics (see, e.g., Lin et al., J. Biol. Chem. 270:14255–14258 (1995)).

Examples of peptide sequences which can be linked to a ZFP, for facilitating uptake of ZFP into cells, include, but are not limited to: an 11 amino acid peptide of the tat protein of HIV; a 20 residue peptide sequence which corresponds to amino acids 84–103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223–233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., J. Biol. Chem., 268:3334–3341 (1993); Perelle et al., Infect. Immun., 61:5147–5156 (1993); Stenmark et al., J. Cell Biol. 113:1025–1032 (1991); Donnelly et al., PNAS 90:3530–3534 (1993); Carbonetti et al., Abstr. Annu. Meet. Am. Soc. Microbiol. 95:295 (1995); Sebo et al., Infect. Immun. 63:3851–3857 (1995); Klimpel et al., PNAS U.S.A. 89:10277–10281 (1992); and Novak et al., J. Biol. Chem. 267:17186–17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP. The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., PNAS 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, Biochim. Biophys. Acta 443:629–634 (1976); Fraley, et al., PNAS 76:3348–3352 (1979); Hope et al., Biochim. Biophys. Acta 812:55–65 (1985); Mayer et al., Biochim. Biophys. Acta 858:161–168 (1986); Williams et al., PNAS 85:242–246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In some instances, liposomes are targeted using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265:16337–16342 (1990) and Leonetti et al., PNAS 87:2448–2451 (1990).

C. Dosage

For therapeutic applications of ZFPs, the dose administered to a patient should be sufficient to effect a beneficial therapeutic response in the patient over time. The dose will be determined by the efficacy and Kd of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

In determining the effective amount of the ZFP to be administered in the treatment or prophylaxis of disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

D. Compositions and Modes of Administration

1. General

ZFPs and the nucleic acids encoding the ZFPs can be administered directly to a patient for modulation of gene expression and for therapeutic or prophylactic applications such as those described infra. In general, and in view of the discussion herein, phrases referring to introducing a ZFP into an animal or patient can mean that a ZFP or ZFP fusion protein is introduced and/or that a nucleic acid encoding a ZFP of ZFP fusion protein is introduced in a form that can be expressed in the animal. For example, as described in greater detail in the following section, the ZFPs and/or nucleic acids can be used to modulate angiogenesis and in the treatment of ischemia.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions (see, e.g., Remington's Pharmaceutical Sciences, 17th ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the disclosed methods, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

2. Exemplary Angiogenesis Delivery Options

A variety of delivery options are available for the delivery of the pharmaceutical compositions provided herein so as to modulate angiogenesis and thus, for example, the treatment of ischemic conditions. Depending upon the particular application, the compositions can be targeted to specific areas or tissues of a subject. For example, in some methods, one delivers compositions to specific regions of the heart to treat various disorders such as ischemia. Other treatments, in contrast, involve administering the composition in a general manner without seeking to target delivery to specific regions.

A number of approaches can be utilized to localize the delivery of agents to particular regions. Certain of these methods involve delivery to the body lumen or to a tissue (see, e.g., U.S. Pat. Nos. 5,941,868; 6,067,988; 6,050,986; and 5,997,509; as well as PCT Publications WO 00/25850; WO 00/04928; 99/59666; and 99/38559). Delivery can also be effectuated by intramyocardial injection or administration. Examples of such approaches include those discussed in U.S. Pat. Nos. 6,086,582; 6,045,565; 6,056,969; and 5,997,525; and in PCT Publications WO 00/16848; WO 00/18462; WO 00/24452; WO 99/49773 and WO 99/49926. Other options for local delivery include intrapericardial injection (see, e.g., U.S. Pat. Nos. 5,931,810; 5,968,010; and 5,972,013) and perivascular delivery. Various transmyocardial revascular (TMR) channel delivery approaches can be utilized as well. Many of these methods utilize a laser to conduct the revascularization. A discussion of such approaches is set forth in U.S. Pat. Nos. 5,925,012; 5,976,164; 5,993,443; and 5,999,678, for example. Other options include intraarterial and/or intracoronary delivery, for example coronary artery injection (see, e.g., WO 99/29251) and endovascular administration (see, e.g., U.S. Pat. Nos. 6,001,350; 6,066,123; and 6,048,332; and PCT Publications WO 99/31982; WO 99/33500; and WO 00/15285). Thus, for example, one can inject a composition as described herein directly into the myocardium.

Additional options for the delivery of compositions to modulate angiogenesis include systemic administration using intravenous or subcutaneous administration, cardiac chamber access (see, e.g., U.S. Pat. No. 5,924,424) and tissue engineering (U.S. Pat. No. 5,944,754).

Other delivery methods known by those skilled in the art include the methods disclosed in U.S. Pat. Nos. 5,698,531; 5,893,839; 5,797,870; 5,693,622; 5,674,722; 5,328,470; and 5,707,969.

IX. Applications

A. General

ZFPs that bind to the target sites disclosed herein, and nucleic acids encoding them, can be utilized in wide variety of applications, particularly applications involving the modulation of endothelial cell growth. Such methods generally involve contacting a target site of a nucleic acid within a cell or population of cells with a ZFP that has binding specificity for one of the target sites disclosed herein. Methods can be performed in vitro with cell cultures, for example, or in vivo.

Certain methods are performed such that modulation involves activation of one or more VEGF genes. Such methods are useful when generation of additional endothelial cells is desired, such as in promoting angiogenesis to relieve some type of arterial or vascular blockage or in activating lymphogenesis or myelopoiesis. Other methods can be conducted to repress endothelial cell growth when such repression provides a beneficial effect, such as inhibiting further vascular development in the region of a tumor for example.

The ZFPs can also be used for non-therapeutic applications such as in screening methods to identify agents that activate or repress expression of a VEGF gene or to detect target nucleic acids containing the target sequences.

B. Therapeutic Applications

1. Modulation of Angiogenesis

The ZFPs provided herein and the nucleic acids encoding them such as in the pharmaceutical compositions described supra can be utilized to activate expression of VEGF genes such that the resulting VEGF proteins can act as growth factors in activating endothelial cell growth, both in cell cultures (i.e., in in vitro applications) and in vivo. Such activation can promote useful angiogenesis in which new blood vessels and capillaries are formed; activation can also promote somatic growth and vascular development and differentiation. Hence, certain methods for promoting angiogenesis involve introducing a ZFP into an animal. Binding of the ZFP bearing an activation domain to a gene that modulates angiogenesis can enhance the process of angiogenesis. Certain methods involve the use of ZFPs such as described herein to bind to target sites in the VEGF genes. An activation domain fused to the ZFP activates the expression of one or more VEGF genes.

The ZFPs and nucleic acids can also be useful in bone repair, promoting wound healing and in speeding the healing of gastric and/or duodenal ulcers. The ZFPs and nucleic acids can also be utilized to promote development of the corpus luteum and endometrium, such activation useful in initiating and/or maintaining pregnancy. In related methods, administration of the ZFPs and nucleic acids also find utility in supporting embryogenesis.

A variety of assays for assessing endothelial cell proliferation and angiogenesis are known. For example, endothelial cell proliferation assays are discussed by Ferrara and Henzel (1989) Nature 380:439–443; Gospodarowicz et al. (1989) Proc. Natl. Acad. Sci. USA, 86: 7311–7315; and Claffey et al. (1995) Biochim. Biophys. Acta. 1246:1–9. The ability of the ZFPs and/or nucleic acids to promote angiogenesis can be evaluated, for example, in chick chorioallantoic membrane, as discussed by Leung et al. (1989) Science 246:1306–1309. Another option is to conduct assays with rat corneas, as discussed by Rastinejad et al. (1989) Cell 56:345–355. Other assays are disclosed in U.S. Pat. No. 5,840,693. In addition, microscopic examination of tissue sections is disclosed in Example 4 and FIG. 9 can be used as an assay for angiogenesis. Each of these methods are accepted assays of in vivo angiogenesis and the results can also be extrapolated to other systems.

Administration of the ZFPs and/or nucleic acids encoding them can also be utilized in applications in which initiation or extension of vascularization is desirable. Examples of such applications include therapies following tissue or organ transplantation. Many applications involve relieving ischemic conditions and various types of blood flow blockage such as that resulting from atherosclerosis. For instance, certain applications involve establishing collateral circulation in tissue infarction or arterial stenosis, such as occurs in coronary heart disease. Stimulation of collateral circulation is also useful in treating deep venous thrombosis, myocardial infarcts, ischaemic limbs and/or postpartum vascular problems.

A variety of assays can be utilized to assess the ability of a ZFP to treat ischemia. For example, several models for studying ischemia are known. These include, but are not limited to, experimentally induced rat hindlimb ischemia (see, e.g., Takeshita, S. et al., Circulation (1998) 98: 1261–63; and Takeshita, S. et al. (1994) Circulation 90(#5; part II):228–234), a partially ischemic hindlimb rabbit model (see, e.g., Hopkins, S. et al., J. Vasc. Surg. (1998) 27: 886–894), and a chronic porcine myocardial ischemia model (see, e.g., Harada, K. et al., Am. J. Physiol. (1996) 270: 886–94; and Hariawala, M. et al., 1996, J. Surg. Res. 63: 77–82). Another assay includes a rabbit model of hindlimb ischemia (see, e.g., Takeshita, S. et al., 1994, Circulation 90(#5; part II):228–234).

Neovascularization is also important in fracture repair as the healing process involves formation of new blood vessels at the fracture site. Thus, the ZFP and nucleic acids can also be used in the treatment of bone fractures. Assays for measuring effects of administration are known. For example, methods for assaying for atherosclerosis are discussed in PCT Publication WO 00/25805.

Wound treatment is another general type of application in which administration of the ZFPs, nucleic acids and compositions disclosed herein find utility. The ZFPs and nucleic acids can be used to treat significant wounds such as ulcers, pressure sores and venous ulcers and burns. Examples of such ulcers are those experienced by diabetic patients. An example of the use of ZFP fusions to promote wound healing is provided in Example 4 and FIG. 9.

The ZFPs and nucleic acids provided herein can also be utilized in diverse surgical applications. For instance, another use is in preparation of a burn or trauma site to receive a skin graft. Similarly, the compositions can be used to promote the formation of endothelial cells in vascular graft surgery. In such surgeries, compositions can be introduced at the site of the graft before or during surgery. The ZFPs and nucleic acids can be utilized in plastic surgery, especially in reconstruction of areas burned or otherwise traumatized. Another surgical setting in which the compositions can be utilized is in post-operative wound healing following balloon angioplasty as such procedures involve removal and damage to endothelial cells. Treatment in such instances can utilize compositions containing the ZFP or nucleic acids in combination with a parenteral carrier.

The ZFPs and nucleic acids encoding them also find use in general surgery and in treating and repairing cuts and lacerations. In such applications, the ZFPs and nucleic acids are used to prevent wounds from becoming infected. When utilized in topical wound healing, in some instances the ZFPs or nucleic acids can be administered topically as part of a solution, spray, cream, gel, ointment or dry powder directly to the site being treated. Slow release compositions can also be effective in treating certain types of wounds.

Wound healing assays that can be utilized to asses the utility of various compositions are discussed, for example, by Schilling et al. (1959) Surgery 46:702–710; and Hunt et al. (1967) Surgery 114:302–307. Another wound healing assay is disclosed in Example 4.

The ZFPs and nucleic acids provided herein can also be utilized in promoting the growth of lymphatic endothelial cells and lymphatic vessels. Additionally, the compositions can be used to stimulate lymphangiogenesis. Thus, for example, the compositions can be administered to promote regrowth or permeability in lymphatic vessels. This can be useful in treating organ transplant patients and in mitigating the loss of axillary lymphatic vessels that often accompanies surgery and cancer treatments. Other related applications include treatment of lymphatic vessel occlusions (e.g., elephantiasis) and lymphangiomas.

Activation of myelopoiesis can also be achieved with certain of the present ZFPs and nucleic acids. For example, the compositions can be used to promote the growth of neutrophilic granulocytes. Such treatments can be useful in treating patients suffering from diseases such as granulocytopenia, for example. The production of neutrophilic granulocytes can be monitored by established microscopic and macroscopic methods.

Previous experiments showed that the introduction of cDNA encoding a single mouse VEGF164 isoform in mice led to the formation of permeable vessels which were spontaneously hemorrhagic (Pettersson, A. et al., 2000, Lab. Invest. 80:99–115). Briefly, an adenoviral vector encoding murine VEGF164 was injected subcutaneously in the ears of mice. VEGF164 was shown to induce hemorrhage and extravasation of intravascular dye in this mouse ear model. When compared to mouse ears similarly treated with an adenovirus encoding murine VEGF164, the ZFP-induced neovasculature was not spontaneously hemorrhagic and was not permeable to Evans Blue dye infusion (see Example 6).

2. Repression of VEGF Gene Expression

The compositions provided herein can also be utilized to repress expression of VEGF genes in a variety of therapeutic applications. One common application is to reduce or inhibit angiogenesis to particular cells or tissues which for therapeutic reasons one wants to destroy. Often such methods involve administration of compositions to prevent angiogenic events associated with pathological processes such as tumor growth and metastasis. Other pathological processes associated with increased angiogenesis, particularly in the proliferation of the microvascular system, include diabetic retinopathy, psoriasis and various arthropathies. Thus, certain of the present compositions can be utilized to treat these processes.

C. Non-Therapeutic Applications

The ZFPs and the nucleic acids encoding them can also be utilized in various non-therapeutic applications. One such application involves screening to identify new agents capable of modulating angiogenesis. In particular, the ZFPs can be used to identify agents able to modulate gene expression, such as the expression of VEGF genes. Such methods generally involve contacting a cell or population of cells with a ZFP that binds to one of the target sites listed in Tables 2–3 to either activate or repress expression of one or more VEGF genes. The cell(s) are also contacted with a test agent. The level of expression of a VEGF gene is then determined and compared with a baseline level of expression. A statistically significant difference in the expression level of the VEGF gene in the test cell(s) with the baseline level indicates that the test agent is a potential modulator of the expression of the VEGF gene. For example, if the ZFP activates expression of the VEGF gene, and level of expression in the test cell(s) is lower than the baseline level, then the evidence indicates that the test agent is a repressor of expression of the VEGF gene. On the other hand, if the ZFP represses expression of the VEGF gene, then test agents can be screened for potential activators that are able to relieve the repression caused by the ZFP. The method can be varied to introduce a nucleic acid encoding the ZFP, provided the nucleic acid includes the necessary regulatory sequences for expression in the cells being utilized in the assay. Such methods can be used to identify agents that interact with the ZFP potentially increasing or decreasing its binding and/or agents capable of binding elsewhere on the gene, thereby providing either a synergistic or antagonistic effect.

The baseline level of expression refers generally to a value (or range of values) against which an experimental or determined value is compared. Typically, the baseline value is a value determined for a control cell or individual treated in parallel and under similar conditions with the cell or individual being tested. The baseline value can also be a statistical value (e.g., a mean or average) established for a population of control cells or individuals. In cellular assays such as those just described, often the test cell is contacted with a ZFP or expresses a ZFP, while the control does not.

A difference is typically considered to be statistically significant when the difference is greater then the level of experimental error. Such a difference is also statistically significant if the probability of the observed difference occurring by chance (the p-value) is less then some predetermined level. Thus, a statistically significant difference can refer to a p-value that is <0.005, preferably <0.01, and most preferably <0.001.

In other applications, ZFPs are used in diagnostic methods for sequence specific detection of target nucleic acid in a sample that includes one of the target sites provided herein. As an example, ZFPs can be used to detect the presence of particular mRNA species or cDNA in a complex mixtures of mRNAs or cDNAs that includes the target site. Thus, the ZFPs can be used to quantify copy number of VEGF genes in a sample.

A suitable format for performing diagnostic assays employs ZFPs linked to a domain that allows immobilization of the ZFP on an ELISA plate. The immobilized ZFP is contacted with a sample suspected of containing a target nucleic acid under conditions in which binding can occur. Typically, nucleic acids in the sample are labeled (e.g., in the course of PCR amplification). Alternatively, unlabeled probes can be detected using a second labeled probe. After washing, bound-labeled nucleic acids are detected.

The following examples are provided solely to illustrate in greater detail particular aspects of the disclosed methods and compositions and should not be construed to be limiting in any way.

EXAMPLE 1

Regulation of Human VEGF Genes Using a Panel of Designed Zinc Finger Fusion Proteins I. Introduction A major question in the study of gene regulation involves the mechanisms by which the cell achieves specific activation of endogenous chromosomal genes. In addressing this issue, rationally designed components of the transcriptional machinery can provide powerful tools for testing our understanding of gene regulation (Chatterjee et al. (1995) Nature 374: 820–822; Kim et al. (1997) Proc. Natl. Acad. Sci. USA 94: 3616–3620; Klages et al. (1995) Nature 374, 822–823). In particular, artificial transcription factors—targeted to novel sequences within a given locus and bearing functional domains of the experimenter's choosing—may prove especially useful since they offer the prospect of complete recapitulation of any given activation process using totally defined components. Artificial transcription factors may also provide practical benefits in areas such as medicine and biotechnology.

The DNA binding motif of choice that has emerged for achieving specific recognition of novel, desired DNA sequences are zinc fingers. These include the initially-described Cys2-His2 zinc finger, as well as additional types of zinc finger molecules such as, for example, Cys4 zinc fingers and others. See, for example, Rhodes et al. (1993) Scientific American 268: 56–65. Over the past decade, selection and design studies have demonstrated the adaptability of this motif and have yielded simple, powerful strategies for designing zinc finger proteins (ZFPs) that can bind specifically to virtually any DNA sequence. See, for example, Choo et al. (1994) Proc. Natl. Acad. Sci. USA 91: 11,163–11,167; Choo et al. (1994) Proc. Natl. Acad. Sci. USA 91: 11,168–11,172; Choo et al. (1995) Proc. Natl. Acad. Sci. USA 92: 646 (published erratum); Desjarlais et al. (1992) Proc. Natl. Acad. Sci. USA 89: 7345–7349; Desjarlais et al. (1992) Proteins 12: 101–104; Desjarlais et al. (1992) Proteins 13, 272; Desjarlais et al. (1993) Proc. Natl. Acad. Sci. USA 90: 2256–2260; Greisman et al. (1997) Science 275: 657–661; Jamieson et al. (1994) Biochemistry 33: 5689–5695; Jamieson et al. (1996) Proc. Natl. Acad. Sci. USA 93: 12,834–12,839; Liu et al. (1997) Proc. Natl. Acad. Sci. USA 94: 5525–5530; Rebar et al. (1994) Science 263: 671–673; Rebar et al. (1996) Meth. Enzymol. 267: 129–149; Segal et al. (1999) Proc. Natl. Acad. Sci. USA 96: 2758–2763. More recently, ZFPs with novel, engineered DNA sequence specificities have begun to be used as artificial transcription factors to regulate endogenous chromosomal genes. See, for example, Bartsevich et al. (2000) Mol. Pharmacol. 58: 1–10; Beerli et al. (2000) Proc. Natl. Acad. Sci. USA 97: 1495–1500; Zhang et al. (2000) J. Biol. Chem. 275: 33,850–33,860. See also co-owned PCT WO 00/41566.

The goal of this study was to identify a panel of ZFPs that would activate the endogenous gene for vascular endothelial growth factor A (VEGF-A). VEGF-A is an endothelial cell specific mitogen that is generally recognized as the key inducer of new blood vessel growth, both during embryogenesis and in adult processes such as wound healing (for recent reviews see Flamme et al. (1997) Mech. Dev. 63: 51–60; Ferrara (1999) J. Mol. Med. 77: 527–543; Yancopoulos et al. (2000) Nature 407: 242–248. Its central roles in both vasculogenesis and angiogenesis apparently necessitate that VEGF-A expression levels be controlled by exquisitely precise regulatory mechanisms. Mouse studies have highlighted VEGF-A as perhaps the sole example of a gene whose haploinsufficiency precipitates embryonic lethality (Ferrara et al. (1996) Nature 380: 439–442; Carmeliet et al. (1996) Nature 380: 435–439. Furthermore, several other studies have suggested that proper VEGF-A function requires expression of appropriate relative levels of the three major splice variants produced by this gene (Carmeliet et al., 1996 supra; Carmeliet et al. (1999) Nature Med. 5: 495–502; Grunstein et al. (2000) Mol. Cell. Biol. 20: 7282–7291). A diversity of conditions and transcription factors have been implicated as inducing VEGF-A expression (Chua et al. (1998) Free Radic. Biol. Med. 25: 891–897; Cohen et al. (1996) J. Biol. Chem. 271: 736–741; Damert et al. (1997) Biochem. J. 327: 419–423; Diaz et al. (2000) J. Biol. Chem. 275: 642–650; Ladoux et al. (1994) Biochem. Biophys. Res. Commun. 204: 794–798; Ryuto et al. (1996) J. Biol. Chem. 271: 28,220–28,228; Salimath et al. (2000) Oncogene 19: 3470–3746), of which perhaps the best characterized is the hypoxic response, mediated by HIF-1 (Levy et al. (1995) J. Biol. Chem. 270: 13,333–13,340; Liu et al. (1995) Circ. Res. 77: 638–643; Forsythe et al. (1996) Mol. Cell. Biol. 16: 4604–4613; Kimura et al. (2000a) Blood 95: 189–197). Consistent with its highly regulated nature, VEGF-A dysregulation plays a role in a variety of pathological conditions, including tumor growth, diabetic retinopathy, and ischemic heart and limb diseases. Consequently, VEGF-A would appear to provide an attractive target for both pro- and anti-angiogenic gene therapies using designed artificial transcription factors.

In this example, the inventors have made use of engineered Cys2-His2 ZFPs and a knowledge of chromosomal structure to achieve activation of the endogenous chromosomal locus containing the gene for Vascular Endothelial Growth Factor A (VEGF-A). DNAse I hypersensitivity mapping analysis was used to identify accessible regions of the VEGF-A locus. This analysis identified four distinct DNAse I-accessible regions in VEGF-A, of which three were present in the HEK293 cells used for activation studies. Next, eight novel ZFPs were designed to recognize 9-bp sequences within each of the three HEK293-specific DNAse I-accessible regions, and their DNA-binding properties were characterized. Each designed ZFP bound to its intended target with an apparent Kd of <10 nM. These zinc fingers were then linked to the VP16 transcriptional activation domain (Sadowski et al. (1988) Nature 335: 563–564), and tested for their capacity to activate transcription of both the endogenous VEGF-A gene and transiently transfected native reporter constructs containing ~3 kb of the VEGF-A promoter. The results indicate that each of the designed ZFP-VP16 fusions activates both the endogenous VEGF-A locus and the native reporter constructs. The designed ZFPs were also linked to the activation domain from the p65 subunit of NFκB (Ruben et al. (1991) Science 251: 1490–1493; published erratum appears in Science (1991) 254: 11), and tested for the capacity to activate transcription of endogenous VEGF-A both alone and in certain combinations with VP16-linked ZFPs.

This strategy has yielded eight distinct ZFPs, targeted to seven 9-bp sites, that activate VEGF-A expression. For certain ZFPs, linkage to activation domains from either VP16 or p65 provides differing levels activation, dependent on the chromosomal site that is targeted. Furthermore, when certain combinations of VP16- and p65-linked ZFPs (targeted to distinct chromosomal sites) are cotransfected, the observed VEGF-A activation is more than additive relative to the activation levels of the individual ZFPs. Finally, it is disclosed that the levels of activation achieved by these engineered transcription factors exceed VEGF-A levels attained during the hypoxic response and that the relative proportions of VEGF-A splice variants produced by this activation closely approximates those normally observed in these cells.

II. Experimental Procedures

Cell lines and cell culture. Immortalized cell lines used in these studies (HEK 293, Hep3B, and H9c2(2-1)) were obtained from the American Type Culture Collection, and human primary skeletal muscle cells were obtained from Clonetics. Each line was maintained essentially as recommended by the suppliers. Rat primary cardiac myocytes were recovered from the hearts of day 1 neonatal Wistar-Han rats (Charles River) via dissociation with a solution of 115 U/ml type II collagenase and 0.08% pancreatin. They were then purified on a discontinuous Percoll gradient, resuspended in a plating medium containing 15% serum, and plated on gelatin-coated plates for 24 hr. Cells were then maintained in a serum-free medium for 24 to 48 hrs prior to use in DNase I mapping studies.

Mapping of DNase I-accessible chromatin regions in the VEGF-A locus. Nuclei were isolated and treated with DNase I (Worthington) essentially as described by Zhang et al., supra, except that DNase I digestions were for 1.5 min at 22 oC and the concentrations of DNase I used were as indicated in the legend to FIG. 1. Genomic DNA isolation, restriction enzyme digestion, and Southern blot analysis were then performed essentially as described by Zhang et al., supra, except that enzymes and probes were as indicated in the legend to FIG. 1. See also co-owned U.S. Patent Applications Ser. Nos. 60/200,590 and 60/228,556 for additional disclosure regarding identification of accessible regions in cellular chromatin.

Assembly of ZFP-encoding polynucleotides; synthesis, purification and binding analysis of zinc finger proteins.— Genes encoding VEGF-A-targeted ZFPs were assembled, cloned and purified as previously described. See, for example, Zhang et al., supra; WO 00/41566; and WO 00/42219. Briefly, oligonucleotides encoding α-helix and β-sheet regions of each three-finger protein were assembled using PCR (FIGS. 2A and 2B), and each resultant ZFP gene was cloned into the pMal-c2 plasmid (New England Biolabs, Beverly, Mass.) as a fusion with DNA encoding the maltose binding protein. Maltose binding protein-ZFP fusions were then expressed and affinity purified using an amylose resin (New England Biolabs, Beverly, Mass.).

Binding studies were performed essentially as described (Zhang et al., supra; WO 00/41566; and WO 00/42219) except that the binding reactions contained 10 pM of labeled target site and the buffer composition was as follows: 17 mM Tris, 170 mM KCl, 1.7 mM MgCl2, 3.5 mM DTT, 0.01–0.033 mM ZnCl2, 15% glycerol, 300 µg/ml bovine serum albumin, 0.03% IGEPAL. In addition, ZFP concentrations for these studies were determined directly by measuring the DNA-binding activity of each ZFP preparation using conditions under which binding is essentially stoichiometric (ZFP and target site concentrations of >100 nM). Using this modified protocol, the SP1 zinc finger protein exhibits a significantly higher affinity for its target site than was determined in previous studies (Zhang et al., supra) and it is likely that both the use of activity-based estimates of ZFP concentration and the new binding buffer in these studies contributed to the difference in apparent Kds.

Construction of Zinc Finger Fusion Proteins. VEGF-A-targeted zinc fingers were assembled in an SP1 backbone and cloned into the pcDNA3 mammalian expression vector (Invitrogen, Carlsbad, Calif.) as described previously (Zhang et al., supra; WO 00/41566; and WO 00/42219). A CMV promoter was used to drive the expression of all the ZFPs in mammalian cells. All ZFP constructs contained an N-terminal nuclear localization signal (Pro-Lys-Lys-Lys-Arg-Lys-Val, SEQ ID NO:224) from SV40 large T antigen, a Zinc Finger DNA-binding domain, an activation domain, and a FLAG peptide (Asp-Tyr-Lys-Asp-Asp-Asp-Asp-Lys, SEQ ID NO:225). ZFP-VP16 fusions contained the herpes simplex virus VP16 activation domain from amino acid 413 to 490 (Sadowski et al., supra; Zhang et al, supra; WO 00/41566; and WO 00/42219). ZFP-p65 fusions contained the human NF-κB transcription factor p65 subunit (amino acid 288–548) as the activation domain (Ruben et al., supra).

Assay for the activity of ZFP fusions for human VEGF-A reporter activation. The effect of ZFPs on human VEGF-A promoter activity was measured using a luciferase reporter construct containing the human VEGF-A promoter. The human VEGF-A luciferase reporter construct pGLPVFH was made by inserting a genomic DNA fragment containing 3318 base pairs of the human VEGF-A promoter and its flanking sequences (nt −2279 to +1039 with respect to the transcription start site) into the multiple cloning site region of the pGL3 vector (Promega, Madison, Wis.) between the KpnI and NcoI sites. The translation start codon ATG of the VEGF-A gene was directly fused with the luciferase gene in this construct. Human embryonic kidney cells (HEK 293) were grown in DMEM (Dulbecco's modified Eagle's medium), supplemented with 10% fetal bovine serum, in a 5% CO2 incubator at 37° C. Cells were plated in 24-well plates at a density of 160,000 cells per well a day before transfection. The reporter construct and ZFP-VP16 fusion plasmid were co-transfected into the cells via LipofectAMINE reagent (Gibco Life Technologies, Rockville, Md.) according to manufacturer's recommendations, using 1.5 µl LipofectAMINE reagent, 260 ng of the VEGF-A reporter construct, 30 ng of plasmid DNA encoding ZFP-VP16, and 10 ng of control pRL-CMV plasmid (Promega, Madison, Wis.). Medium was removed and replaced with fresh medium 16 hours after transfection. Forty hours after transfection, medium was removed, and the cells were harvested and assayed for luciferase reporter activity using the Dual-luciferase Assay System (Promega, Madison, Wis.) according to manufacture's protocol.

Assays for the activity of ZFP fusions on the endogenous VEGF-A gene in human cells by transient transfection. Human embryonic kidney cells (HEK 293) were grown in DMEM (Dulbecco's modified Eagle's medium), supplemented with 10% fetal bovine serum, in a 5% CO2 incubator at 37° C. Cells were plated in 24-well plates at a density of 160,000 cells per well. A day later, plasmids encoding ZFP-VP16 fusions were transfected into the cells using LipofectAMINE reagent (Gibco Life Technologies, Rockville, Md.) according to manufacture's recommendations, using 1.5 µl LipofectAMINE reagent and 0.3 µg ZFP plasmid DNA per well. Cells are transfected at 50% confluence or 90% confluence, or any integral percentage therebetween. Medium was removed and replaced with fresh medium 16 hours after transfection. Forty hours after transfection, the culture medium and the cells were harvested and assayed for VEGF-A expression. VEGF-A protein content in the culture medium was assayed using a human VEGF ELISA kit (R&D Systems, Minneapolis, Minn.) according to manufacture's protocol.

For western analysis of ZFP protein expression, cells were lysed with Laemmli Sample Loading Buffer and the lysates were analyzed by a 10% polyacrylamide gel electrophoresis (BioRad, Hercules, Calif.) followed by western blotting using anti-FLAG antibody (Sigma, St. Louis, Mo.) which recognizes the FLAG epitope tag of the designed ZFPs. The western blots were visualized by ECL (Amersham Phamacia Biotech, Piscataway, N.J.) as described previously (Zhang et al., supra).

For quantitative RT-PCR analysis of VEGF mRNA level, the cells were lysed and total RNA was prepared using the RNeasy Total RNA Isolation Kit with in-column DNase treatment, according to the manufacturer's instructions (Qiagen, Valencia, Calif.). Twenty five ng RNA were used in real-time quantitative RT-PCR analysis using Taqman chemistry on an ABI 7700 SDS machine (Perkin Elmer Applied Biosystems, Foster City, Calif.) as described previously (Zhang et al., supra). Briefly, reverse transcription was performed at 48° C. for 30 min using Multiscribe Reverse Transcriptase (PE BioSystems, Foster City, Calif.). Following a 10 min denaturation at 95° C., PCR amplification using AmpliGold DNA polymerase was conducted for 40 cycles at 95° C. for 15 seconds and at 60° C. for 1 minute. The results were analyzed using SDS version 1.6.3 software (PE BioSystems, Foster City, Calif.). The primers and probes used for Taqman analysis are listed in Table 5. These primers and probes recognize all known splice variants of the human VEGF-A gene, but do not distinguish among them.

SDS at 68° C., the membrane was exposed to film. The same membrane was stripped by boiling in 0.1% SDS and re-hybridized with a human β-actin antisense riboprobe.

Analysis of splice variants of VEGF-A mRNA—To detect the multiple splice variants of VEGF-A mRNA, total RNA samples (0.5 µg) were subjected to a 20-cycle RT-PCR reaction using Titan™ one-tube RT-PCR system (Roche Molecular Biochemicals, Indianapolis, Ind.). The primers used were 5'-ATGAACTTTCTGCTGTCTTGGGTGCATT-3' (SEQ ID NO:235), and 5'-TCACCGCCTCGGCTTGTACAT-3' (SEQ ID NO:236). The PCR products were resolved on a 3% Nusieve 3:1 agarose gel (FMC, Rockland, Me.), blotted onto a Nytran SuperCharge membrane (Schleicher & Schuell, Keene, N.H.), and analyzed by Southern hybridization using a $^{32}$P-labeled human VEGF-A165 antisense riboprobe. The expected PCR product sizes for VEGF-189, VEGF-165 and VEGF-120 were 630, 576, and 444 bp, respectively.

III. Results

Constitutive and cell-specific regions of accessible chromatin associated with VEGF-A.—Chromatin mapping studies encompassed a variety of cell types from human and rat, including both tumor lines and primary cells. The scope of this survey, as well as choice of cell types, was motivated by the goal of developing candidate ZFPs for a variety of pro- and anti-angiogenic gene therapies. An initial goal was to

TABLE 5

Nucleotide sequences of primers and probes used for Taqman analysis

| | Sequence | SEQ ID NO. |
|---|---|---|
| VEGF-A forward primer | 5'-GTGCATTGGAGCCTTGCCTTG-3' | 226 |
| VEGF-A reverse primer | 5'-ACTCGATCTCATCAGGGTACTC-3' | 227 |
| VEGF-A Taqman Probe | 5'-FAM-CAGTAGCTGCGCTGATAGACATCCA-TAMRA-3' | 228 |
| GAPDH forward primer | 5'-CCATGTTCGTCATGGGTGTGA-3' | 229 |
| GAPDH reverse primer | 5'-CATGGACTGTGGTCATGAGT-3' | 230 |
| GAPDH Taqman Probe | 5'-FAM-TCCTGCACCACCAACTGCTTAGCA-TAMRA-3' | 231 |
| VP16-FLAG forward primer | 5'-CATGACGATTTCGATCTGGA-3' | 232 |
| VP16-FLAG reverse primer | 5'-CTACTTGTCATCGTCGTCCTTG-3' | 233 |
| VP16-FLAG Taqman Probe | 5'-FAM-ATCGGTAAACATCTGCTCAAACTCGA-TAMRA-3' | 234 |

Abbreviations: FAM: aminofluorescein; TAMRA: tetramethylrhodamine

Figure 1:
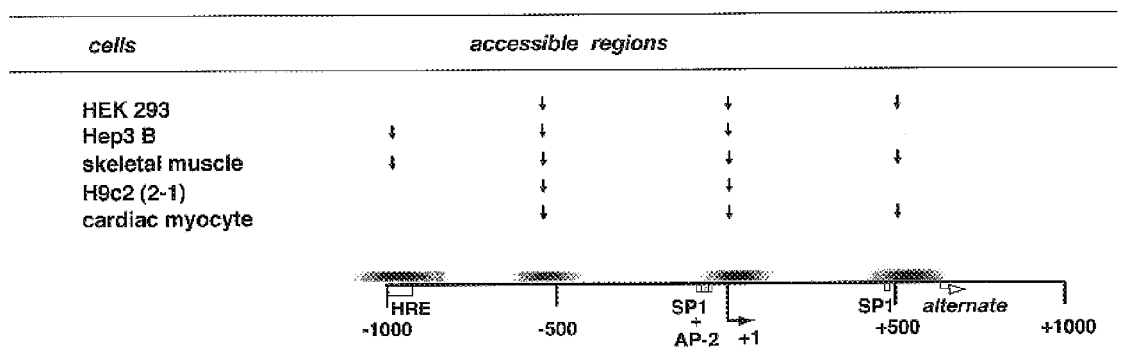
FIGS. 1A–1F show an analysis of regions of enhanced chromatin accessibility in the promoter of VEGF-A.
Figure 1:

RNA blot analysis of VEGF mRNA. HEK 293 cells were grown in 150 mm dishes and transfected with a pcDNA3 vector control or a ZFP-encoding plasmid, using LipofectAMINE reagent (Gibco Life Technologies, Rockville, Md.) according to the manufacture's recommendations. Cells and conditioned media were harvested forty hours after transfection. Total RNA was extracted from the cells using Trizol reagent (Gibco Life Technologies, Rockville, Md.) followed by RNeasy total RNA isolation midi-prep system (Qiagen, Valencia, Calif.). For RNA blots, total RNA samples (30 µg) were resolved on a 1.2% formaldehyde agarose gel and blotted onto a Nytran SuperCharge membrane (Schleicher & Schuell, Keene, N.H.). The membrane was hybridized to $^{32}$P-labeled human VEGF-A165 antisense riboprobe at 68° C. in Ultrahyb™ hybridization buffer (Ambion, Austin, Tex.). After washing with 0.1×SSC, 0.1% identify any constitutive accessible chromatin regions in the VEGF-A promoter, as well as those specific to medically relevant target tissues and model organisms. Accordingly, DNAse hypersensitivity analysis was conducted on chromatin from a number of different primary cells and cell lines. The results of this analysis indicate the existence of four distinct hypersensitive regions in or near the VEGF-A gene. Two of these, centered on approximately bp −550 and +1 of the VEGF-A promoter, were invariably observed in every cell type tested. FIG. 1 shows typical experimental results identifying these regions in both human (FIG. 1A) and rat (FIG. 1B). Both regions appear as doublets when viewed at higher resolution (FIGS. 1A and 1C). The discovery of an open region at '+1' was somewhat expected, as hypersensitive regions are often observed in the vicinity of sites for transcription initiation (see, e.g., Gross et al. (1988) Ann.

Rev. Biochem. 57: 159–197), and this region further contains several conserved regulatory elements which have been shown to be important for VEGF-A activation, including targets for SP1 and AP-2. Milanini et al. (1998) J. Biol. Chem. 273: 18,165–18,172. The observation of accessible chromatin in the '−550' region (in both human and rat chromatin) was somewhat more surprising, as no regulatory elements have thus far been mapped to this area of the VEGF-A promoter. However, it is noted that this region of the VEGFA promoter exhibits a high degree of sequence conservation among humans, mouse and rat (FIG. 1F, gray trace), which becomes more pronounced when conservation is assessed in terms of regulatory element-sized sequence blocks, (FIG. 1F, black trace), and that the DNAse I hypersensitivity of this region (as well as that of the '+1' region) is also conserved between rat and human. Indeed, analysis of a construct comprising a DNA fragment containing this region, fused to a SV40 basal promoter driving a luciferase reporter gene, indicates that this region mediates cis-acting regulatory functions. The possibility that the −550 region was inherently more susceptible to DNAse I digestion was excluded by performing a control mapping study using purified naked genomic DNA, that indicated no enhanced cutting of this region by DNAse I.

In addition to the constitutive hypersensitive regions found at −550 and +1, two other stretches of accessible chromatin, apparent in only a subset of cell types tested, were identified. One of these regions encompassed approximately 300 bp centered on the hypoxia response element (HRE) of VEGF-A, and was observed in human primary skeletal muscle cells (FIG. 1C) and in the Hep3B cell line. In contrast, this site was clearly not observed in HEK293 cells (FIG. 1C). The hypoxia response element encompasses a region of enhanced sequence conservation in the VEGF-A promoter (FIG. 1F), and has been shown to contain several conserved regulatory elements that are required for induction of VEGF-A by hypoxia, including a binding site for HIF-1. Ikeda et al. (1995) J. Biol. Chem. 270: 19,761–19,766; Liu et al. (1995) supra; Grant et al. (2000) Biochemistry 39: 8187–8192. Finally, a hypersensitive region was observed, approximately 500 bp downstream of the transcription start site, in HEK293 cells (FIG. 1D), primary skeletal muscle cells, and rat primary cardiac myocytes (FIG. 1B). Interestingly, this region contains a putative SP1 regulatory element and is adjacent to an alternative transcription start site (FIG. 1F). Akiri et al. (1998) Oncogene 17: 227–236. This region also displayed the capacity to activate the expression of a reporter gene in cis. In summary, the inventors have identified three regions accessible to DNAse I in HEK293 cells, centered at approximately bp −550,+1, and +500 relative to the transcriptional start site of VEGF-A.

Design and biochemical characterization of ZFPs targeted to open chromatin regions of VEGF-A. ZFPs that bind to sequences contained within each of the hypersensitive regions described above were designed. Design and selection studies of zinc finger-DNA recognition have yielded a diverse collection of fingers with characterized triplet specificities. See, for example, Elrod-Erickson et al. (1998) Structure 6: 451–464 and references cited supra. Collectively, these fingers provide a directory of triplet-binding modules that can, under certain conditions, be mixed and matched to obtain multifinger proteins with desired binding properties. Using this approach, a series of ZFPs targeted to sites within the '−550', '+1' and '+500' open chromatin regions observed in 293 cells (FIG. 2D) were designed, and genes encoding these ZFPs were assembled. Genes encoding two control ZFPs, targeted to sites outside of the hypersensitive regions, were also assembled. Designs for these ZFPs are shown in Tables 3, 4 and 6. The ZFPs were named according to their target location relative to the transcription start site of VEGF-A. Thus the first base in the target sequences of VZ-475 and VZ+590 lie 475 base pairs upstream and 590 nucleotides downstream, respectively, of the principal transcription initiation site of the VEGF-A gene. One of these ZFPs has two target sites in this region and so has been given a complex name to reflect this fact (VZ+42/+530). Where multiple ZFPs are targeted to a given sequence, this is indicated by the use of a small letter suffix at the end of each name to distinguish between alternate ZFP designs.

Using previously described methods (see, for example, co-owned WO 00/41566 and WO 00/42219, and Zhang et al., supra), genes encoding the ZFP designs were assembled and each of the encoded proteins was expressed in recombinant form (FIGS. 2A–2C). The DNA-binding affinity of each of the ZFPs was then characterized using a gel shift assay. All of the designed ZFPs exhibited apparent $K_d$S for their intended DNA targets that were in the nanomolar range. For comparison, under these conditions SP1 exhibited an apparent $K_d$ of 0.25 nM for its DNA target. These studies demonstrated that each designed ZFP recognizes its target site with high affinity.

Activation of the human VEGF-A gene promoter by ZFPs. Each of the designed ZFPs was fused to the minimal activation domain of the VP16 transcription factor and tested for its ability to activate a reporter gene under the control of a VEGF-A promoter. Fusion constructs also contained a N-terminal nuclear localization sequence and a C-terminal FLAG epitope tag. The reporter plasmid was constructed to contain a firefly luciferase gene under the control of human VEGF-A promoter. When transiently cotransfected into cells with the reporter plasmid, all of the designed ZFP-VP16 fusions were able to activate the reporter (FIG. 3A). The range of activation varied between 3- to 15-fold. The activation was ZFP-dependent; since a Green Fluorescent Protein-VP16 fusion was unable to activate the reporter. See also FIG. 12. These results showed that all of the designed ZFPs were active on an extrachromosomal DNA template.

Transcriptional activation of an endogenous human VEGF-A gene using ZFPs. To test whether these ZFP-VP16 fusions were also active in regulating VEGF-A gene transcription from the endogenous chromosomal locus, the designed ZFP-VP16 fusions were transiently transfected into HEK293 cells, and their effect on endogenous VEGF-A gene expression was analyzed. Human embryonic kidney cells (HEK 293) produced relatively low levels of VEGF-A in the absence of any ZFP constructs. As shown in FIG. 3C, expression of the ZFP-VP16 fusions designed as described above resulted in the secretion of elevated levels VEGF-A into the culture medium, as determined by ELISA. The range of activation varied between 2- to 15-fold, with ZFP VZ+434b the most active. The increased VEGF-A protein production induced by ZFP was correlated with a 2- to 10-fold increase in the level of VEGF-A mRNA as determined by quantitative PCR (FIG. 3D). The various ZFP-VP16 fusions activated human VEGF-A mRNA transcription with varying abilities, with ZFP VZ+434b being the most active. The different ZFP fusions were found to be expressed to similar levels, as determined by western blotting for protein levels (FIG. 3E) and by Taqman for mRNA expression (FIG. 3F). See also FIGS. 10 and 13 (for VEGF protein levels induced by additional ZFP constructs) and FIG. 11 (for a corresponding analysis of VEGF mRNA levels).

The behavior of ZFPs targeted to the accessible regions of the VEGF A gene was compared with that of ZFPs targeted to non-accessible regions. Representative data from these studies are shown in FIG. 4. Whereas all four ZFPs tested activated the extrachromosomal reporter construct to approximately equal levels, a clear discrepancy was seen regarding activity against the endogenous VEGF-A gene. The accessible-region targeted ZFPs activated VEGF-A by factors of 4 to 5 while the ZFPs targeted to sites outside of the accessible regions showed no appreciable increase in VEGF-A expression level. Thus, in certain cases, it can be advantageous to target a designed ZFP to a binding site present in an accessible region of cellular chromatin.

Activation of a human VEGF-A gene by ZFPs fused with different activation domains. To achieve a higher level of VEGF-A activation by ZFPs in human cells, the performance of other activation domains was tested and compared to that achieved by VP16. It was found that use of the activation domain from the p65 subunit of NF-κB provided higher levels of activation, when tested using several of the designed ZFPs (FIG. 5). In this experiment, some ZFP-p65 fusions, for example the ZFP VZ+434b, induced levels of VEGF-A protein that were 3- to 4-fold higher than those induced by ZFP-VP16 fusions (FIG. 5C), even though the ZFP-p65 fusion proteins and the ZFP-VP16 fusion proteins were expressed and accumulated in cells to similar levels (FIG. 5B). The higher level of VEGF-A protein production induced by the ZFP-p65 fusion was consistent with a higher level of VEGF-A mRNA transcription, as determined by Taqman analysis (FIG. 5D). Interestingly, for some ZFPs, such as VZ-8, the p65 fusions displayed activities similar to those of the VP16 fusions. Therefore, it seems that VP16 and p65 have different target site-dependent activation mechanisms.

Synergy between ZFPs in the activation of a human VEGF-A gene. The availability of a set of activating ZFPs targeted to diverse regions of the VEGF gene promoter, and fused to different activation domains, provided an opportunity to investigate whether combinations of ZFPs with different activation domains could achieve synergistic control of VEGF gene transcription. To test the possibility, various ZFP-VP16 and ZFP-p65 fusions were cotransfected into human HEK293 cells, and VEGF levels were determined by ELISA and Taqman. As shown in FIG. 6, the ZFPs VZ+434b-VP16 and VZ-573a-p65 activated VEGF production in 293 cells by 8- and 6-fold respectively. However, when these two fusions were co-transfected at a 1:1 ratio into the cells, the level of VEGF gene activation (30-fold) was more than additive, compared to the levels induced by each individual ZFP. A similar synergy between the ZFPs VZ+434b-p65 and VZ-573a-VP16 was also observed.

Comparison of VEGF induction by ZFPs with levels of VEGF-A induced by hypoxia.—In order to assess the magnitude of activation of VEGF-A expression by ZFP fusions, with respect to activation of VEGF by a physiologically relevant processes, VEGF levels induced by ZFP fusions were compared with those induced by hypoxia. For many of the ZFP fusions tested, for example ZFP VZ+434b, the ZFPs were capable of activating VEGF-A expression to a level higher than that induced by hypoxia. As shown in FIG. 7, HEK293 cells grown under hypoxic conditions had a steady-state VEGF-A mRNA level that was 5-fold higher than that in cells grown in normoxic conditions (FIG. 7B), and accumulated VEGF-A protein to nearly 400 pg/ml in the culture medium (a 10-fold increase, FIG. 7A). ZFP VZ+434b fused to a p65 activation domain induced expression of the VEGF gene to levels 5- to 10-fold greater than that induced by hypoxia, as evidenced by an accumulation of VEGF protein in culture medium to nearly 4000 pg/ml (FIG. 7A) and a 20-fold increase in VEGF mRNA level (FIG. 7B). This observation was also confirmed by RNA blot analysis (FIG. 7C).

Activation of multiple VEGF splice variants using a single ZFP. Several splice variants of human VEGF-A mRNA have been reported, each one comprising a specific exon addition. Ferrara (1999) supra. The major VEGF mRNA splice variants produce polypeptides with 121, 165, and 189 and 206 amino acids, although VEGF206 is rarely expressed and has been detected only in fetal liver. Because the designed ZFPs activated gene transcription from the natural chromosomal promoter (see supra), they would be expected to activate all of the different VEGF-A transcripts equally, preserving their relative proportions. To confirm this notion, the ability of the ZFP VZ+434b to activate multiple transcripts from the same promoter was analyzed. To distinguish the splice variants, RT-PCR was performed using primers flanking the regions of differential splicing, such that a distinct PCR product is produced for each splice variant. The PCR products were then analyzed by Southern hybridization using a VEGF165 probe. Three splice variants, VEGF-A-189, VEGF-A-165, and VEGF-A-121 were detected in 293 cells, with VEGF-A-165 being the predominant form. As demonstrated in FIG. 7D, the introduction of a single ZFP, VZ+434b, as either a VP16 or a p65 fusion, resulted in a proportional increase in levels of all of the splice variants.

IV. Discussion

This example demonstrates the successful design of a panel of ZFPs capable of activating the endogenous human VEGF-A gene from diverse target sites within its promoter. The experimental approach incorporated information regarding the chromatin structure of the VEGF-A locus, since, in certain circumstances, information regarding chromatin structure may be used in combination with ZFP design principles to provide efficient means for identifying artificial transcription factors capable of specifically regulating endogenous genes. Several of the designed ZFPs disclosed herein are potent activators, yielding VEGF-A levels exceeding those observed during induction by hypoxia. While an understanding of mechanism is not required for the practice of the disclosed methods and/or use of the disclosed compositions, it is possible that designed ZFP fusions targeted to DNAse I accessible regions may act synergistically with the natural transcription factors which presumably bind to these regions.

The panel of artificial transcription factors disclosed herein, which are targeted to diverse sites in the VEGF-A gene, provides a unique tool for assessing the structural determinants of transcriptional activation at an endogenous locus, and several of the results reflect possible transcriptional effects of chromatin structure. For example, different members of the panel of ZFPs exhibit different patterns of activation of the endogenous VEGF-A locus, compared to an extrachromosomal promoter reporter construct (compare FIGS. 3B and 3C). Furthermore, the ability of the p65 activation domain to outperform VP16 varies in a position-dependent manner, with relative activation levels varying over a factor of three, depending on the location of the ZFP target within the VEGF-A locus (FIG. 5C). These effects could reflect limitations on the capacity of designed transcription factors to activate an endogenous locus resulting from the structural context imposed by chromatin, possibly coupled with the binding of other regulatory proteins. They also reemphasize the idea that different activation domains have distinct regulatory and steric requirements for optimal performance.

The ability to generate a panel of factors targeted to an endogenous locus also provides practical advantages in a variety of applications. In studying the effects of up- or down-regulation of a target locus, for example, conclusions regarding gene function will be strongest if a given effect is observed repeatedly using a number of different regulators. In addition, for potential medical uses, the availability of multiple ZFP candidates provides a greater likelihood of obtaining a lead which yields optimal benefits with minimal side effects. Additional possibilities for use of these proteins are in the study of transcriptional regulation. For example, the ability to target multiple activation domains to arbitrary sites in the same locus has clear applications in the study of synergy. In this respect, greater than additive effects on VEGF expression, mediated by cotransfected VP16- and p65 activation domain-bearing ZFPs, has been disclosed herein. It is likely that, by using larger combinations of appropriately targeted functional domains, designed ZFPs may offer the prospect for total reconstitution of activation processes using completely defined components.

An additional observation of the studies disclosed herein is that ZFPs fused with the NF-κB p65 subunit (Ruben et al., supra) activate the endogenous VEGF gene as well as or better than the 78 amino acid activation subdomain of the Herpes Simplex Virus VP16 protein (Sadowski et al., supra). Although both VP16 and NF-κB p65 are strong acidic activation domains and share certain functional features; for example, recruitment of the ARC/DRIP complex and facilitated assembly of a preinitiation complex on promoter DNA (Naar et al. (1999) Nature 398: 828–832; Rachez et al. (1999) Nature 398: 824–828); differences in their transactivation mechanism have been reported. For example, the histone acetyltransferase activity of p300 has been demonstrated to be necessary for activation by NF-κB, but less essential for activation by VP16. Kraus et al. (1999) Mol. Cell. Biol. 19: 8123–8135; Li et al. (2000) Mol. Cell. Biol. 20: 2031–2042. It is possible that the local availability of p300 or other coactivators in the endogenous VEGF locus may account for the observed differences.

Finally, the designed ZFPs disclosed herein upregulate each major splice variant of VEGF-A, in proportions similar to those observed under physiological conditions (e.g., hypoxia). This is important because recent studies suggest that proper isoform balance is crucial for VEGF-A function. Carmeliet et al. (1996) supra; Carmeliet et al. (1999) supra; Grunstein et al. (2000) supra. In particular, the 165, 189 and 206 amino acid isoforms of VEGF-A have increasingly stronger heparin-binding domains, which are involved in presentation to VEGF receptors and in binding to the extracellular matrix. Heparin-binding ability is a critical determinant of VEGF-A potency, resulting in different biological activities for different isoforms. Currently, most VEGF-A gene therapy trials involve the application of just a single VEGF-A splice variant cDNA or protein isoform. Isner et al. (1996) Lancet 348: 370–374; Esakof et al. (1999) Hum. Gene Ther. 10: 2307–2314; Rosengart et al. (1999a) Ann. Surg. 230: 466–470, discussion 470–472; Rosengart et al. (1999b) Circulation 100: 468–474; Hendel et al. (2000) Circulation 101: 118–121. It has been suggested that an ideal gene therapy agent should be able to recapitulate natural ratios of various different VEGF-A isoforms. Activation of VEGF-A using the designed ZFPs disclosed herein therefore offers advantages in this regard, providing key components of pro-angiogenic gene therapy agents.

EXAMPLE 2

Activation of an Endogenous Mouse VEGF Gene

The sequence of the murine VEGF gene (GenBank Accession Number U41383) was searched for ZFP target sites and a ZFP, denoted VG10A/8A, was designed to bind to a site between 56 and 73 nucleotides downstream of the transcriptional startsite. The sequence of this target site is 5'-TGAGCGGCGGCAGCGGAG (SEQ ID NO:237). The six-finger ZFP designed to bind this target site has the following amino acid sequences in the recognition helices (proceeding in an N-terminal to C-terminal direction): RSDNLAR (SEQ ID NO:35); RSDELQR (SEQ ID NO:159); QSGSLTR (SEQ ID NO:57); RSDELTR (SEQ ID NO:122); RSDELSR (SEQ ID NO:238) and QSGHLTK (SEQ ID NO:239). This six-finger binding domain was fused to a VP16 activation domain, according to methods described in Example 1. A plasmid encoding this ZFP fusion was co-transfected into mouse cells with a reporter gene under the control of the murine VEGF promoter, and a 29-fold activation of reporter gene activity was observed.

This ZFP fusion construct was also injected into mouse skeletal muscle to test for activation of the endogenous VEGF gene. One hundred microliters of a 1 mg/ml solution of plasmid DNA was injected into two separate sites in the quadriceps muscle of a live mouse. The contralateral quadriceps muscle was subjected to two control injections, of a plasmid lacking ZFP-encoding sequences, at sites in the muscle similar to those receiving the experimental injections. Injection needles were marked to assure similar depths of injection, and sites of injection were marked with India Ink.

Three days after injection, identically-sized tissue samples were harvested from the marked injection sites by punch biopsy. Proteins were extracted from the tissue samples and separated by gel electrophoresis. The gel was blotted and the blot was probed with an anti-mouse VEGF antibody (R&D Systems, Minneapolis, Minn.). Results are shown in FIG. 8. The results indicate that production of VEGF is enhanced in mouse muscle that has been injected with a plasmid encoding a ZFP-VP16 fusion, and that the enhancement of VEGF expression is not simply due to injection per se.

EXAMPLE 3

Activation of an Endogenous Rat VEGF Gene

Experiments similar to those described in Example 2 were performed on rats, using ZFPs targeted to sites in the rat VEGF gene, certain of which are homologous to ZFP target sites in the human VEGF-A gene and were shown to activate the human VEGF-A gene (see Example 1, supra). Sequences of the target sites and recognition helices of these ZFPs are provided in Table 7. ZFP-VP16 fusions were injected into rat skeletal muscle, similar to the mouse injections described in Example 2. Analysis by immunoblotting, using an anti-rat VEGF antibody (R&D Systems, Minneapolis, Minn.), showed that all of the ZFP fusions activated rat VEGF production, and that BVO12A-11A, BVO14A-13B, and VOP 32B induced a marked increase in VEGF expression, between 5- and 10-fold.

EXAMPLE 4

Stimulation of Wound Healing and Angiogenesis in Mice Using VEGF-Targeted ZFP Fusions In this example, punch biopsy wounds were made in both quadriceps muscles of a mouse. A plasmid encoding the VG10A/8A ZFP-VP16 fusion under the transcriptional control of a CMV promoter (as used in Example 2, supra) was injected into the periphery of one of the wounds, and a control plasmid, lacking sequences encoding a ZFP binding domain, was injected into the contralateral wound. After three days, tissue was excised, and hematoxylin & eosin-stained thin sections were examined microscopically. Results are shown in FIG. 9. FIG. 9B shows a low-magnification image in which margins of ingrowing tissue are apparent beneath the blood clot covering the wound (clot at top left, margins of ingrowing tissue indicated by arrowheads). In comparison, no ingrowing tissue is seen beneath the clot in the control-injected tissue shown in FIG. 9A. FIGS. 9D and 9F show high-magnification images which reveal increased vascularization in the ZFP-injected tissue, evidenced by a larger number of capillary sections and red blood cells, compared to the control-injected tissue shown in FIGS. 9C and 9E.

The results of this experiment indicate that activation of the VEGF gene by targeted ZFP fusions leads to faster wound healing and increased vascularization.

EXAMPLE 5

Regulation of Multiple Human VEGF Genes Using a Single ZFP Fusion Protein

In this example, the ability of a single ZFP fusion to regulate a plurality of human VEGF genes was tested. As shown in Table 2, the VOP 28A and VOP 30A ZFPs have target sites in both the VEGF-A and VEGF-C genes. VOP 28A has target sites at −573 in the VEGF-A gene and +61 in the VEGF-C gene; while VOP 30A has a target sites at +42 and +530 in VEGF-A and one at −481 in VEGF-C.

HEK 293 cells were transfected with a plasmid encoding either a VOP 28A-VP16 fusion or a VOP 30A-VP16 fusion, according to the methods described in Example 1, supra. Forty hours after co-transfection, VEGF-A mRNA was quantitated by TaqMan® as described in Example 1, using the primers and probes shown in Table 5. VEGF-C mRNA was quantitated in the same RNA samples, according to the methods disclosed in Example 1, using the primers and probe disclosed in Table 8. The results, shown in FIG. 14, indicate that each of the VOP 28A and VOP 30A fusion proteins activate production of both VEGF-A and VEGF-C mRNA.

As a control, HEK 293 cells were transfected with a plasmid encoding a VOP 32B-VP16 fusion. VOP 32B has a target site in the VEGF-A gene, at +434, but has no target site in the VEGF-C gene. Strong activation of VEGF-A transcription, but no change in VEGF-C mRNA levels, was observed in these cells (FIG. 14).

These results show that multiple VEGF genes can be regulated by a single ZFP, leading to more efficient regulation of angiogenesis.

EXAMPLE 6

In Vivo Induction of VEGF in Mice Using VEGF-Targeted ZFP Fusions and Stimulation of Angiogenesis and Wound Healing I. Introduction This series of experiments was designed to demonstrate further the ability of appropriately designed ZFP fusion proteins to activate expression of VEGF in vivo, and to show the ability of such proteins to stimulate angiogenesis and wound healing in mouse model systems that are used as models of the corresponding processes in humans.

Engineered ZFPs and knowledge of chromosomal structure were utilized in a variety of different types of investigations to achieve selective activation of VEGF A. As in Example 1, certain VEGF stimulating ZFPs were designed following identification of targets by DNAse I hypersensitive mapping analysis. These initial experiments led to the identification of three different DNAse-I accessible regions in both NIH3T3 cells and C127I cells. ZFPs were designed to bind to either a 9-bp or 18-bp target site within the accessible regions identified in each cell type. Each of these designed ZFPs was shown to bind tightly to its intended target with an apparent $K_d$ of <0.6 nM and more tightly than a naturally occurring transcription factor (SP1).

Fusion proteins containing one of the designed ZFPs and the VP16 transcriptional activation domain (Sadowski et al. (1988) Nature 335: 563–564) were then tested for their ability to activate expression of the endogenous VEGF-A gene in C 127I cells at both the transcript and protein levels. As described more fully infra, the results demonstrate that the designed ZFPs were able to activate the endogenous VEGF-A locus and, in so doing, accelerate processes of angiogenesis, reepithelialization and wound healing.

II. Experimental Procedures

A. Design of VEGF Regulating Zinc Finger Proteins

Mapping of DNAse I—accessible chromatin regions in the mouse VEGF-A locus. C127I and NIH3T3 cells were obtained from the American Type Culture Collection and maintained essentially as recommended by the supplier. Nuclei were isolated and treated with DNAse I (Worthington) essentially as described (Zhang et al. (2000) J. Biol. Chem. 275: 33,850–33,860; and Liu, et al. (2001) J. Biol. Chem. 276: 11,323–11,334), except that DNAse I digests were for 1.5 min at 22° C. and the concentrations of DNAse I used were as indicated in the legend to FIG. 15A. Genomic DNA isolation, restriction enzyme digestion and Southern blot analysis were then performed essentially as described (Zhang et al., supra; and Liu, et al., 2001, supra), except that enzymes and probes were as indicated in FIG. 15A.

Synthesis of genes encoding zinc finger proteins. The assembly of genes encoding the three-finger ZFPs mVZ+426 and mVZ+509 has been described (Liu et al., 2001, supra). [These designs were referred to, respectively, as VZ+434 and VZ+42/+530 in that study.] Briefly, oligos encoding α-helix and β-sheet regions of each three-finger protein were assembled using PCR and each resultant ZFP gene was cloned into the pMal-c2 plasmid (New England Biolabs) as a fusion with DNA encoding maltose binding protein.

To assemble the gene encoding the six-finger protein mVZ+57, the following two-step strategy was utilized. First, genes encoding three finger proteins corresponding to fingers 1–3 and 4–6 of VZ+57 were constructed and cloned as above, yielding constructs pMal-c2 '1–3' and pMal-c2 '4–6'. Next, these two genes were joined via a short DNA spacer encoding a flexible peptide linker. This was accomplished as follows: (i) PCR of the '4–6' ZFP gene using the primers 5' CCC<u>AGATCT</u>GGTGATGGCAAG AAGAAG-CAGCACCATCTGCCACATCCAG (SEQ ID NO:241) and 5'CCC<u>AAGCTT</u>AGGATCCACCCTTCTTGTTCTGGTG GGT (SEQ ID NO:242); (ii) digestion of the resultant fragment with Bgl II and Hind III (sites underlined in primers); and (iii) ligation into the BamHI and Hind III sites of the pMal-c2 '1–3'. The resultant protein, VZ+57, consists of the '1–3' and '4–6' three-finger modules connected by a flexible peptide linker, with the amino acid sequence between the second zinc-coordinating histidine of finger 3 and the first zinc-coordinating cysteine of finger 4 (both underlined) as follows: <u>H</u>QNKKGGSGDGKKKQH<u>IC</u> (SEQ ID NO:243).

Binding studies. Binding studies were performed essentially as described (Liu, et al. (2001) *J. Biol. Chem.* 276: 11,323–11,334), except that the buffer was modified to the following final composition: 10 mM Tris, 100 mM KCl, 1 mM $MgCl_2$, 10 mM DTT, 0.01 mM $ZnCl_2$, 10% glycerol, 200 µg/ml bovine serum albumin, 0.02% IGEPAL. Under these conditions SP1 (a naturally occurring zinc finger containing transcription factor used as a control) exhibits a significantly higher affinity than was determined in previous studies (Liu et al., 2001, supra) and it is likely that the use of our refined binding buffer contributed to the difference in apparent $K_d$. ZFP concentrations for these studies were determined directly by measuring the DNA-binding activity of each ZFP preparation using conditions under which binding is essentially stoichiometric (i.e., concentrations of ZFP and target site $>50 \times K_d$).

Construction of retroviral vectors. The retroviral vectors described here are derived from a pLXSN, a Moloney murine leukemia virus-based vector containing a neomycin resistance gene under the control of an internal simian virus (SV40) promoter. Using EcoR1 and Xho1 restriction sites, the zinc finger expression cassette was placed immediately downstream of the LTR in pLXSN. Briefly, all ZFP constructs contained an N-terminal nuclear localization signal (Pro-Lys-Lys-Lys-Arg-Lys-Val)(SEQ ID NO:224) from SV40 largeT antigen, a Zinc Finger DNA-binding domain, the herpes simplex virus VP16 activation domain from amino acid 413 to 490, and a FLAG peptide (Asp-Tyr-Lys-Asp-Asp-Asp-Asp-Lys)(SEQ ID NO:225). The LXSN vectors were produced in the 293 AMPHO-PAK™ cell line and had titers ranging from $0.5–1.0 \times 10^6$ G418-resistant colony-forming units. Virus-containing supernatant was collected 48 hr after transfection, filtered through 0.45-mm-pore-size filter and used fresh for transduction of target cells or aliquoted and stored at $-80°$ C.

Retroviral transduction. The AMPHO-PAK™ 293 cell line was obtained from Clontech and grown according to the manufacturer's recommendation. C127I cells were obtained from the American Type Culture Collection (ATCC) and grown in Dulbecco's modified Eagle's medium (DMEN) supplemented with 10% fetal bovine serum. The cells were plated in 6-well plates at a density of $2 \times 10^4$ cells per well and then exposed 24 hour later to 2.0 ml of virus-containing supernatant in the presence of 8 µg/ml Polybrene, and incubated in a 37° C. incubator. The virus was removed 24 hour later and fresh medium was added. The cells were split 2 days later and G418 containing medium was added. A G418-resistant population of cells was established 14 days later and tested for VEGF expression by ELISA. The cells were plated at a density of $5 \times 10^5$ cells per well, refed at 24 hours and media was collected for ELISA after 24 hours.

B. Adenovirus Construction and Experiments

Construction. Recombinant E1A/E1B deleted adenovirus vectors encoding zinc finger protein (ZFP) cDNA's were produced using the Ad-Easy system (T. -C. He, et al. (1998) *Proc. Natl. Acad. Sci. U.S.A.* 95: 2509–2514). Briefly, cDNA's encoding VEGF regulating ZFP's were subcloned into the pAd-Track-CMV shuttle vector. This vector contains two separate CMV promoters, one to direct expression of inserted cDNA's and the other to direct expression of the transduction marker green fluorescent protein (GFP). In this shuttle vector, both the green fluorescent protein and the cDNA expression cassettes are flanked by genomic adenovirus-5 sequences, allowing recombination with genomic adenovirus-5 DNA (T.-C. He, et al. (1998) supra). More specifically, ZFP-encoding inserts from pcDNA MVG (a plasmid encoding the zinc finger binding domain VG10A/ 8A as described in Example 2 supra) and three-finger constructs pCV VOP 30A and pCV VOP 32B were cut by restriction digestion with EcoRI/HindIII and sub-cloned into shuttle plasmid pAdTrack-CMV, linearized with PmeI.

Each construct was co-electroporated along with the adenovirus-5 genomic vector pAd-Easy-1 into electrocompetent BJ5183 *E.coli* bacteria. Adenovirus-5 genomic DNA clones encoding the VEGF regulating ZFP's and deficient for the essential adenovirus E1A/E1B gene region were obtained by recombination between the ZFP encoding pAd-Track-CMV shuttle vectors and pAd-Easy-1 in *E.coli*. Kanamycin resistant colonies were screened for recombinants by restriction mapping, and clones with the appropriate restriction pattern were transfected into human embryonic kidney 293 cells (HEK 293's) using the Lipofectamine reagent. HEK 293's contain the E1A/E1B genes and provide these essential proteins in trans to allow production and propagation of the replication defective E1A/E1B deficient adenovirus recombinants. These recombinants do not propagate in normal mammalian cells due to the lack of E1A/E1B gene functions. Adenovirus stocks were expanded in 293 cells, purified by CsCl ultracentrifugation, desalted by column purification or dialysis against phosphate buffered saline, and titered on HEK 293 monolayers as described (see, e.g., Giordano, et al. (1996) *Nat. Med.* 2:534–9; and Giordano et al. (1997) *Circulation* 96:400–3). Adenovirus stocks were stored in 20% glycerol at $-80°$ C.

In vitro testing. To document that the above adenovirus vectors were capable of directing expression of the VEGF-A regulating ZFP's after transduction, studies were performed in cultured rat aortic smooth muscle cells (SMC). As indicated above, the ZFP constructs used in these studies contain both a FLAG epitope and a VP-16 activation domain. Adenovirus-mediated expression of the ZFP constructs was thus evaluated by Western blot analysis of proteins expressed in the SMC using antibodies directed to the FLAG epitope and the VP-16 activation domain. Briefly, SMC were grown in culture to subconfluence and were transduced with adenovirus vectors encoding either a ZFP or green fluorescent protein (GFP) (control). Transduction was carried out at a multiplicity of infection of approximately 5.48 hours after transduction the cells were scraped and protein lysates obtained for Western blot analysis using specific antibodies against either the FLAG epitope (Fisher Scientific) or VP-16.

C. Induction of the VEGF-A Gene in Skeletal and Cardiac Muscle by VEGF-ZFP's

Plasmid Injection Studies The ability of a number of different VEGF-A regulating ZFPs to induce expression of the endogenous VEGF-A gene was tested in vivo in rat skeletal muscle. Initial studies were carried out using plasmid DNA expression vectors encoding either a VEGF-A regulating ZFP fusion protein or a control protein containing the same peptide sequences absent the DNA binding domain. A commercially available plasmid in which gene expression is directed by the CMV promoter (pCDNA-3; Clontech) was used as the backbone for construction of the ZFP encoding plasmids.

Fifty µg of purified plasmid DNA encoding a VEGF-A regulating ZFP was diluted into 50 µl of phosphate buffered saline (PBS) and aspirated into a 1 cc syringe. A small incision was made in the skin overlying the adductor muscle of the hindlimb of a Sprague-Dawley rat, and the plasmid DNA was injected directly into the muscle through a 30 gauge needle. The site was marked by injecting a small amount of India ink at the point of plasmid DNA delivery. Fifty µ g of the control plasmid was injected into the contralateral hindlimb adductor muscle using the same methods. At day 3 or 6 after plasmid delivery, the rats were sacrificed and skeletal muscle from the plasmid injection sites was harvested using a 1 cm diameter punch bioptome. The muscle tissue was rinsed in ice-cold PBS and rapidly frozen in liquid nitrogen and used for subsequent VEGF-A protein expression analysis by Western blotting.

ZFP-directed VEGF-A protein expression was also evaluated in heart muscle using a similar approach. Briefly, in anesthetized and ventilated CD-1 mice, the heart was exposed by left lateral thoracotomy. Fifty μg of plasmid DNA encoding either a VEGF-ZFP or the control peptide was injected in a 50 μl volume into the apex of the heart. Injection was documented by blanching of the injection site. The chest was closed and the animal allowed to recover. Three days after injection the animals were sacrificed and the heart removed. The apex was clipped, rinsed in ice cold PBS, rapidly frozen in liquid nitrogen and used for subsequent VEGF-A protein expression analysis by Western blotting (data for these experiments is not shown). Similar techniques can be used with rats.

Adenovirus Injection Studies. Using methodology similar to that used for the plasmid DNA injection studies, VEGF-ZFP encoding or control (green fluorescent protein encoding) adenovirus vectors were injected into the hindlimb adductor muscle of CD-1 mice. Approximately $5 \times 10^8$ pfu of VEGF-ZFP encoding adenovirus was injected in a 50 μl volume of PBS into the adductor muscle using a 1cc syringe and a 30 gauge needle, as above. The contralateral adductor muscle was injected with a green fluorescent protein encoding control adenovirus. Three or six days after adenovirus injection the skeletal muscle injection site was harvested as above for Western blot analysis of VEGF-A protein expression. For those VEGF-ZFP's that were designed to bind to DNA sequences in both the murine and rat VEGF-A regulatory domains (VOP 30A, VOP 32B, BVO12), in vivo testing was also carried out in the rat hindlimb adductor muscle. These studies were carried out essentially as above, although the volume of the injectate was increased to 100 μl. Related experiments were also conducted with plasmids in the same volume.

D. Murine Ear Angiogenesis Assay

To test the ability of the designed VEGF-ZFP's to induce angiogenesis in vivo, angiogenesis in the murine ear after injection of adenovirus vectors encoding either VEGF regulating ZFP's or the control peptide green fluorescent protein was evaluated (see, e.g., Pettersson, A., et al. (2000) *Laboratory Investigation* 80:99–115). Briefly, using a 1 cc syringe and a 30 gauge needle ~$3 \times 10^8$ pfU of VEGF-ZFP encoding adenovirus was injected subcutaneously into the mouse ear in a volume of ~25 μl PBS. The contralateral ear was similarly injected with an equal amount of control (green fluorescent protein) adenovirus. Three and six days after injection, the ears were visually inspected and digital photographs obtained using the same settings at the same distances. The animals were sacrificed, the ears harvested and fresh frozen in OTC for immunohistochemical analysis of angiogenesis.

Vessel Counts. Angiogenesis/vascularization in the mouse ear was evaluated on fresh frozen tissue sections using an anti-lectin antibody (Vector Laboratories, Burlingame, Calif.) that is specific for endothelial cells (see, e.g., Christie, K. N. and Thomson, C. (1989) *J. Histochem. Cytochem.* 37:1303–1304). Briefly, frozen sections were fixed with acetone, rinsed with PBS, and incubated for 2 hours with the anti-lectin antibody. Following three sequential wash steps, the sections were incubated for 2 hours with a secondary antibody linked to alkaline phosphatase and the slides were developed using a commercial alkaline phosphatase staining kit (Vecta Inc.). Vessel counts were determined on the basis of microscopic analysis of anti-lectin immunostaining by an observer blinded to the identity of the sections. Five separate 40× microscopic fields were evaluated per section, and the number of lectin stained vessels per field was averaged.

E. Wound Healing

To evaluate the ability of the VEGF-A regulating ZFP's to augment angiogenesis in a functional in vivo biologic assay we used a well established model of cutaneous wound healing (see, e.g., Swift, M. E., et al., (1999) *Lab Invest.* 79:1479–87). Highly reproducible bilateral dorsal cutaneous wounds were created in CD-1 mice by excision of a 5 mm circle of skin using a 5 mm punch bioptome. Healing of these wounds involves production of granulation tissue, reepithelialization by ingrowth of keratinocytes and an angiogenic response. At the time of wound creation ~$5 \times 10^8$ pfu of VEGF-ZFP encoding adenovirus was delivered to the wound site by topical application in a volume of 20 μl PBS. The contralateral wound site was treated with a control adenovirus encoding green fluorescent protein.

On day 5, the wound sites were excised whole, carefully bisected, formalin fixed and embedded in paraffin blocks. Multiple serial sections were obtained and used for histologic and immunohistologic analysis. Wound reepithelialization was analyzed on hematoxylin and eosin stained sections evaluated under light microscopy with 4× and 40× objectives. Micrographic images were captured with a SPOT CCD camera and imported into Adobe Photoshop for analysis. Two parameters of reepithelialization were evaluated: a) the distance from the wound edge to the leading edge of keratinocyte ingrowth, and b) the distance between the leading edges of keratinocytes growing in from opposite sides of the wound. All measurements were made quantitatively using computer calipers, and all sections were evaluated by an observer blinded to the treatment.

Wound vessel counts were determined by immunostaining of wound sections using the endothelial cell specific anti-lectin antibody described above. Vessel counts from 5 separate microscopic fields were made per section (100× magnification) and the results per section averaged.

F. Western Blot Analysis

For Western Blot analysis of ZFP induced VEGF expression, animals were killed by euthanasia at the 3rd day after adenoviral-ZFP or control adenoviral-green fluorescent protein (GFP) injections. Skeletal muscles around the injection sites were carefully removed and homogenized at 4° C. in lysis buffer containing Tris-HCl 50 mM (pH 8.0), NaCl 150 mM, SDS 0.1%, NP-40 1%, Na Desoxycholate (0.5%) and proteinase inhibitors. After a ten-minute centrifugation (10,000 g at 4° C.), the protein-containing supernatant fraction was collected, a small part of each sample was used to determine protein concentration (BioRad) and samples were diluted (1:1) with 2×loading buffer containing 50 mM DTT and denatured by boiling 5 min. Samples containing equal amounts of total protein were loaded on and separated by electrophoresis through 12% SDS-PAGE gels (Tris-Glycine, Novex). Proteins in the gel were transferred to nitrocellulose membranes and the membranes were exposed to mouse monoclonal anti-VEGF antibody (RDI) to check the level of VEGF expression, rabbit polyclonal anti-VP16 antibody (Clonetech) to check expression of ZFP-VP16 fusion protein, and mouse monoclonal anti-muscle specific actin antibody (NCL) as an internal standard. After several washes in TBST, the blots were incubated with horseradish peroxidase (HRP)-conjugated secondary antibody for 1 h at room temperature, followed by TBST washes, and developed with an enhanced chemiluminescent substrate for detection of HRP (Pierce).

III. Results

A. Mapping of DNase I Accessible Regions in the Mouse VEGF-A Locus

The strategy for designing ZFP transcriptional regulators involved the preferential targeting of accessible regions within the locus of interest. Such regions, which are readily identified via mapping of DNase I hypersensitive sites (Gross et al. (1988) Ann. Rev. Biochem. 57: 159–197), are generally more accessible to macromolecules than surrounding stretches of DNA, and these regions often comprise binding sites for natural transcriptional regulators of the associated genes. Preferential targeting of such regions with designed ZFPs tends to yield both more effective regulation and greater potency of response (Liu et al. (2001) J. Biol. Chem. 276:11,323–11,334). Accordingly, we have mapped DNase I accessible regions in mouse VEGF-A locus. In both NIH 3T3 cells and the C127 I cell line, we observe three regions of enhanced DNase I accessibility centered approximately on bases –550, +1, and +400 (numbers relative to the start site of transcription) (FIGS. 15A and 15B). The –550 and +1 regions each appear to span approximately 200 base pairs, while the +400 region is somewhat more diffuse and encompasses approximately 300 base pairs (FIGS. 15A and 15B). We have also observed similar patterns of DNase 1 accessibility in mouse TM3 cell line (data not shown) and in a variety of cell types from man and rat (Liu et. al., 2001, supra).

B. Design and Biochemical Characterization of ZFPs Targeted to Open Chromatin Regions of Mouse VEGF-A We next chose target sites within the '+1' and '+400' accessible regions and designed zinc finger proteins that recognized these sequences with high affinity (FIG. 15C). This was accomplished by linking together fingers of known triplet preference to yield either three- or six-finger ZFPs with the desired sequence specificities. Designs for our ZFPs are shown in FIG. 15C, with the ZFPs named according to their target location relative to the transcription start site of mouse VEGF-A. Two of these designs, mVZ+426 and mVZ+509, contain three fingers and target nine base pair sequences conserved in man and mouse. Our third ZFP, mVZ+57, contains six fingers and targets an 18 base pair sequence present in mouse (but not man).

Genes for our ZFPs were assembled (see experimental procedures) and each protein was expressed and purified essentially as described (Liu et. al., 2001, supra; and Zhang et. al., supra). We then characterized the DNA-binding affinity of each ZFP using a gel shift assay. Procedures for these studies were essentially identical to those described previously (Liu et. al., 2001, supra; and Zhang et. al., supra) except for the use of a modified binding buffer. We found that our designed ZFPs bound to their targets with high affinity, with $K_d$'S of 0.031 nM (FIG. 15D). For comparison, SP1, the parent ZFP for our designs, exhibited an apparent $K_d$ of 0.053 nM for its DNA target under these conditions.

C. Activation of the Mouse VEGF-A Locus by ZFPs

We chose to use C127 I cells for our initial studies of VEGF-A activation, since this cell line exhibited a relatively low background of endogenous VEGF-A expression against which to measure activation mediated by our designed ZFPs. For these studies, each ZFP was cloned into pLXSN, a Moloney murine leukemia virus-based vector, as a fusion with a VP16 activation domain, nuclear localization sequence, and FLAG tag. C127 I cells were then exposed to this vector, and transduced cell populations were selected using G418. As shown in FIG. 16B, expression of our ZFP-VP16 fusions resulted in activation of the VEGF-A locus as determined by analysis of VEGF-A mRNA, with relative levels of VEGF-A message increasing by up to 4.6-fold for VZ+426-VP16 relative to a control construct expressing a VP16 activation domain fused to green fluorescent protein. We also observed similar increases in the levels of VEGF-A protein secreted into the medium as measured by ELISA (FIG. 16C).

D. Induction of the VEGF-A Gene in Skeletal and Cardiac Muscle by VEGF-Binding ZFPs In vitro characterization of adenovirus-mediated expression of VEGF-A regulating ZFP's. Prior to in vivo testing of the recombinant adenovirus constructs encoding the VEGF-A regulatory ZFP's, expression of the ZFP's was documented by Western blot analysis. Aortic smooth muscle cells (SMC) were transduced with an adenovirus encoding either a VEGF-A regulating ZFP or a green fluorescent protein (GFP). 48 hours after transduction the cells were washed with phosphate buffered saline and protein lysates prepared. Western blot analysis using either an anti-VP16 antibody or an anti-FLAG epitope antibody revealed expression of the ZFP constructs in adeno-VEGF-ZFP transduced cells, but not in adeno-green fluorescent protein (GFP) transduced cells (FIG. 17A).

VEGF-A protein expression after injection of recombinant adenovirus encoding VEGF-A regulating zinc finger protein VOP30A. Approximately $5 \times 10^8$ pfu of an adenovirus encoding a fusion protein comprising the VOP 30A ZFP binding domain fused to a VP16 activation domain (Adeno-VOP 30A) was injected in a volume of 50 µl phosphate buffered saline into the hindlimb adductor muscle of CD-1 mice. The contralateral hindlimb adductor muscle was injected with adenovirus encoding green fluorescent protein (adeno-GFP) as a control. Three days after the injection, the muscle encompassing the injection sites was harvested and used to prepare protein lysates for Western blot analysis of VEGF protein expression. As illustrated in FIG. 17B, adenovirus-mediated VOP30A gene expression resulted in a marked induction of the VEGF-A gene in vivo as demonstrated by the marked increase in VEGF-A protein expression. Western blotting with anti-VP16 antibody documents expression of the VOP30A construct in the injected muscle.

Induction of VEGF-A protein expression in mice after injection of Adeno-MVG. Skeletal muscle injection of adeno-MVG or adeno-GFP (green fluorescent protein) as a control was accomplished as just described supra. Three days after injection, VEGF-A protein expression was evaluated by Western blot. Induction of VEGF-A protein expression was observed as shown in FIG. 17C. Equal loading of skeletal muscle protein lysates is documented by immunostaining for actin.

VEGF-A protein expression in rats after skeletal muscle injection of plasmids encoding VEGF-A regulating zinc finger proteins. Tests were conducted in which plasmids encoding the ZFPs VOP 30A, VOP 32B, BVO12A, BVO14A or a control plasmid (lacking the ZFP binding domain) were injected into the hindlimb adductor muscle of Sprague-Dawley rats. In all plasmids, protein expression was directed by the CMV promoter. Three days after gene injection, the injection sites were excised. The results from Western blot analysis of the resulting protein lysates as shown in FIG. 17D show induction of VEGF-A protein by all four constructs.

E. Induction of Angiogenesis

Subcutaneous injection of recombinant adenovirus encoding VEGF regulating zinc finger proteins induces angiogenesis in the mouse ear. To assess the ability of VEGF-A regulating zinc finger proteins to induce angiogenesis in vivo we injected recombinant adenovirus encoding VEGF-A regulating ZFP's subcutaneously into the mouse ear. Approximately $5 \times 10^8$ pfu were injected in a volume of 25 µl subcutaneously into the ear of CD-1 mice. The contralateral ear was injected in the same manner with a control adenovirus encoding green fluorescent protein (GFP). Three days and six days later the animals were visualized and digital photographs of the ears were taken. As shown in FIGS. 18A–D, adenovirus-mediated delivery of genes encoding VEGF-A regulating ZFP's (VOP30A or VOP 32B) resulted in augmented ear vascularization. These results were correlated with data from formal vessel counts, as shown in FIG. 18E.

Increased vascularity is documented by vessel counts after adenovirus-mediated delivery of genes encoding VEGF-A regulating zinc finger proteins. To further characterize the effects of adenovirus-mediated delivery of genes encoding VEGF-A regulating ZFP's in the ear angiogenesis assay just described, immunohistochemistry facilitated vessel counts were performed on sections from control and VEGF-ZFP (VOP30A or VOP 32B) treated mouse ears. Vessel counts were performed by an observer blinded to the treatment group, and were determined by counting 5 separate fields per section at a magnification of 40× and averaging the values (n=5 per group at day 3; n=4 per group at day 6). As shown in FIG. 18E, assays conducted utilizing this approach also found a significant increase in vascularity for ears injected with adenovirus encoding a ZFP (black box) as compared to adenovirus encoding green fluorescent protein (gray box).

Neovasculature resulting from activation of the endogenouse VEGF-A gene by the ZFP constructs is not hyperpermeable. Additional ear angiogenesis studies used a modification of a previously described approach (Thurston, G., et al., 2000, Nature Medicine 6:460–463). Briefly, adenovirus vectors encoding either a VEGF-A activating ZFP or murine VEGF164 were injected subcutaneously in the ears of CD-1 mice ($10^8$ pfu in 15 µl volume). Contralateral ears were injected with adenovirus encoding GFP. Digital photographs were obtained after three or six days. Evans Blue dye (200 µl of 4% solution) was injected by tail vein and the distribution in the ears was assessed and photographed three hours later. The mice were then sacrificed, ears embedded in OTC and frozen in liquid nitrogen cooled isopentane. 5µm sections were fixed with cold acetone:methanol, immunostained with a monoclonal anti-PECAM antibody and vessel counts obtained as previously described (Giordano, F. J. et al., 2001, Proc. Natl. Acad. Sci. U.S.A. 98:5780–5785).

VEGF is a potent vascular permeability factor and has been shown to induce hemorrhage and extravasation of intravascular dye in the mouse ear model (Pettersson, A. et al., 2000, Lab. Invest. 80:99–115). Interestingly, when compared to ears similarly treated with an adenovirus encoding murine VEGF164, the ZFP-induced neovasculature was not spontaneously hemorrhagic and was not permeable to Evans Blue dye infusion (see FIG. 22). In other experiments, expression of angiopoietin 1, a growth factor previously shown capable of promoting the growth of a more 'mature' non-leaky neovasculature, was not induced in the VEGF-ZFP treated cells.

As shown in FIG. 22, the neovasculature resulting from ZFP-induced expression of VEGF-A expression was not hyperpermeable as was that produced by murine VEGF164 cDNA expression.

F. Accelerated Wound Healing

Cutaneous wound healing is accelerated by VEGF-A regulating ZFP's.

Bilateral cutaneous wounds were created in the backs of CD-1 mice by excision of a 5 mm circle of skin using a punch bioptome. At the time of wounding, adenovirus encoding a VEGF-A regulating zinc finger protein (MVG) was applied topically to the wound. The contralateral wound was treated by topical application of a control adenovirus encoding green fluorescent protein.

Shown in FIGS. 19A and 19B is an example of how treatment with the VEGF-A regulating ZFP augments the degree of reepithelialization noted at day 5 post-wounding. The arrows denote the leading edge of keratinocyte ingrowth into the wound. As is apparent, and as is shown in the graph of FIG. 19C, the distance between the edges of keratinocyte ingrowth is decreased by VEGF-ZFP treatment; thus reepithelialization is augmented. All measurements were performed using captured digital images and a computer caliper program. The values shown in the graph are relative units.

Wound reepithelialization is augmented by treatment with VEGF-A regulating ZFP's. As depicted in FIGS. 20A and 20B, ingrowth of the leading edge of keratinocytes into the wound is augmented by the topical application of recombinant adenovirus encoding a VEGF-A regulating ZFP (MVG). The arrowheads in the lower left of FIGS. 20A and 20B mark the wound edge and the upper arrow in each figure marks the extent of keratinocyte ingrowth at day 5 post-wounding. This analysis is complementary to the quantitation of the distance between the keratinocyte ingrowth cones noted in FIGS. 19A and 19B.

Treatment of cutaneous wounds by topical application of recombinant adenovirus encoding VEGF-A regulating zinc finger proteins results in angiogenesis and increased vascularity. Cutaneous wounds were treated as just described with either adenovirus encoding a VEGF-A regulating ZFP (MVG) or a control adenovirus encoding green fluorescent protein (GFP). Wounds were fixed, sectioned and immunostained with an antibody against an endothelial cell specific lectin. As shown in FIGS. 21A and 21B, there is increased vascularity in the VEGF-ZFP treated wounds (FIG. 21A) as compared to the control wounds (FIG. 21B). Vessel counts were performed on digitally captured images and represent the average of 5 high power fields per section (n=6 per group). The results with this approach (see FIG. 21C) are consistent with the immunostaining results.

IV. Discussion

The results of the experiments described in this example illustrate the ability to design ZFPs capable of tightly binding to target sites within the promoter region of the VEGF-A gene utilizing the approaches described herein. Certain of the ZFPs were found to bind more tightly to their intended target site then the naturally occurring transcription factor SP1. The ability of these ZFPs to function in vitro was shown by transfecting C 127I cells with constructs encoding the ZFPs and demonstrating increased expression of VEGF-A at both the transcript and expressed protein level.

Using several different accepted model systems for angiogenesis and wound healing, the results from these investigations also show that ZFPs can be utilized to modulate angiogenesis and thus affect a wide variety of conditions that are correlated with blood flow and blood delivery. More specifically, the foregoing results demonstrate that one can regulate angiogenesis by introducing plasmid or viral constructs encoding a ZFP having appropriate binding capability to modulate expression of one or more VEGF genes in vivo and to thereby modulate vessel formation. As an example of the utility of this general approach, the results of certain of the model studies conducted in this example show that introduced ZFPs can significantly accelerate wound reepithelialization and wound healing. Such utility was demonstrated using accepted model systems and by established histological and immunohistological methods. In view of these results, it is expected that the approaches illustrated in this example can be utilized in other treatment applications that are based upon regulation of angiogenesis. By judicious selection of either an appropriate activation domain or repressor domain with the ZFP, one can selectively increase or reduce angiogenesis depending upon the nature of the condition being treated. While this particular set of investigations was conducted using viral or plasmid constructs to introduce ZFPs into a cell, other delivery methods such as described supra can also be utilized. It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entireties for all purposes to the same extent as if each individual publication, patent or patent application were specifically and individually indicated to be so incorporated by reference.

TABLE 1

Regions of VEGF Genes Examined for Potential Target Sites[1]

| A | B[2] | C | D | P1GF[2] | Viral VEGF-E |
|---|---|---|---|---|---|
| −2.3 | −1.0 | −0.60 | −1.0 | −1.0 | −.23 |
| +1.1 | +0.32 | +0.51 | +1.0 | +1.0 | +.62 |

[1]Numbers indicate the number of kilobase pairs upstream (negative number) or downstream (positive number) from the transcriptional start site which were examined.
[2]The P1GF sequence, and the portion of the VEGF-B sequence between −1.0 and −0.4, are based on high-throughput genome sequence data that may be subject to change.

TABLE 2

Locations of Target Site in VEGF Sequences

| ZFP NAME | VEGF A | VEGF B | VEGF C | VEGF D | VEGF E (P1DGF) | Viral VEGF |
|---|---|---|---|---|---|---|
| BVO 13A | +851 | | | | | |
| EP10A | −1083 | −31 | −252 | | | |
|  | +534 | | | | | |
| GATA82Z7678 | −485 | −170 | | | +183 | |
| HBV 3 | +779 | | −245 | | | |
| HP38 4A | −2248 | −119 | +479 | +805 | −29 | |
|  | −1413 | | +510 | | +210 | |
|  | −1055 | | | | | |
|  | −633 | | | | | |
| HUM 17A | −1002 | | | | −33 | |
|  | +472 | | | | | |
| HUM 19A | −1016 | | | | | |
| MTS 5A | −2251 | | | | +213 | |
| MX1E | +851 | | | | | |
| PDF 5A | +590 | | | | −748 | |
| RAT 24A | +711 | | | | | |
| SAN 16A | −1954 | | | | | |
| USX 3A | +554 | | −230 | | | |
|  | +928 | | | | | |
| VEGF 1 | −8 | | | | −454 | |
|  | | | | | −348 | |
|  | | | | | −36 | |
| VEGF 1*3 | −8 | | | | −454 | |
|  | | | | | −348 | |
|  | | | | | −36 | |
| VEGF 1A | −8 | | | | −454 | |
|  | | | | | −348 | |
|  | | | | | −36 | |
| VEGF 1B | −8 | | | | | |
| VEGF 1C | −8 | | | | | |
| VEGF 1D | −8 | | | | | |
| VG 10A | −1412 | −774 | | | | |
|  | −354 | | | | | |
| VG 1B | −2252 | −943 | | | | |
| VG 4A | −1083 | −31 | −252 | | | |
| VG 8A | −2248 | −119 | +479 | +313 | −903 | +575 |
|  | −633 | −784 | +510 | +805 | −29 | |
|  | −475 | | | | −22 | |
|  | −391 | | | | +179 | |
|  | | | | | +210 | |
| VOP 28A-2 | −573 | | +61 | | | |
| VOP 30A-4 | +42 | | −481 | | | |
|  | +530 | | | | | |
| VOP 32A-6 | +434 | | | | | |
| VOP 32B-7 | +434 | | | | | |

TABLE 2-continued

Locations of Target Site in VEGF Sequences

| ZFP NAME | VEGF A | VEGF B | VEGF C | VEGF D | VEGF E (PlDGF) | Viral VEGF |
|---|---|---|---|---|---|---|
| VOP 35A-10 | +892 | | | | | |
| ZEN-7A 1 | −1273 −573 | −945 | +61 | −675 | | |
| BVO 10A-9A | +621 | | | | | |
| BVO 12A-11B | +806 | | | | | |
| BVO 14B-13A | +851 | | | | | |
| VOP 29A-3 | +5 | | | | | |
| VOP 32C | +434 | | | | | |
| VOP 32D | +434 | | | | | |
| VOP 32E | +434 | | | | | |
| VOP 32F | +434 | | | | | |
| VOP 32G | +434 | | | | | |
| VOP 32H | +434 | | | | | |
| VOP 32I | +434 | | | | | |
| VOP 32J | +434 | | | | | |

TABLE 3

Target sites and recognition helix sequences of human VEGF-targeted ZFPs

| ZFP NAME | TARGET | SEQ. ID NO | F 1 | SEQ. ID NO | F 2 | SEQ. ID NO | F 3 | SEQ. ID NO | $K_d$ (nM) |
|---|---|---|---|---|---|---|---|---|---|
| BVO 13A | ATGGACGGG | 1 | RSDHLAR | 30 | DRSNLTR | 59 | RSDALTQ | 88 | <.02 |
| EP10A | KGGGGCTGG | 2 | RSDHLTT | 31 | DRSHLAR | 60 | RSDHLSK | 89 | 0.35 |
| GATA82Z678 | GAGKGKGYG | 3 | RLDSLLR | 32 | DRDHLTR | 61 | RSDNLAR | 90 | 1.8 |
| HBV 3 | GGGGGAGGW | 4 | QTGHLRR | 33 | QSGHLQR | 62 | RSDHLSR | 91 | 30 |
| HP38 4A | GGDTGGGGG | 5 | RSDHLAR | 34 | RSDHLTT | 63 | QRAHLAR | 92 | 0.75 |
| HUM 17A | ARGGGGGAG | 6 | RSDNLAR | 35 | RSDHLSR | 64 | RSDNLTQ | 93 | <.02 |
| HUM 19A | TGGGCAGAC | 7 | DRSNLTR | 36 | QSGDLTR | 65 | RSDHLTT | 94 | 0.02 |
| MTS 5A | TGGGGGTGG | 8 | RSDHLTT | 37 | RSDHLTR | 66 | RSDHLTT | 95 | 0.07 |
| MX1E | ATGGACGGG | 9 | RSDHLAR | 38 | DRSNLTR | 67 | RSDALSA | 96 | 3.4 |
| PDF 5A | GYAGGGGCC | 10 | DRSSLTR | 39 | RSDHLSR | 68 | QSGSLTR | 97 | .23 |
| RAT 24A | GDGGAAGHC | 11 | ERGTLAR | 40 | QSGNLAR | 69 | RSDALAR | 98 | <.02 |
| SAN 16A | AKGGAAGGG | 12 | RSDHLAR | 41 | QSGNLAR | 70 | RSDALRQ | 99 | 1.03 |
| USX 3A | GCCGGGGAG | 13 | RSDNLTR | 42 | RSDHLTR | 71 | DRSDLTR | 100 | 0.06 |
| VEGF 1 | GGGGAGGVK | 14 | TTSNLRR | 43 | RSSNLQR | 72 | RSDHLSR | 101 | 2.83 |
| VEGF 1* | GGGGAGGVK | 15 | TTSNLRR | 44 | RSSNLQR | 73 | RSDHLSR | 102 | 3 |
| VEGF 1A | GGGGAGGVK | 16 | TTSNLRR | 45 | RSDNLQR | 74 | RSDHLSR | 103 | 0.2 |
| VEGF 1B | GGGGAGGAT | 17 | QSSNLAR | 46 | RSDNLQR | 75 | RSDHLSR | 104 | 2 |
| VEGF 1C | GGGGVGGAT | 18 | TTSNLAR | 47 | RSDNLQR | 76 | RSDHLSR | 105 | 1 |
| VEGF 1D | GGGGAGGMT | 19 | QSSNLRR | 48 | RSDNLQR | 77 | RSDHLSR | 106 | 2 |
| VG 10A | GAWGGGGC | 20 | DSGHLTR | 49 | RSDHLTR | 78 | QSGNLTR | 107 | ND |
| VG 1B | ATGGGGGTG | 21 | RSDALTR | 50 | RSDHLTR | 79 | RSDALTQ | 108 | ND |
| VG 4A | GGGGGCTGG | 22 | RSDHLTT | 51 | DRSHLAR | 80 | RSDHLSR | 109 | ND |
| VG 8A | GDGTGGGGN | 23 | QSSHLAR | 52 | RSDHLTT | 81 | RSDALAR | 110 | .35 |
| VOP 28A-2 | GGGGGCGCT | 24 | QSSDLRR | 53 | DRSHLAR | 82 | RSDHLSR | 111 | <.02 |
| VOP 30A-4 | GCTGGGGGC | 25 | DRSHLTR | 54 | RSDHLTR | 83 | QSSDLTR | 112 | <.02 |

TABLE 3-continued

Target sites and recognition helix sequences of human VEGF-targeted ZFPs

| ZFP NAME | TARGET | SEQ. ID NO | F 1 | SEQ. ID NO | F 2 | SEQ. ID NO | F 3 | SEQ. ID NO | $K_d$ (nM) |
|---|---|---|---|---|---|---|---|---|---|
| VOP 32A-6 | GGGGGTGAC | 26 | DRSNLTR | 55 | MSHHLSR | 84 | RSDHLSR | 113 | <.02 |
| VOP 32B-7 | GGGGGTGAC | 27 | DRSNLTR | 56 | TSGHLVR | 85 | RSDHLSR | 114 | <.02 |
| VOP 35A-10 | GCTGGAGCA | 28 | QSGSLTR | 57 | QSGHLQR | 86 | QSSDLTR | 115 | <.02 |
| ZEN-7A 1 | GGGGHGCT | 29 | QSSDLRR | 58 | QSSHLAR | 87 | RSDHLSR | 116 | .63 |
| VOP 29A-3 | GAGGCTTGG | 244 | RSDHLTT | 51 | QSSDLTR | 112 | RSDNLTR | 42 | <.02 |
| VOP 32-C | GGGGGTGAC | 26 | DRSNLTR | 55 | TSGHLTR | 245 | RSDHLSR | 68 | ND |
| VOP 32-D | GGGGGTGAC | 26 | DRSNLTR | 55 | TSGHLIR | 246 | RSDHLSR | 68 | ND |
| VOP 32-E | GGGGGTGAC | 26 | DRSNLTR | 55 | TSGHLSR | 247 | RSDHLSR | 68 | ND |
| VOP 32-F | GGGGGTGAC | 26 | DRSNLTR | 55 | TSGHLAR | 248 | RSDHLSR | 68 | ND |
| VOP 32-G | GGGGGTGAC | 26 | DRSNLTR | 55 | TSGHLRR | 249 | RSDHLSR | 68 | ND |
| VOP 32-H | GGGGGTGAC | 26 | DRSNLTR | 55 | TAGHLVR | 250 | RSDHLSR | 68 | ND |
| VOP 32-I | GGGGGTGAC | 26 | DRSNLTR | 55 | TTGHLVR | 251 | RSDHLSR | 68 | ND |
| VOP 32-J | GGGGGTGAC | 26 | DRSNLTR | 55 | TKDHLVR | 252 | RSDHLSR | 68 | ND |

TABLE 4

Target sites and recognition helix sequences of human VEGF-targeted ZFPs

| ZFP NAME | TARGET | SEQ ID NO | F 1 | SEQ ID NO | F 2 | SEQ ID NO | F 3 | SEQ ID NO | F 4 | SEQ ID NO | F 5 | SEQ ID NO | F 6 | SEQ ID NO |
|---|---|---|---|---|---|---|---|---|---|---|---|---|---|---|
| BVO 10A-9A | GTGGAGGGGTCGGGGCT | 117 | QSSDLRR | 120 | RSDHLTR | 123 | DRSALAR | 126 | RSDHLAR | 129 | RSDNLAR | 132 | RSDALTR | 135 |
| BVO 12A-11B | GGAGAGGGGGCYGCAGTG | 118 | RSDALTR | 121 | QSGDLTR | 124 | ERGDLTR | 127 | RSDHLAR | 130 | RSDNLAR | 133 | QSGHLQR | 136 |
| BVO 14B-13A | ATGGACGGGtGAGGYGGYG | 119 | RSDELTR | 122 | RSDELTR | 125 | RSDNLAR | 128 | RSDHLAR | 131 | DRSNLTR | 134 | RSDALTQ | 137 |

TABLE 6

Vegf-targeted ZFPs

| ZFP Name | Target Sequence 5'–3' | SEQ. ID NO: | Subsites 5'–3' | Finger Designs | SEQ. ID NO: | Apparent Kd (nM) |
|---|---|---|---|---|---|---|
| VZ-950 | GAAGAGGACc | 138 | GACc | EKANLTR | 149 | 0.18 |
|  |  |  | GAGg | RSDNLTR | 150 |  |
|  |  |  | GAAg | QRSNLVR | 151 |  |
| VZ-573 | GGGGGCGCTc | 139 | GCTc | QSSDLRR | 152 | 0.63 |
|  |  |  | GGCg | QSSHLAR | 153 |  |
|  |  |  | GGGg | RSDHLSR | 154 |  |
| VZ-475 | GTGTGGGGTt | 140 | GGTt | QSSHLAR | 155 | 0.35 |
|  |  |  | TGGg | RSDHLTT | 156 |  |
|  |  |  | GTGt | RSDALAR | 157 |  |
| SP1 (−76/+527) | GGGGCGGGGg | 141 | GGGg | KTSHLRA | 158 | 0.25 |
|  |  |  | GCGg | RSDELQR | 159 |  |
|  |  |  | GGGg | RSDHLSK | 160 |  |

TABLE 6-continued

Vegf-targeted ZFPs

| ZFP Name | Target Sequence 5'-3' | SEQ. ID NO: | Subsites 5'-3' | Finger Designs | SEQ. ID NO: | Apparent Kd (nM) |
|---|---|---|---|---|---|---|
| VZ-8 | GGGGAGGATC | 142 | GATc<br>GAGg<br>GGGg | TTSNLRR<br>RSSNLQR<br>RSDHLSR | 161<br>162<br>163 | 2.83 |
| VZ+42 /+530 | GCTGGGGGCt/g | 143 | GGCt/g<br>GGGg<br>GCTg | DRSHLTR<br>RSDHLTR<br>QSSDLTR | 164<br>165<br>166 | <0.02 |
| VZ+434b | GGGGGTGACc | 144 | GACc<br>GGTg<br>GGGg | DRSNLTR<br>TSGHLVR<br>RSDHLSR | 167<br>168<br>169 | <0.02 |
| VZ+434a | GGGGGTGACc | 145 | GACc<br>GGTg<br>GGGg | DRSNLTR<br>MSHHLSR<br>RSDHLSR | 170<br>171<br>172 | <0.02 |
| VZ+472 | AAGGGGGAGg | 146 | GAGg<br>GGGg<br>AAGg | RSDNLAR<br>RSDHLSR<br>RSDNLTQ | 173<br>174<br>175 | 0.006 |
| VZ+590 | GCAGGGGCCg | 147 | GCCg<br>GGGg<br>GCAg | DRSSLTR<br>RSDHLSR<br>QSGSLTR | 176<br>177<br>178 | 0.23 |
| VZ+892 | GCTGGAGCAc | 148 | GCAc<br>GGAg<br>GCTg | QSGSLTR<br>QSGHLQR<br>QSSDLTR | 179<br>180<br>181 | 0.24 |

TABLE 7

Target sites and recognition helix sequences of rat VEGF-targeted ZFPs

| ZFP NAME | TARGET | LOCATION | RECOGNITION HELICES |
|---|---|---|---|
| BV0 12A- 11A | GGAGAGGGGGCCGCAGTG<br>(SEQ ID NO: 182) | +785 | F1: RSDALTR (SEQ ID NO: 186)<br>F2: QSGDLTR (SEQ ID NO: 187)<br>F3: ERGDLTR (SEQ ID NO: 188)<br>F4: RSDHLAP (SEQ ID NO: 189)<br>F5: RSDNLAR (SEQ ID NO: 190)<br>F6: QSSHLAR (SEQ ID NO: 191) |
| BVO 14A- 13B | ATGGACGGGtGAGGCGGCG<br>(SEQ ID NO: 183) | +830 | F1: RSDELTR (SEQ ID NO: 192)<br>F2: RSDELQR (SEQ ID NO: 193)<br>F3: RSDNLAR (SEQ ID NO: 194)<br>F4: RSDHLAR (SEQ ID NO: 195)<br>F5: DRSNLTR (SEQ ID NO: 196)<br>F6: RSDALTQ (SEQ ID NO: 197) |
| VOP 32A | GGGGGTGAC<br>(SEQ ID NO: 184) | +420 | F1: DRSNLTR (SEQ ID NO: 198)<br>F2: MSHHLSR (SEQ ID NO: 199)<br>F3: RSDHLSR (SEQ ID NO: 200) |
| VOP 30A | GCTGGGGGC<br>(SEQ ID NO: 185) | +40<br>+514 | F1: DPSHLTR (SEQ ID NO: 201)<br>F2: RSDHLTR (SEQ ID NO: 202)<br>F3: QSSDLTF (SEQ ID NO: 203) |
| VOP 32B | GGGGGTGAC<br>(SEQ ID NO: 184) | +420 | F1: DRSNLTR (SEQ ID NO: 198)<br>F2: TSGHLVR (SEQ ID NO: 85)<br>F3: RSDHLSR (SEQ ID NO: 200) |

TABLE 8

Nucleotide sequences of probe and primers used for analysis of VEGF-C mRNA

| | SEQUENCE | SEQ ID NO |
|---|---|---|
| VEGF-C-Forward primer | 5'-TGCCGATGCATGTCTAAACT-3' | 204 |
| VEGF-C-Reverse primer | 5'-TGAACAGGTCTCTTCATCCAGC-3' | 205 |
| VEGF-C-Probe | 5'-FAM-CAGCAACACTACCACAGTGTCAGGCA-TAMRA-3' | 206 |

What is claimed is:

1. A purified nucleic acid encoding a polypeptide, wherein the polypeptide comprises a zinc finger protein that binds to a target site in a VEGF gene so as to modulate expression of the VEGF gene, thereby modulating angiogenesis, wherein the zinc finger protein comprises first, second and third fingers comprising segments of amino acids specified in SEQ ID NOS: 55, 247 and 68 respectively.

2. A nucleic acid according to claim 1, wherein the zinc finger protein is a fusion protein comprising a regulatory domain.

3. A vector comprising the nucleic acid of claim 1.

4. A composition for modulation of angiogenesis comprising
   (a) a nucleic acid according to claim 1 operably linked to a regulatory sequence, wherein the regulatory sequence allows for expression of the nucleic acid in a cell; and
   (b) a pharmaceutically acceptable carrier or diluent.

5. The composition according to claim 4, wherein the nucleic acid is contained in an expression vector.

6. The composition according to claim 5, wherein the expression vector is a viral expression vector.

7. The composition according to claim 6, wherein the expression vector is selected from the group consisting of a retroviral expression vector, an adenoviral expression vector, and an AAV expression vector.

* * * * *

SEQUENCE LISTING

<160> NUMBER OF SEQ ID NOS: 252

<210> SEQ ID NO 1
<211> LENGTH: 9
<212> TYPE: DNA
<213> ORGANISM: Artificial Sequence
<220> FEATURE:
<223> OTHER INFORMATION: target

<400> SEQUENCE: 1 atggacggg                                                                9

<210> SEQ ID NO 2
<211> LENGTH: 9
<212> TYPE: DNA
<213> ORGANISM: Artificial Sequence
<220> FEATURE:
<223> OTHER INFORMATION: target

<400> SEQUENCE: 2 kggggctgg                                                                9

<210> SEQ ID NO 3
<211> LENGTH: 9
<212> TYPE: DNA
<213> ORGANISM: Artificial Sequence
<220> FEATURE:
<223> OTHER INFORMATION: target

<400> SEQUENCE: 3 gagkgkgyg                                                                9

<210> SEQ ID NO 4
<211> LENGTH: 9
<212> TYPE: DNA
<213> ORGANISM: Artificial Sequence
<220> FEATURE:
<223> OTHER INFORMATION: target

<400> SEQUENCE: 4 gggggaggw                                                                9

<210> SEQ ID NO 5
<211> LENGTH: 9
<212> TYPE: DNA
<213> ORGANISM: Artificial Sequence
<220> FEATURE:
<223> OTHER INFORMATION: target

<400> SEQUENCE: 5 ggdtggggg                                                                9

<210> SEQ ID NO 6
<211> LENGTH: 9
<212> TYPE: DNA
<213> ORGANISM: Artificial Sequence
<220> FEATURE:
<223> OTHER INFORMATION: target

<400> SEQUENCE: 6 argggggag                                                                9

<210> SEQ ID NO 7
<211> LENGTH: 9

```
<212> TYPE: DNA
<213> ORGANISM: Artificial Sequence
<220> FEATURE:
<223> OTHER INFORMATION: target

<400> SEQUENCE: 7 tgggcagac                                                                    9

<210> SEQ ID NO 8
<211> LENGTH: 9
<212> TYPE: DNA
<213> ORGANISM: Artificial Sequence
<220> FEATURE:
<223> OTHER INFORMATION: target

<400> SEQUENCE: 8 tgggggtgg                                                                    9

<210> SEQ ID NO 9
<211> LENGTH: 9
<212> TYPE: DNA
<213> ORGANISM: Artificial Sequence
<220> FEATURE:
<223> OTHER INFORMATION: target

<400> SEQUENCE: 9 atggacggg                                                                    9

<210> SEQ ID NO 10
<211> LENGTH: 9
<212> TYPE: DNA
<213> ORGANISM: Artificial Sequence
<220> FEATURE:
<223> OTHER INFORMATION: target

<400> SEQUENCE: 10 gyaggggcc                                                                    9

<210> SEQ ID NO 11
<211> LENGTH: 9
<212> TYPE: DNA
<213> ORGANISM: Artificial Sequence
<220> FEATURE:
<223> OTHER INFORMATION: target

<400> SEQUENCE: 11 gdggaaghc                                                                    9

<210> SEQ ID NO 12
<211> LENGTH: 9
<212> TYPE: DNA
<213> ORGANISM: Artificial Sequence
<220> FEATURE:
<223> OTHER INFORMATION: target

<400> SEQUENCE: 12 akggaaggg                                                                    9

<210> SEQ ID NO 13
<211> LENGTH: 9
<212> TYPE: DNA
<213> ORGANISM: Artificial Sequence
<220> FEATURE:
<223> OTHER INFORMATION: target

<400> SEQUENCE: 13
```

```
gccggggag                                                          9

<210> SEQ ID NO 14
<211> LENGTH: 9
<212> TYPE: DNA
<213> ORGANISM: Artificial Sequence
<220> FEATURE:
<223> OTHER INFORMATION: target

<400> SEQUENCE: 14 gggaggvk                                                           9

<210> SEQ ID NO 15
<211> LENGTH: 9
<212> TYPE: DNA
<213> ORGANISM: Artificial Sequence
<220> FEATURE:
<223> OTHER INFORMATION: target

<400> SEQUENCE: 15 ggggaggvk                                                          9

<210> SEQ ID NO 16
<211> LENGTH: 9
<212> TYPE: DNA
<213> ORGANISM: Artificial Sequence
<220> FEATURE:
<223> OTHER INFORMATION: target

<400> SEQUENCE: 16 ggggaggvk                                                          9

<210> SEQ ID NO 17
<211> LENGTH: 9
<212> TYPE: DNA
<213> ORGANISM: Artificial Sequence
<220> FEATURE:
<223> OTHER INFORMATION: target

<400> SEQUENCE: 17 ggggaggat                                                          9

<210> SEQ ID NO 18
<211> LENGTH: 9
<212> TYPE: DNA
<213> ORGANISM: Artificial Sequence
<220> FEATURE:
<223> OTHER INFORMATION: target

<400> SEQUENCE: 18 ggggvggat                                                          9

<210> SEQ ID NO 19
<211> LENGTH: 9
<212> TYPE: DNA
<213> ORGANISM: Artificial Sequence
<220> FEATURE:
<223> OTHER INFORMATION: target

<400> SEQUENCE: 19 ggggaggmt                                                          9

<210> SEQ ID NO 20
<211> LENGTH: 9
<212> TYPE: DNA
<213> ORGANISM: Artificial Sequence
```

```
<220> FEATURE:
<223> OTHER INFORMATION: target

<400> SEQUENCE: 20 gawgggggc                                                                        9

<210> SEQ ID NO 21
<211> LENGTH: 9
<212> TYPE: DNA
<213> ORGANISM: Artificial Sequence
<220> FEATURE:
<223> OTHER INFORMATION: target

<400> SEQUENCE: 21 atgggggtg                                                                        9

<210> SEQ ID NO 22
<211> LENGTH: 9
<212> TYPE: DNA
<213> ORGANISM: Artificial Sequence
<220> FEATURE:
<223> OTHER INFORMATION: target

<400> SEQUENCE: 22 gggggctgg                                                                        9

<210> SEQ ID NO 23
<211> LENGTH: 9
<212> TYPE: DNA
<213> ORGANISM: Artificial Sequence
<220> FEATURE:
<223> OTHER INFORMATION: target
<221> NAME/KEY: misc_feature
<222> LOCATION: (9)...(9)
<223> OTHER INFORMATION: n = g, a, c, or t

<400> SEQUENCE: 23 gdgtggggn                                                                        9

<210> SEQ ID NO 24
<211> LENGTH: 9
<212> TYPE: DNA
<213> ORGANISM: Artificial Sequence
<220> FEATURE:
<223> OTHER INFORMATION: target

<400> SEQUENCE: 24 gggggcgct                                                                        9

<210> SEQ ID NO 25
<211> LENGTH: 9
<212> TYPE: DNA
<213> ORGANISM: Artificial Sequence
<220> FEATURE:
<223> OTHER INFORMATION: target

<400> SEQUENCE: 25 gctgggggc                                                                        9

<210> SEQ ID NO 26
<211> LENGTH: 9
<212> TYPE: DNA
<213> ORGANISM: Artificial Sequence
<220> FEATURE:
<223> OTHER INFORMATION: target

<400> SEQUENCE: 26
```

```
gggggtgac                                                               9

<210> SEQ ID NO 27
<211> LENGTH: 9
<212> TYPE: DNA
<213> ORGANISM: Artificial Sequence
<220> FEATURE:
<223> OTHER INFORMATION: target

<400> SEQUENCE: 27 ggggdtgac                                                               9

<210> SEQ ID NO 28
<211> LENGTH: 9
<212> TYPE: DNA
<213> ORGANISM: Artificial Sequence
<220> FEATURE:
<223> OTHER INFORMATION: target

<400> SEQUENCE: 28 gctggagca                                                               9

<210> SEQ ID NO 29
<211> LENGTH: 9
<212> TYPE: DNA
<213> ORGANISM: Artificial Sequence
<220> FEATURE:
<223> OTHER INFORMATION: target

<400> SEQUENCE: 29 ggggghgct                                                               9

<210> SEQ ID NO 30
<211> LENGTH: 7
<212> TYPE: PRT
<213> ORGANISM: Artificial Sequence
<220> FEATURE:
<223> OTHER INFORMATION: finger

<400> SEQUENCE: 30

Arg Ser Asp His Leu Ala Arg
 1               5

<210> SEQ ID NO 31
<211> LENGTH: 7
<212> TYPE: PRT
<213> ORGANISM: Artificial Sequence
<220> FEATURE:
<223> OTHER INFORMATION: finger

<400> SEQUENCE: 31

Arg Ser Asp His Leu Thr Thr
 1               5

<210> SEQ ID NO 32
<211> LENGTH: 7
<212> TYPE: PRT
<213> ORGANISM: Artificial Sequence
<220> FEATURE:
<223> OTHER INFORMATION: finger

<400> SEQUENCE: 32

Arg Leu Asp Ser Leu Leu Arg
 1               5
```

```
<210> SEQ ID NO 33
<211> LENGTH: 7
<212> TYPE: PRT
<213> ORGANISM: Artificial Sequence
<220> FEATURE:
<223> OTHER INFORMATION: finger

<400> SEQUENCE: 33

Gln Thr Gly His Leu Arg Arg
1               5

<210> SEQ ID NO 34
<211> LENGTH: 7
<212> TYPE: PRT
<213> ORGANISM: Artificial Sequence
<220> FEATURE:
<223> OTHER INFORMATION: finger

<400> SEQUENCE: 34

Arg Ser Asp His Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: finger

<400> SEQUENCE: 35

Arg Ser Asp Asn Leu Ala Arg
1               5

<210> SEQ ID NO 36
<211> LENGTH: 7
<212> TYPE: PRT
<213> ORGANISM: Artificial Sequence
<220> FEATURE:
<223> OTHER INFORMATION: finger

<400> SEQUENCE: 36

Asp Arg Ser Asn Leu Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: finger

<400> SEQUENCE: 37

Arg Ser Asp His Leu Thr Thr
1               5

<210> SEQ ID NO 38
<211> LENGTH: 7
<212> TYPE: PRT
<213> ORGANISM: Artificial Sequence
<220> FEATURE:
<223> OTHER INFORMATION: finger

<400> SEQUENCE: 38

Arg Ser Asp His Leu Ala Arg
1               5

<210> SEQ ID NO 39
```

```
<211> LENGTH: 7
<212> TYPE: PRT
<213> ORGANISM: Artificial Sequence
<220> FEATURE:
<223> OTHER INFORMATION: finger

<400> SEQUENCE: 39

Asp Arg Ser Ser Leu Thr Arg
 1               5

<210> SEQ ID NO 40
<211> LENGTH: 7
<212> TYPE: PRT
<213> ORGANISM: Artificial Sequence
<220> FEATURE:
<223> OTHER INFORMATION: finger

<400> SEQUENCE: 40

Glu Arg Gly Thr Leu Ala Arg
 1               5

<210> SEQ ID NO 41
<211> LENGTH: 7
<212> TYPE: PRT
<213> ORGANISM: Artificial Sequence
<220> FEATURE:
<223> OTHER INFORMATION: finger

<400> SEQUENCE: 41

Arg Ser Asp His Leu Ala Arg
 1               5

<210> SEQ ID NO 42
<211> LENGTH: 7
<212> TYPE: PRT
<213> ORGANISM: Artificial Sequence
<220> FEATURE:
<223> OTHER INFORMATION: finger

<400> SEQUENCE: 42

Arg Ser Asp Asn Leu Thr Arg
 1               5

<210> SEQ ID NO 43
<211> LENGTH: 7
<212> TYPE: PRT
<213> ORGANISM: Artificial Sequence
<220> FEATURE:
<223> OTHER INFORMATION: finger

<400> SEQUENCE: 43

Thr Thr Ser Asn Leu Arg Arg
 1               5

<210> SEQ ID NO 44
<211> LENGTH: 7
<212> TYPE: PRT
<213> ORGANISM: Artificial Sequence
<220> FEATURE:
<223> OTHER INFORMATION: finger

<400> SEQUENCE: 44

Thr Thr Ser Asn Leu Arg Arg
 1               5

<210> SEQ ID NO 45
<211> LENGTH: 7
```

```
<212> TYPE: PRT
<213> ORGANISM: Artificial Sequence
<220> FEATURE:
<223> OTHER INFORMATION: finger

<400> SEQUENCE: 45

Thr Thr Ser Asn Leu Arg Arg
 1               5

<210> SEQ ID NO 46
<211> LENGTH: 7
<212> TYPE: PRT
<213> ORGANISM: Artificial Sequence
<220> FEATURE:
<223> OTHER INFORMATION: finger

<400> SEQUENCE: 46

Gln Ser Ser Asn Leu Ala Arg
 1               5

<210> SEQ ID NO 47
<211> LENGTH: 7
<212> TYPE: PRT
<213> ORGANISM: Artificial Sequence
<220> FEATURE:
<223> OTHER INFORMATION: finger

<400> SEQUENCE: 47

Thr Thr Ser Asn Leu Ala Arg
 1               5

<210> SEQ ID NO 48
<211> LENGTH: 7
<212> TYPE: PRT
<213> ORGANISM: Artificial Sequence
<220> FEATURE:
<223> OTHER INFORMATION: finger

<400> SEQUENCE: 48

Gln Ser Ser Asn Leu Arg Arg
 1               5

<210> SEQ ID NO 49
<211> LENGTH: 7
<212> TYPE: PRT
<213> ORGANISM: Artificial Sequence
<220> FEATURE:
<223> OTHER INFORMATION: finger

<400> SEQUENCE: 49

Asp Ser Gly His Leu Thr Arg
 1               5

<210> SEQ ID NO 50
<211> LENGTH: 7
<212> TYPE: PRT
<213> ORGANISM: Artificial Sequence
<220> FEATURE:
<223> OTHER INFORMATION: finger

<400> SEQUENCE: 50

Arg Ser Asp Ala Leu Thr Arg
 1               5

<210> SEQ ID NO 51
<211> LENGTH: 7
<212> TYPE: PRT
```

```
<213> ORGANISM: Artificial Sequence
<220> FEATURE:
<223> OTHER INFORMATION: finger

<400> SEQUENCE: 51

Arg Ser Asp His Leu Thr Thr
1               5

<210> SEQ ID NO 52
<211> LENGTH: 7
<212> TYPE: PRT
<213> ORGANISM: Artificial Sequence
<220> FEATURE:
<223> OTHER INFORMATION: finger

<400> SEQUENCE: 52

Gln Ser Ser His Leu Ala Arg
1               5

<210> SEQ ID NO 53
<211> LENGTH: 7
<212> TYPE: PRT
<213> ORGANISM: Artificial Sequence
<220> FEATURE:
<223> OTHER INFORMATION: finger

<400> SEQUENCE: 53

Gln Ser Ser Asp Leu Arg Arg
1               5

<210> SEQ ID NO 54
<211> LENGTH: 7
<212> TYPE: PRT
<213> ORGANISM: Artificial Sequence
<220> FEATURE:
<223> OTHER INFORMATION: finger

<400> SEQUENCE: 54

Asp Arg Ser His Leu Thr Arg
1               5

<210> SEQ ID NO 55
<211> LENGTH: 7
<212> TYPE: PRT
<213> ORGANISM: Artificial Sequence
<220> FEATURE:
<223> OTHER INFORMATION: finger

<400> SEQUENCE: 55

Asp Arg Ser Asn Leu Thr Arg
1               5

<210> SEQ ID NO 56
<211> LENGTH: 7
<212> TYPE: PRT
<213> ORGANISM: Artificial Sequence
<220> FEATURE:
<223> OTHER INFORMATION: finger

<400> SEQUENCE: 56

Asp Arg Ser Asn Leu Thr Arg
1               5

<210> SEQ ID NO 57
<211> LENGTH: 7
<212> TYPE: PRT
<213> ORGANISM: Artificial Sequence
```

```
<220> FEATURE:
<223> OTHER INFORMATION: finger

<400> SEQUENCE: 57

Gln Ser Gly Ser Leu Thr Arg
  1               5

<210> SEQ ID NO 58
<211> LENGTH: 7
<212> TYPE: PRT
<213> ORGANISM: Artificial Sequence
<220> FEATURE:
<223> OTHER INFORMATION: finger

<400> SEQUENCE: 58

Gln Ser Ser Asp Leu Arg Arg
  1               5

<210> SEQ ID NO 59
<211> LENGTH: 7
<212> TYPE: PRT
<213> ORGANISM: Artificial Sequence
<220> FEATURE:
<223> OTHER INFORMATION: finger

<400> SEQUENCE: 59

Asp Arg Ser Asn Leu Thr Arg
  1               5

<210> SEQ ID NO 60
<211> LENGTH: 7
<212> TYPE: PRT
<213> ORGANISM: Artificial Sequence
<220> FEATURE:
<223> OTHER INFORMATION: finger

<400> SEQUENCE: 60

Asp Arg Ser His Leu Ala Arg
  1               5

<210> SEQ ID NO 61
<211> LENGTH: 7
<212> TYPE: PRT
<213> ORGANISM: Artificial Sequence
<220> FEATURE:
<223> OTHER INFORMATION: finger

<400> SEQUENCE: 61

Asp Arg Asp His Leu Thr Arg
  1               5

<210> SEQ ID NO 62
<211> LENGTH: 7
<212> TYPE: PRT
<213> ORGANISM: Artificial Sequence
<220> FEATURE:
<223> OTHER INFORMATION: finger

<400> SEQUENCE: 62

Gln Ser Gly His Leu Gln Arg
  1               5

<210> SEQ ID NO 63
<211> LENGTH: 7
<212> TYPE: PRT
<213> ORGANISM: Artificial Sequence
<220> FEATURE:
```

<223> OTHER INFORMATION: finger

<400> SEQUENCE: 63

Arg Ser Asp His Leu Thr Thr
1               5

<210> SEQ ID NO 64
<211> LENGTH: 7
<212> TYPE: PRT
<213> ORGANISM: Artificial Sequence
<220> FEATURE:
<223> OTHER INFORMATION: finger

<400> SEQUENCE: 64

Arg Ser Asp His Leu Ser Arg
1               5

<210> SEQ ID NO 65
<211> LENGTH: 7
<212> TYPE: PRT
<213> ORGANISM: Artificial Sequence
<220> FEATURE:
<223> OTHER INFORMATION: finger

<400> SEQUENCE: 65

Gln Ser Gly Asp Leu Thr Arg
1               5

<210> SEQ ID NO 66
<211> LENGTH: 7
<212> TYPE: PRT
<213> ORGANISM: Artificial Sequence
<220> FEATURE:
<223> OTHER INFORMATION: finger

<400> SEQUENCE: 66

Arg Ser Asp His Leu Thr Arg
1               5

<210> SEQ ID NO 67
<211> LENGTH: 7
<212> TYPE: PRT
<213> ORGANISM: Artificial Sequence
<220> FEATURE:
<223> OTHER INFORMATION: finger

<400> SEQUENCE: 67

Asp Arg Ser Asn Leu Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: finger

<400> SEQUENCE: 68

Arg Ser Asp His Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: finger

```
<400> SEQUENCE: 69

Gln Ser Gly Asn Leu Ala Arg
 1               5

<210> SEQ ID NO 71
<211> LENGTH: 7
<212> TYPE: PRT
<213> ORGANISM: Artificial Sequence
<220> FEATURE:
<223> OTHER INFORMATION: finger

<400> SEQUENCE: 70

Gln Ser Gly Asn Leu Ala Arg
 1               5

<210> SEQ ID NO 71
<211> LENGTH: 7
<212> TYPE: PRT
<213> ORGANISM: Artificial Sequence
<220> FEATURE:
<223> OTHER INFORMATION: finger

<400> SEQUENCE: 71

Arg Ser Asp His Leu Thr Arg
 1               5

<210> SEQ ID NO 72
<211> LENGTH: 7
<212> TYPE: PRT
<213> ORGANISM: Artificial Sequence
<220> FEATURE:
<223> OTHER INFORMATION: finger

<400> SEQUENCE: 72

Arg Ser Ser Asn Leu Gln Arg
 1               5

<210> SEQ ID NO 73
<211> LENGTH: 7
<212> TYPE: PRT
<213> ORGANISM: Artificial Sequence
<220> FEATURE:
<223> OTHER INFORMATION: finger

<400> SEQUENCE: 73

Arg Ser Ser Asn Leu Gln Arg
 1               5

<210> SEQ ID NO 74
<211> LENGTH: 7
<212> TYPE: PRT
<213> ORGANISM: Artificial Sequence
<220> FEATURE:
<223> OTHER INFORMATION: finger

<400> SEQUENCE: 74

Arg Ser Asp Asn Leu Gln Arg
 1               5

<210> SEQ ID NO 75
<211> LENGTH: 7
<212> TYPE: PRT
<213> ORGANISM: Artificial Sequence
<220> FEATURE:
<223> OTHER INFORMATION: finger
```

```
<400> SEQUENCE: 75

Arg Ser Asp Asn Leu Gln Arg
1               5

<210> SEQ ID NO 76
<211> LENGTH: 7
<212> TYPE: PRT
<213> ORGANISM: Artificial Sequence
<220> FEATURE:
<223> OTHER INFORMATION: finger

<400> SEQUENCE: 76

Arg Ser Asp Asn Leu Gln Arg
1               5

<210> SEQ ID NO 77
<211> LENGTH: 7
<212> TYPE: PRT
<213> ORGANISM: Artificial Sequence
<220> FEATURE:
<223> OTHER INFORMATION: finger

<400> SEQUENCE: 77

Arg Ser Asp Asn Leu Gln Arg
1               5

<210> SEQ ID NO 78
<211> LENGTH: 7
<212> TYPE: PRT
<213> ORGANISM: Artificial Sequence
<220> FEATURE:
<223> OTHER INFORMATION: finger

<400> SEQUENCE: 78

Arg Ser Asp His Leu Thr Arg
1               5

<210> SEQ ID NO 79
<211> LENGTH: 7
<212> TYPE: PRT
<213> ORGANISM: Artificial Sequence
<220> FEATURE:
<223> OTHER INFORMATION: finger

<400> SEQUENCE: 79

Arg Ser Asp His Leu Thr Arg
1               5

<210> SEQ ID NO 80
<211> LENGTH: 7
<212> TYPE: PRT
<213> ORGANISM: Artificial Sequence
<220> FEATURE:
<223> OTHER INFORMATION: finger

<400> SEQUENCE: 80

Asp Arg Ser His Leu Ala Arg
1               5

<210> SEQ ID NO 81
<211> LENGTH: 7
<212> TYPE: PRT
<213> ORGANISM: Artificial Sequence
<220> FEATURE:
<223> OTHER INFORMATION: finger

<400> SEQUENCE: 81
```

Arg Ser Asp His Leu Thr Thr
1               5

<210> SEQ ID NO 82
<211> LENGTH: 7
<212> TYPE: PRT
<213> ORGANISM: Artificial Sequence
<220> FEATURE:
<223> OTHER INFORMATION: finger

<400> SEQUENCE: 82

Asp Arg Ser His Leu Ala Arg
1               5

<210> SEQ ID NO 83
<211> LENGTH: 7
<212> TYPE: PRT
<213> ORGANISM: Artificial Sequence
<220> FEATURE:
<223> OTHER INFORMATION: finger

<400> SEQUENCE: 83

Arg Ser Asp His Leu Thr Arg
1               5

<210> SEQ ID NO 84
<211> LENGTH: 7
<212> TYPE: PRT
<213> ORGANISM: Artificial Sequence
<220> FEATURE:
<223> OTHER INFORMATION: finger

<400> SEQUENCE: 84

Met Ser His His Leu Ser Arg
1               5

<210> SEQ ID NO 85
<211> LENGTH: 7
<212> TYPE: PRT
<213> ORGANISM: Artificial Sequence
<220> FEATURE:
<223> OTHER INFORMATION: finger

<400> SEQUENCE: 85

Thr Ser Gly His Leu Val Arg
1               5

<210> SEQ ID NO 86
<211> LENGTH: 7
<212> TYPE: PRT
<213> ORGANISM: Artificial Sequence
<220> FEATURE:
<223> OTHER INFORMATION: finger

<400> SEQUENCE: 86

Gln Ser Gly His Leu Gln Arg
1               5

<210> SEQ ID NO 87
<211> LENGTH: 7
<212> TYPE: PRT
<213> ORGANISM: Artificial Sequence
<220> FEATURE:
<223> OTHER INFORMATION: finger

<400> SEQUENCE: 87

-continued

```
Gln Ser Ser His Leu Ala Arg
1               5

<210> SEQ ID NO 88
<211> LENGTH: 7
<212> TYPE: PRT
<213> ORGANISM: Artificial Sequence
<220> FEATURE:
<223> OTHER INFORMATION: finger

<400> SEQUENCE: 88

Arg Ser Asp Ala Leu Thr Gln
1               5

<210> SEQ ID NO 89
<211> LENGTH: 7
<212> TYPE: PRT
<213> ORGANISM: Artificial Sequence
<220> FEATURE:
<223> OTHER INFORMATION: finger

<400> SEQUENCE: 89

Arg Ser Asp His Leu Ser Lys
1               5

<210> SEQ ID NO 90
<211> LENGTH: 7
<212> TYPE: PRT
<213> ORGANISM: Artificial Sequence
<220> FEATURE:
<223> OTHER INFORMATION: finger

<400> SEQUENCE: 90

Arg Ser Asp Asn Leu Ala Arg
1               5

<210> SEQ ID NO 91
<211> LENGTH: 7
<212> TYPE: PRT
<213> ORGANISM: Artificial Sequence
<220> FEATURE:
<223> OTHER INFORMATION: finger

<400> SEQUENCE: 91

Arg Ser Asp His Leu Ser Arg
1               5

<210> SEQ ID NO 92
<211> LENGTH: 7
<212> TYPE: PRT
<213> ORGANISM: Artificial Sequence
<220> FEATURE:
<223> OTHER INFORMATION: finger

<400> SEQUENCE: 92

Gln Arg Ala His Leu Ala Arg
1               5

<210> SEQ ID NO 93
<211> LENGTH: 7
<212> TYPE: PRT
<213> ORGANISM: Artificial Sequence
<220> FEATURE:
<223> OTHER INFORMATION: finger

<400> SEQUENCE: 93

Arg Ser Asp Asn Leu Thr Gln
```

-continued

<210> SEQ ID NO 94
<211> LENGTH: 7
<212> TYPE: PRT
<213> ORGANISM: Artificial Sequence
<220> FEATURE:
<223> OTHER INFORMATION: finger

<400> SEQUENCE: 94

Arg Ser Asp His Leu Thr Thr
1               5

<210> SEQ ID NO 95
<211> LENGTH: 7
<212> TYPE: PRT
<213> ORGANISM: Artificial Sequence
<220> FEATURE:
<223> OTHER INFORMATION: finger

<400> SEQUENCE: 95

Arg Ser Asp His Leu Thr Thr
1               5

<210> SEQ ID NO 96
<211> LENGTH: 7
<212> TYPE: PRT
<213> ORGANISM: Artificial Sequence
<220> FEATURE:
<223> OTHER INFORMATION: finger

<400> SEQUENCE: 96

Arg Ser Asp Ala Leu Ser Ala
1               5

<210> SEQ ID NO 97
<211> LENGTH: 7
<212> TYPE: PRT
<213> ORGANISM: Artificial Sequence
<220> FEATURE:
<223> OTHER INFORMATION: finger

<400> SEQUENCE: 97

Gln Ser Gly Ser Leu Thr Arg
1               5

<210> SEQ ID NO 98
<211> LENGTH: 7
<212> TYPE: PRT
<213> ORGANISM: Artificial Sequence
<220> FEATURE:
<223> OTHER INFORMATION: finger

<400> SEQUENCE: 98

Arg Ser Asp Ala Leu Ala Arg
1               5

<210> SEQ ID NO 99
<211> LENGTH: 7
<212> TYPE: PRT
<213> ORGANISM: Artificial Sequence
<220> FEATURE:
<223> OTHER INFORMATION: finger

<400> SEQUENCE: 99

Arg Ser Asp Ala Leu Arg Gln
1               5

<210> SEQ ID NO 100
<211> LENGTH: 7
<212> TYPE: PRT
<213> ORGANISM: Artificial Sequence
<220> FEATURE:
<223> OTHER INFORMATION: finger

<400> SEQUENCE: 100

Asp Arg Ser Asp Leu Thr Arg
1               5

<210> SEQ ID NO 101
<211> LENGTH: 7
<212> TYPE: PRT
<213> ORGANISM: Artificial Sequence
<220> FEATURE:
<223> OTHER INFORMATION: finger

<400> SEQUENCE: 101

Arg Ser Asp His Leu Ser Arg
1               5

<210> SEQ ID NO 102
<211> LENGTH: 7
<212> TYPE: PRT
<213> ORGANISM: Artificial Sequence
<220> FEATURE:
<223> OTHER INFORMATION: finger

<400> SEQUENCE: 102

Arg Ser Asp His Leu Ser Arg
1               5

<210> SEQ ID NO 103
<211> LENGTH: 7
<212> TYPE: PRT
<213> ORGANISM: Artificial Sequence
<220> FEATURE:
<223> OTHER INFORMATION: finger

<400> SEQUENCE: 103

Arg Ser Asp His Leu Ser Arg
1               5

<210> SEQ ID NO 104
<211> LENGTH: 7
<212> TYPE: PRT
<213> ORGANISM: Artificial Sequence
<220> FEATURE:
<223> OTHER INFORMATION: finger

<400> SEQUENCE: 104

Arg Ser Asp His Leu Ser Arg
1               5

<210> SEQ ID NO 105
<211> LENGTH: 7
<212> TYPE: PRT
<213> ORGANISM: Artificial Sequence
<220> FEATURE:
<223> OTHER INFORMATION: finger

<400> SEQUENCE: 105

Arg Ser Asp His Leu Ser Arg
1               5

```
<210> SEQ ID NO 106
<211> LENGTH: 7
<212> TYPE: PRT
<213> ORGANISM: Artificial Sequence
<220> FEATURE:
<223> OTHER INFORMATION: finger

<400> SEQUENCE: 106

Arg Ser Asp His Leu Ser Arg
 1               5

<210> SEQ ID NO 107
<211> LENGTH: 7
<212> TYPE: PRT
<213> ORGANISM: Artificial Sequence
<220> FEATURE:
<223> OTHER INFORMATION: finger

<400> SEQUENCE: 107

Gln Ser Gly Asn Leu Thr Arg
 1               5

<210> SEQ ID NO 108
<211> LENGTH: 7
<212> TYPE: PRT
<213> ORGANISM: Artificial Sequence
<220> FEATURE:
<223> OTHER INFORMATION: finger

<400> SEQUENCE: 108

Arg Ser Asp Ala Leu Thr Gln
 1               5

<210> SEQ ID NO 109
<211> LENGTH: 7
<212> TYPE: PRT
<213> ORGANISM: Artificial Sequence
<220> FEATURE:
<223> OTHER INFORMATION: finger

<400> SEQUENCE: 109

Arg Ser Asp His Leu Ser Arg
 1               5

<210> SEQ ID NO 110
<211> LENGTH: 7
<212> TYPE: PRT
<213> ORGANISM: Artificial Sequence
<220> FEATURE:
<223> OTHER INFORMATION: finger

<400> SEQUENCE: 110

Arg Ser Asp Ala Leu Ala Arg
 1               5

<210> SEQ ID NO 111
<211> LENGTH: 7
<212> TYPE: PRT
<213> ORGANISM: Artificial Sequence
<220> FEATURE:
<223> OTHER INFORMATION: finger

<400> SEQUENCE: 111

Arg Ser Asp His Leu Ser Arg
 1               5
```

```
<210> SEQ ID NO 112
<211> LENGTH: 7
<212> TYPE: PRT
<213> ORGANISM: Artificial Sequence
<220> FEATURE:
<223> OTHER INFORMATION: finger

<400> SEQUENCE: 112

Gln Ser Ser Asp Leu Thr Arg
 1               5

<210> SEQ ID NO 113
<211> LENGTH: 7
<212> TYPE: PRT
<213> ORGANISM: Artificial Sequence
<220> FEATURE:
<223> OTHER INFORMATION: finger

<400> SEQUENCE: 113

Arg Ser Asp His Leu Ser Arg
 1               5

<210> SEQ ID NO 114
<211> LENGTH: 7
<212> TYPE: PRT
<213> ORGANISM: Artificial Sequence
<220> FEATURE:
<223> OTHER INFORMATION: finger

<400> SEQUENCE: 114

Arg Ser Asp His Leu Ser Arg
 1               5

<210> SEQ ID NO 115
<211> LENGTH: 7
<212> TYPE: PRT
<213> ORGANISM: Artificial Sequence
<220> FEATURE:
<223> OTHER INFORMATION: finger

<400> SEQUENCE: 115

Gln Ser Ser Asp Leu Thr Arg
 1               5

<210> SEQ ID NO 116
<211> LENGTH: 7
<212> TYPE: PRT
<213> ORGANISM: Artificial Sequence
<220> FEATURE:
<223> OTHER INFORMATION: finger

<400> SEQUENCE: 116

Arg Ser Asp His Leu Ser Arg
 1               5

<210> SEQ ID NO 117
<211> LENGTH: 18
<212> TYPE: DNA
<213> ORGANISM: Artificial Sequence
<220> FEATURE:
<223> OTHER INFORMATION: target

<400> SEQUENCE: 117
gtggaggggg tcggggct                                                  18

<210> SEQ ID NO 118
<211> LENGTH: 18
```

```
<212> TYPE: DNA
<213> ORGANISM: Artificial Sequence
<220> FEATURE:
<223> OTHER INFORMATION: target

<400> SEQUENCE: 118
ggagaggggg cygcagtg                                                    18

<210> SEQ ID NO 119
<211> LENGTH: 19
<212> TYPE: DNA
<213> ORGANISM: Artificial Sequence
<220> FEATURE:
<223> OTHER INFORMATION: target

<400> SEQUENCE: 119
atggacgggt gaggyggyg                                                   19

<210> SEQ ID NO 120
<211> LENGTH: 7
<212> TYPE: PRT
<213> ORGANISM: Artificial Sequence
<220> FEATURE:
<223> OTHER INFORMATION: finger

<400> SEQUENCE: 120

Gln Ser Ser Asp Leu Arg Arg
 1               5

<210> SEQ ID NO 121
<211> LENGTH: 7
<212> TYPE: PRT
<213> ORGANISM: Artificial Sequence
<220> FEATURE:
<223> OTHER INFORMATION: finger

<400> SEQUENCE: 121

Arg Ser Asp Ala Leu Thr Arg
 1               5

<210> SEQ ID NO 122
<211> LENGTH: 7
<212> TYPE: PRT
<213> ORGANISM: Artificial Sequence
<220> FEATURE:
<223> OTHER INFORMATION: finger

<400> SEQUENCE: 122

Arg Ser Asp Glu Leu Thr Arg
 1               5

<210> SEQ ID NO 123
<211> LENGTH: 7
<212> TYPE: PRT
<213> ORGANISM: Artificial Sequence
<220> FEATURE:
<223> OTHER INFORMATION: finger

<400> SEQUENCE: 123

Arg Ser Asp His Leu Thr Arg
 1               5

<210> SEQ ID NO 124
<211> LENGTH: 7
<212> TYPE: PRT
<213> ORGANISM: Artificial Sequence
<220> FEATURE:
```

```
<223> OTHER INFORMATION: finger

<400> SEQUENCE: 124

Gln Ser Gly Asp Leu Thr Arg
 1               5

<210> SEQ ID NO 125
<211> LENGTH: 7
<212> TYPE: PRT
<213> ORGANISM: Artificial Sequence
<220> FEATURE:
<223> OTHER INFORMATION: finger

<400> SEQUENCE: 125

Arg Ser Asp Glu Leu Thr Arg
 1               5

<210> SEQ ID NO 126
<211> LENGTH: 7
<212> TYPE: PRT
<213> ORGANISM: Artificial Sequence
<220> FEATURE:
<223> OTHER INFORMATION: finger

<400> SEQUENCE: 126

Asp Arg Ser Ala Leu Ala Arg
 1               5

<210> SEQ ID NO 127
<211> LENGTH: 7
<212> TYPE: PRT
<213> ORGANISM: Artificial Sequence
<220> FEATURE:
<223> OTHER INFORMATION: finger

<400> SEQUENCE: 127

Glu Arg Gly Asp Leu Thr Arg
 1               5

<210> SEQ ID NO 128
<211> LENGTH: 7
<212> TYPE: PRT
<213> ORGANISM: Artificial Sequence
<220> FEATURE:
<223> OTHER INFORMATION: finger

<400> SEQUENCE: 128

Arg Ser Asp Asn Leu Ala Arg
 1               5

<210> SEQ ID NO 129
<211> LENGTH: 7
<212> TYPE: PRT
<213> ORGANISM: Artificial Sequence
<220> FEATURE:
<223> OTHER INFORMATION: finger

<400> SEQUENCE: 129

Arg Ser Asp His Leu Ala Arg
 1               5

<210> SEQ ID NO 130
<211> LENGTH: 7
<212> TYPE: PRT
<213> ORGANISM: Artificial Sequence
<220> FEATURE:
<223> OTHER INFORMATION: finger
```

```
<400> SEQUENCE: 130

Arg Ser Asp His Leu Ala Arg
 1               5

<210> SEQ ID NO 131
<211> LENGTH: 7
<212> TYPE: PRT
<213> ORGANISM: Artificial Sequence
<220> FEATURE:
<223> OTHER INFORMATION: finger

<400> SEQUENCE: 131

Arg Ser Asp His Leu Ala Arg
 1               5

<210> SEQ ID NO 132
<211> LENGTH: 7
<212> TYPE: PRT
<213> ORGANISM: Artificial Sequence
<220> FEATURE:
<223> OTHER INFORMATION: finger

<400> SEQUENCE: 132

Arg Ser Asp Asn Leu Ala Arg
 1               5

<210> SEQ ID NO 133
<211> LENGTH: 7
<212> TYPE: PRT
<213> ORGANISM: Artificial Sequence
<220> FEATURE:
<223> OTHER INFORMATION: finger

<400> SEQUENCE: 133

Arg Ser Asp Asn Leu Ala Arg
 1               5

<210> SEQ ID NO 134
<211> LENGTH: 7
<212> TYPE: PRT
<213> ORGANISM: Artificial Sequence
<220> FEATURE:
<223> OTHER INFORMATION: finger

<400> SEQUENCE: 134

Asp Arg Ser Asn Leu Thr Arg
 1               5

<210> SEQ ID NO 135
<211> LENGTH: 7
<212> TYPE: PRT
<213> ORGANISM: Artificial Sequence
<220> FEATURE:
<223> OTHER INFORMATION: finger

<400> SEQUENCE: 135

Arg Ser Asp Ala Leu Thr Arg
 1               5

<210> SEQ ID NO 136
<211> LENGTH: 7
<212> TYPE: PRT
<213> ORGANISM: Artificial Sequence
<220> FEATURE:
<223> OTHER INFORMATION: finger
```

```
<400> SEQUENCE: 136

Gln Ser Gly His Leu Gln Arg
  1               5

<210> SEQ ID NO 137
<211> LENGTH: 7
<212> TYPE: PRT
<213> ORGANISM: Artificial Sequence
<220> FEATURE:
<223> OTHER INFORMATION: finger

<400> SEQUENCE: 137

Arg Ser Asp Ala Leu Thr Gln
  1               5

<210> SEQ ID NO 138
<211> LENGTH: 10
<212> TYPE: DNA
<213> ORGANISM: Artificial Sequence
<220> FEATURE:
<223> OTHER INFORMATION: target

<400> SEQUENCE: 138
gaagaggacc                                                          10

<210> SEQ ID NO 139
<211> LENGTH: 10
<212> TYPE: DNA
<213> ORGANISM: Artificial Sequence
<220> FEATURE:
<223> OTHER INFORMATION: target

<400> SEQUENCE: 139
gggggcgctc                                                          10

<210> SEQ ID NO 140
<211> LENGTH: 10
<212> TYPE: DNA
<213> ORGANISM: Artificial Sequence
<220> FEATURE:
<223> OTHER INFORMATION: target

<400> SEQUENCE: 140
gtgtggggtt                                                          10

<210> SEQ ID NO 141
<211> LENGTH: 10
<212> TYPE: DNA
<213> ORGANISM: Artificial Sequence
<220> FEATURE:
<223> OTHER INFORMATION: target

<400> SEQUENCE: 141
ggggcggggg                                                          10

<210> SEQ ID NO 142
<211> LENGTH: 10
<212> TYPE: DNA
<213> ORGANISM: Artificial Sequence
<220> FEATURE:
<223> OTHER INFORMATION: target

<400> SEQUENCE: 142
ggggaggatc                                                          10
```

```
<210> SEQ ID NO 143
<211> LENGTH: 10
<212> TYPE: DNA
<213> ORGANISM: Artificial Sequence
<220> FEATURE:
<223> OTHER INFORMATION: target

<400> SEQUENCE: 143 gctgggggck                                                          10

<210> SEQ ID NO 144
<211> LENGTH: 10
<212> TYPE: DNA
<213> ORGANISM: Artificial Sequence
<220> FEATURE:
<223> OTHER INFORMATION: target

<400> SEQUENCE: 144
gggggtgacc                                                          10

<210> SEQ ID NO 145
<211> LENGTH: 10
<212> TYPE: DNA
<213> ORGANISM: Artificial Sequence
<220> FEATURE:
<223> OTHER INFORMATION: target

<400> SEQUENCE: 145
gggggtgacc                                                          10

<210> SEQ ID NO 146
<211> LENGTH: 10
<212> TYPE: DNA
<213> ORGANISM: Artificial Sequence
<220> FEATURE:
<223> OTHER INFORMATION: target

<400> SEQUENCE: 146
aaggggagg                                                           10

<210> SEQ ID NO 147
<211> LENGTH: 10
<212> TYPE: DNA
<213> ORGANISM: Artificial Sequence
<220> FEATURE:
<223> OTHER INFORMATION: target

<400> SEQUENCE: 147
gcagggccg                                                           10

<210> SEQ ID NO 148
<211> LENGTH: 10
<212> TYPE: DNA
<213> ORGANISM: Artificial Sequence
<220> FEATURE:
<223> OTHER INFORMATION: target

<400> SEQUENCE: 148
gctggagcac                                                          10

<210> SEQ ID NO 149
<211> LENGTH: 7
<212> TYPE: PRT
<213> ORGANISM: Artificial Sequence
<220> FEATURE:
<223> OTHER INFORMATION: finger
```

```
<400> SEQUENCE: 149

Glu Lys Ala Asn Leu Thr Arg
1               5

<210> SEQ ID NO 150
<211> LENGTH: 7
<212> TYPE: PRT
<213> ORGANISM: Artificial Sequence
<220> FEATURE:
<223> OTHER INFORMATION: finger

<400> SEQUENCE: 150

Arg Ser Asp Asn Leu Thr Arg
1               5

<210> SEQ ID NO 151
<211> LENGTH: 7
<212> TYPE: PRT
<213> ORGANISM: Artificial Sequence
<220> FEATURE:
<223> OTHER INFORMATION: finger

<400> SEQUENCE: 151

Gln Arg Ser Asn Leu Val Arg
1               5

<210> SEQ ID NO 152
<211> LENGTH: 7
<212> TYPE: PRT
<213> ORGANISM: Artificial Sequence
<220> FEATURE:
<223> OTHER INFORMATION: finger

<400> SEQUENCE: 152

Gln Ser Ser Asp Leu Arg Arg
1               5

<210> SEQ ID NO 153
<211> LENGTH: 7
<212> TYPE: PRT
<213> ORGANISM: Artificial Sequence
<220> FEATURE:
<223> OTHER INFORMATION: finger

<400> SEQUENCE: 153

Gln Ser Ser His Leu Ala Arg
1               5

<210> SEQ ID NO 154
<211> LENGTH: 7
<212> TYPE: PRT
<213> ORGANISM: Artificial Sequence
<220> FEATURE:
<223> OTHER INFORMATION: finger

<400> SEQUENCE: 154

Arg Ser Asp His Leu Ser Arg
1               5

<210> SEQ ID NO 155
<211> LENGTH: 7
<212> TYPE: PRT
<213> ORGANISM: Artificial Sequence
<220> FEATURE:
<223> OTHER INFORMATION: finger

<400> SEQUENCE: 155
```

Gln Ser Ser His Leu Ala Arg
1               5

<210> SEQ ID NO 156
<211> LENGTH: 7
<212> TYPE: PRT
<213> ORGANISM: Artificial Sequence
<220> FEATURE:
<223> OTHER INFORMATION: finger

<400> SEQUENCE: 156

Arg Ser Asp His Leu Thr Thr
1               5

<210> SEQ ID NO 157
<211> LENGTH: 7
<212> TYPE: PRT
<213> ORGANISM: Artificial Sequence
<220> FEATURE:
<223> OTHER INFORMATION: finger

<400> SEQUENCE: 157

Arg Ser Asp Ala Leu Ala Arg
1               5

<210> SEQ ID NO 158
<211> LENGTH: 7
<212> TYPE: PRT
<213> ORGANISM: Artificial Sequence
<220> FEATURE:
<223> OTHER INFORMATION: finger

<400> SEQUENCE: 158

Lys Thr Ser His Leu Arg Ala
1               5

<210> SEQ ID NO 159
<211> LENGTH: 7
<212> TYPE: PRT
<213> ORGANISM: Artificial Sequence
<220> FEATURE:
<223> OTHER INFORMATION: finger

<400> SEQUENCE: 159

Arg Ser Asp Glu Leu Gln Arg
1               5

<210> SEQ ID NO 160
<211> LENGTH: 7
<212> TYPE: PRT
<213> ORGANISM: Artificial Sequence
<220> FEATURE:
<223> OTHER INFORMATION: finger

<400> SEQUENCE: 160

Arg Ser Asp His Leu Ser Lys
1               5

<210> SEQ ID NO 161
<211> LENGTH: 7
<212> TYPE: PRT
<213> ORGANISM: Artificial Sequence
<220> FEATURE:
<223> OTHER INFORMATION: finger

<400> SEQUENCE: 161

Thr Thr Ser Asn Leu Arg Arg
1               5

<210> SEQ ID NO 162
<211> LENGTH: 7
<212> TYPE: PRT
<213> ORGANISM: Artificial Sequence
<220> FEATURE:
<223> OTHER INFORMATION: finger

<400> SEQUENCE: 162

Arg Ser Ser Asn Leu Gln Arg
1               5

<210> SEQ ID NO 163
<211> LENGTH: 7
<212> TYPE: PRT
<213> ORGANISM: Artificial Sequence
<220> FEATURE:
<223> OTHER INFORMATION: finger

<400> SEQUENCE: 163

Arg Ser Asp His Leu Ser Arg
1               5

<210> SEQ ID NO 164
<211> LENGTH: 7
<212> TYPE: PRT
<213> ORGANISM: Artificial Sequence
<220> FEATURE:
<223> OTHER INFORMATION: finger

<400> SEQUENCE: 164

Asp Arg Ser His Leu Thr Arg
1               5

<210> SEQ ID NO 165
<211> LENGTH: 7
<212> TYPE: PRT
<213> ORGANISM: Artificial Sequence
<220> FEATURE:
<223> OTHER INFORMATION: finger

<400> SEQUENCE: 165

Arg Ser Asp His Leu Thr Arg
1               5

<210> SEQ ID NO 166
<211> LENGTH: 7
<212> TYPE: PRT
<213> ORGANISM: Artificial Sequence
<220> FEATURE:
<223> OTHER INFORMATION: finger

<400> SEQUENCE: 166

Gln Ser Ser Asp Leu Thr Arg
1               5

<210> SEQ ID NO 167
<211> LENGTH: 7
<212> TYPE: PRT
<213> ORGANISM: Artificial Sequence
<220> FEATURE:
<223> OTHER INFORMATION: finger

<400> SEQUENCE: 167

Asp Arg Ser Asn Leu Thr Arg

<210> SEQ ID NO 168
<211> LENGTH: 7
<212> TYPE: PRT
<213> ORGANISM: Artificial Sequence
<220> FEATURE:
<223> OTHER INFORMATION: finger

<400> SEQUENCE: 168

Thr Ser Gly His Leu Val Arg
1               5

<210> SEQ ID NO 169
<211> LENGTH: 7
<212> TYPE: PRT
<213> ORGANISM: Artificial Sequence
<220> FEATURE:
<223> OTHER INFORMATION: finger

<400> SEQUENCE: 169

Arg Ser Asp His Leu Ser Arg
1               5

<210> SEQ ID NO 170
<211> LENGTH: 7
<212> TYPE: PRT
<213> ORGANISM: Artificial Sequence
<220> FEATURE:
<223> OTHER INFORMATION: finger

<400> SEQUENCE: 170

Asp Arg Ser Asn Leu Thr Arg
1               5

<210> SEQ ID NO 171
<211> LENGTH: 7
<212> TYPE: PRT
<213> ORGANISM: Artificial Sequence
<220> FEATURE:
<223> OTHER INFORMATION: finger

<400> SEQUENCE: 171

Met Ser His His Leu Ser Arg
1               5

<210> SEQ ID NO 172
<211> LENGTH: 7
<212> TYPE: PRT
<213> ORGANISM: Artificial Sequence
<220> FEATURE:
<223> OTHER INFORMATION: finger

<400> SEQUENCE: 172

Arg Ser Asp His Leu Ser Arg
1               5

<210> SEQ ID NO 173
<211> LENGTH: 7
<212> TYPE: PRT
<213> ORGANISM: Artificial Sequence
<220> FEATURE:
<223> OTHER INFORMATION: finger

<400> SEQUENCE: 173

Arg Ser Asp Asn Leu Ala Arg
1               5

<210> SEQ ID NO 174
<211> LENGTH: 7
<212> TYPE: PRT
<213> ORGANISM: Artificial Sequence
<220> FEATURE:
<223> OTHER INFORMATION: finger

<400> SEQUENCE: 174

Arg Ser Asp His Leu Ser Arg
1               5

<210> SEQ ID NO 175
<211> LENGTH: 7
<212> TYPE: PRT
<213> ORGANISM: Artificial Sequence
<220> FEATURE:
<223> OTHER INFORMATION: finger

<400> SEQUENCE: 175

Arg Ser Asp Asn Leu Thr Gln
1               5

<210> SEQ ID NO 176
<211> LENGTH: 7
<212> TYPE: PRT
<213> ORGANISM: Artificial Sequence
<220> FEATURE:
<223> OTHER INFORMATION: finger

<400> SEQUENCE: 176

Asp Arg Ser Ser Leu Thr Arg
1               5

<210> SEQ ID NO 177
<211> LENGTH: 7
<212> TYPE: PRT
<213> ORGANISM: Artificial Sequence
<220> FEATURE:
<223> OTHER INFORMATION: finger

<400> SEQUENCE: 177

Arg Ser Asp His Leu Ser Arg
1               5

<210> SEQ ID NO 178
<211> LENGTH: 7
<212> TYPE: PRT
<213> ORGANISM: Artificial Sequence
<220> FEATURE:
<223> OTHER INFORMATION: finger

<400> SEQUENCE: 178

Gln Ser Gly Ser Leu Thr Arg
1               5

<210> SEQ ID NO 179
<211> LENGTH: 7
<212> TYPE: PRT
<213> ORGANISM: Artificial Sequence
<220> FEATURE:
<223> OTHER INFORMATION: finger

<400> SEQUENCE: 179

Gln Ser Gly Ser Leu Thr Arg
1               5

```
<210> SEQ ID NO 180
<211> LENGTH: 7
<212> TYPE: PRT
<213> ORGANISM: Artificial Sequence
<220> FEATURE:
<223> OTHER INFORMATION: finger

<400> SEQUENCE: 180

Gln Ser Gly His Leu Gln Arg
 1               5

<210> SEQ ID NO 181
<211> LENGTH: 7
<212> TYPE: PRT
<213> ORGANISM: Artificial Sequence
<220> FEATURE:
<223> OTHER INFORMATION: finger

<400> SEQUENCE: 181

Gln Ser Ser Asp Leu Thr Arg
 1               5

<210> SEQ ID NO 182
<211> LENGTH: 18
<212> TYPE: DNA
<213> ORGANISM: Artificial Sequence
<220> FEATURE:
<223> OTHER INFORMATION: target

<400> SEQUENCE: 182
ggagaggggg ccgcagtg                                                 18

<210> SEQ ID NO 183
<211> LENGTH: 19
<212> TYPE: DNA
<213> ORGANISM: Artificial Sequence
<220> FEATURE:
<223> OTHER INFORMATION: target

<400> SEQUENCE: 183
atggacgggt gaggcggcg                                                19

<210> SEQ ID NO 184
<211> LENGTH: 9
<212> TYPE: DNA
<213> ORGANISM: Artificial Sequence
<220> FEATURE:
<223> OTHER INFORMATION: target

<400> SEQUENCE: 184 gggggtgac                                                            9

<210> SEQ ID NO 185
<211> LENGTH: 9
<212> TYPE: DNA
<213> ORGANISM: Artificial Sequence
<220> FEATURE:
<223> OTHER INFORMATION: target

<400> SEQUENCE: 185 gctgggggc                                                            9

<210> SEQ ID NO 186
<211> LENGTH: 7
<212> TYPE: PRT
<213> ORGANISM: Artificial Sequence
```

```
<220> FEATURE:
<223> OTHER INFORMATION: recognition helix

<400> SEQUENCE: 186

Arg Ser Asp Ala Leu Thr Arg
 1               5

<210> SEQ ID NO 187
<211> LENGTH: 7
<212> TYPE: PRT
<213> ORGANISM: Artificial Sequence
<220> FEATURE:
<223> OTHER INFORMATION: recognition helix

<400> SEQUENCE: 187

Gln Ser Gly Asp Leu Thr Arg
 1               5

<210> SEQ ID NO 188
<211> LENGTH: 7
<212> TYPE: PRT
<213> ORGANISM: Artificial Sequence
<220> FEATURE:
<223> OTHER INFORMATION: recognition helix

<400> SEQUENCE: 188

Glu Arg Gly Asp Leu Thr Arg
 1               5

<210> SEQ ID NO 189
<211> LENGTH: 7
<212> TYPE: PRT
<213> ORGANISM: Artificial Sequence
<220> FEATURE:
<223> OTHER INFORMATION: recognition helix

<400> SEQUENCE: 189

Arg Ser Asp His Leu Ala Arg
 1               5

<210> SEQ ID NO 190
<211> LENGTH: 7
<212> TYPE: PRT
<213> ORGANISM: Artificial Sequence
<220> FEATURE:
<223> OTHER INFORMATION: recognition helix

<400> SEQUENCE: 190

Arg Ser Asp Asn Leu Ala Arg
 1               5

<210> SEQ ID NO 191
<211> LENGTH: 7
<212> TYPE: PRT
<213> ORGANISM: Artificial Sequence
<220> FEATURE:
<223> OTHER INFORMATION: recognition helix

<400> SEQUENCE: 191

Gln Ser Ser His Leu Ala Arg
 1               5

<210> SEQ ID NO 192
<211> LENGTH: 7
<212> TYPE: PRT
<213> ORGANISM: Artificial Sequence
<220> FEATURE:
```

<223> OTHER INFORMATION: recognition helix

<400> SEQUENCE: 192

Arg Ser Asp Glu Leu Thr Arg
1               5

<210> SEQ ID NO 193
<211> LENGTH: 7
<212> TYPE: PRT
<213> ORGANISM: Artificial Sequence
<220> FEATURE:
<223> OTHER INFORMATION: recognition helix

<400> SEQUENCE: 193

Arg Ser Asp Glu Leu Gln Arg
1               5

<210> SEQ ID NO 194
<211> LENGTH: 7
<212> TYPE: PRT
<213> ORGANISM: Artificial Sequence
<220> FEATURE:
<223> OTHER INFORMATION: recognition helix

<400> SEQUENCE: 194

Arg Ser Asp Asn Leu Ala Arg
1               5

<210> SEQ ID NO 195
<211> LENGTH: 7
<212> TYPE: PRT
<213> ORGANISM: Artificial Sequence
<220> FEATURE:
<223> OTHER INFORMATION: recognition helix

<400> SEQUENCE: 195

Arg Ser Asp His Leu Ala Arg
1               5

<210> SEQ ID NO 196
<211> LENGTH: 7
<212> TYPE: PRT
<213> ORGANISM: Artificial Sequence
<220> FEATURE:
<223> OTHER INFORMATION: recognition helix

<400> SEQUENCE: 196

Asp Arg Ser Asn Leu Thr Arg
1               5

<210> SEQ ID NO 197
<211> LENGTH: 7
<212> TYPE: PRT
<213> ORGANISM: Artificial Sequence
<220> FEATURE:
<223> OTHER INFORMATION: recognition helix

<400> SEQUENCE: 197

Arg Ser Asp Ala Leu Thr Gln
1               5

<210> SEQ ID NO 198
<211> LENGTH: 7
<212> TYPE: PRT
<213> ORGANISM: Artificial Sequence
<220> FEATURE:
<223> OTHER INFORMATION: recognition helix

```
<400> SEQUENCE: 198

Asp Arg Ser Asn Leu Thr Arg
  1               5

<210> SEQ ID NO 199
<211> LENGTH: 7
<212> TYPE: PRT
<213> ORGANISM: Artificial Sequence
<220> FEATURE:
<223> OTHER INFORMATION: recognition helix

<400> SEQUENCE: 199

Met Ser His His Leu Ser Arg
  1               5

<210> SEQ ID NO 200
<211> LENGTH: 7
<212> TYPE: PRT
<213> ORGANISM: Artificial Sequence
<220> FEATURE:
<223> OTHER INFORMATION: recognition helix

<400> SEQUENCE: 200

Arg Ser Asp His Leu Ser Arg
  1               5

<210> SEQ ID NO 201
<211> LENGTH: 7
<212> TYPE: PRT
<213> ORGANISM: Artificial Sequence
<220> FEATURE:
<223> OTHER INFORMATION: recognition helix

<400> SEQUENCE: 201

Asp Arg Ser His Leu Thr Arg
  1               5

<210> SEQ ID NO 202
<211> LENGTH: 7
<212> TYPE: PRT
<213> ORGANISM: Artificial Sequence
<220> FEATURE:
<223> OTHER INFORMATION: recognition helix

<400> SEQUENCE: 202

Arg Ser Asp His Leu Thr Arg
  1               5

<210> SEQ ID NO 203
<211> LENGTH: 7
<212> TYPE: PRT
<213> ORGANISM: Artificial Sequence
<220> FEATURE:
<223> OTHER INFORMATION: recognition helix

<400> SEQUENCE: 203

Gln Ser Ser Asp Leu Thr Arg
  1               5

<210> SEQ ID NO 204
<211> LENGTH: 20
<212> TYPE: DNA
<213> ORGANISM: Artificial Sequence
<220> FEATURE:
<223> OTHER INFORMATION: VEGF-C forward primer
```

```
<400> SEQUENCE: 204
tgccgatgca tgtctaaact                                              20

<210> SEQ ID NO 205
<211> LENGTH: 22
<212> TYPE: DNA
<213> ORGANISM: Artificial Sequence
<220> FEATURE:
<223> OTHER INFORMATION: VEGF-C reverse primer

<400> SEQUENCE: 205
tgaacaggtc tcttcatcca gc                                           22

<210> SEQ ID NO 206
<211> LENGTH: 26
<212> TYPE: DNA
<213> ORGANISM: Artificial Sequence
<220> FEATURE:
<223> OTHER INFORMATION: VEGF-C probe
<221> NAME/KEY: modified_base
<222> LOCATION: (1)...(1)
<223> OTHER INFORMATION: n = c modified by aminofluorescein (FAM)
<221> NAME/KEY: modified_base
<222> LOCATION: (26)...(26)
<223> OTHER INFORMATION: n = a modified by tetramethylrhodamine (TAMRA)

<400> SEQUENCE: 206
nagcaacact accacagtgt caggcn                                       26

<210> SEQ ID NO 207
<211> LENGTH: 19
<212> TYPE: DNA
<213> ORGANISM: Artificial Sequence
<220> FEATURE:
<223> OTHER INFORMATION: target

<400> SEQUENCE: 207
tgagcggcgg cagcggagc                                               19

<210> SEQ ID NO 208
<211> LENGTH: 25
<212> TYPE: PRT
<213> ORGANISM: Artificial Sequence
<220> FEATURE:
<223> OTHER INFORMATION: exemplary DNA-binding subdomain motif of C-2H-2
      class of zinc finger proteins (ZFP)
<221> NAME/KEY: MOD_RES
<222> LOCATION: (2)...(5)
<223> OTHER INFORMATION: Xaa = any amino acid, Xaa in positions 4 and 5
      may be present or absent
<221> NAME/KEY: MOD_RES
<222> LOCATION: (7)...(18)
<223> OTHER INFORMATION: Xaa = any amino acid
<221> NAME/KEY: MOD_RES
<222> LOCATION: (20)...(24)
<223> OTHER INFORMATION: Xaa = any amino acid, Xaa in positions 23 and
      24 may be present or absent

<400> SEQUENCE: 208

Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 209
<211> LENGTH: 9
<212> TYPE: DNA
<213> ORGANISM: Artificial Sequence
```

```
<220> FEATURE:
<223> OTHER INFORMATION: target

<400> SEQUENCE: 209 ggcgtagac                                                                9

<210> SEQ ID NO 210
<211> LENGTH: 9
<212> TYPE: DNA
<213> ORGANISM: Artificial Sequence
<220> FEATURE:
<223> OTHER INFORMATION: target

<400> SEQUENCE: 210 ggcgacgta                                                                9

<210> SEQ ID NO 211
<211> LENGTH: 5
<212> TYPE: PRT
<213> ORGANISM: Artificial Sequence
<220> FEATURE:
<223> OTHER INFORMATION: peptide linker

<400> SEQUENCE: 211

Thr Gly Glu Lys Pro
  1               5

<210> SEQ ID NO 212
<211> LENGTH: 5
<212> TYPE: PRT
<213> ORGANISM: Artificial Sequence
<220> FEATURE:
<223> OTHER INFORMATION: peptide linker

<400> SEQUENCE: 212

Gly Gly Gly Gly Ser
  1               5

<210> SEQ ID NO 213
<211> LENGTH: 8
<212> TYPE: PRT
<213> ORGANISM: Artificial Sequence
<220> FEATURE:
<223> OTHER INFORMATION: peptide linker

<400> SEQUENCE: 213

Gly Gly Arg Arg Gly Gly Gly Ser
  1               5

<210> SEQ ID NO 214
<211> LENGTH: 9
<212> TYPE: PRT
<213> ORGANISM: Artificial Sequence
<220> FEATURE:
<223> OTHER INFORMATION: peptide linker

<400> SEQUENCE: 214

Leu Arg Gln Arg Asp Gly Glu Arg Pro
  1               5

<210> SEQ ID NO 215
<211> LENGTH: 12
<212> TYPE: PRT
<213> ORGANISM: Artificial Sequence
<220> FEATURE:
<223> OTHER INFORMATION: peptide linker
```

```
<400> SEQUENCE: 215

Leu Arg Gln Lys Asp Gly Gly Gly Ser Glu Arg Pro
 1               5                  10

<210> SEQ ID NO 216
<211> LENGTH: 16
<212> TYPE: PRT
<213> ORGANISM: Artificial Sequence
<220> FEATURE:
<223> OTHER INFORMATION: peptide linker

<400> SEQUENCE: 216

Leu Arg Gln Lys Asp Gly Gly Gly Ser Gly Gly Gly Ser Glu Arg Pro
 1               5                  10                  15

<210> SEQ ID NO 217
<211> LENGTH: 30
<212> TYPE: PRT
<213> ORGANISM: Artificial Sequence
<220> FEATURE:
<223> OTHER INFORMATION: F1 DNA binding domain of mouse transcription
      factor Zif268

<400> SEQUENCE: 217

Tyr Ala Cys Pro Val Glu Ser Cys Asp Arg Arg Phe Ser Arg Ser Asp
 1               5                  10                  15

Glu Leu Thr Arg His Ile Arg Ile His Thr Gly Gln Lys Pro
            20                  25                  30

<210> SEQ ID NO 218
<211> LENGTH: 28
<212> TYPE: PRT
<213> ORGANISM: Artificial Sequence
<220> FEATURE:
<223> OTHER INFORMATION: F2 DNA binding domain of mouse transcription
      factor Zif268

<400> SEQUENCE: 218

Phe Gln Cys Arg Ile Cys Met Arg Asn Phe Ser Arg Ser Asp His Leu
 1               5                  10                  15

Thr Thr His Ile Arg Thr His Thr Gly Glu Lys Pro
            20                  25

<210> SEQ ID NO 219
<211> LENGTH: 27
<212> TYPE: PRT
<213> ORGANISM: Artificial Sequence
<220> FEATURE:
<223> OTHER INFORMATION: F3 DNA binding domain of mouse transcription
      factor Zif268

<400> SEQUENCE: 219

Phe Ala Cys Asp Ile Cys Gly Arg Lys Phe Ala Arg Ser Asp Glu Arg
 1               5                  10                  15

Lys Arg His Thr Lys Ile His Leu Arg Gln Lys
            20                  25

<210> SEQ ID NO 220
<211> LENGTH: 9
<212> TYPE: DNA
<213> ORGANISM: Artificial Sequence
<220> FEATURE:
<223> OTHER INFORMATION: mouse transcription factor Zif268 target

<400> SEQUENCE: 220
```

-continued gcgtgggcg 9

<210> SEQ ID NO 221
<211> LENGTH: 94
<212> TYPE: PRT
<213> ORGANISM: Artificial Sequence
<220> FEATURE:
<223> OTHER INFORMATION: Sp-1 transcription factor

<400> SEQUENCE: 221

```
Pro Gly Lys Lys Gln His Ile Cys His Ile Gln Gly Cys Gly Lys
 1               5                  10                  15

Val Tyr Gly Lys Thr Ser His Leu Arg Ala His Leu Arg Trp His Thr
                20                  25                  30

Gly Glu Arg Pro Phe Met Cys Thr Trp Ser Tyr Cys Gly Lys Arg Phe
            35                  40                  45

Thr Arg Ser Asp Glu Leu Gln Arg His Lys Arg Thr His Thr Gly Glu
        50                  55                  60

Lys Lys Phe Ala Cys Pro Glu Cys Pro Lys Arg Phe Met Arg Ser Asp
65                  70                  75                  80

His Leu Ser Lys His Ile Lys Thr His Gln Asn Lys Lys Gly
                85                  90
```

<210> SEQ ID NO 222
<211> LENGTH: 9
<212> TYPE: DNA
<213> ORGANISM: Artificial Sequence
<220> FEATURE:
<223> OTHER INFORMATION: Sp-1 optimal target consensus sequence

<400> SEQUENCE: 222 ggggcgggg 9

<210> SEQ ID NO 223
<211> LENGTH: 100
<212> TYPE: PRT
<213> ORGANISM: Artificial Sequence
<220> FEATURE:
<223> OTHER INFORMATION: Sp-i consensus sequence with leader sequence

<400> SEQUENCE: 223

```
Met Glu Lys Leu Arg Asn Gly Ser Gly Asp Pro Gly Lys Lys Lys Gln
 1               5                  10                  15

His Ala Cys Pro Glu Cys Gly Lys Ser Phe Ser Lys Ser Ser His Leu
                20                  25                  30

Arg Ala His Gln Arg Thr His Thr Gly Glu Arg Pro Tyr Lys Cys Pro
            35                  40                  45

Glu Cys Gly Lys Ser Phe Ser Arg Ser Asp Glu Leu Gln Arg His Gln
        50                  55                  60

Arg Thr His Thr Gly Glu Lys Pro Tyr Lys Cys Pro Glu Cys Gly Lys
65                  70                  75                  80

Ser Phe Ser Arg Ser Asp His Leu Ser Lys His Gln Arg Thr His Gln
                85                  90                  95

Asn Lys Lys Gly
            100
```

<210> SEQ ID NO 224
<211> LENGTH: 7
<212> TYPE: PRT
<213> ORGANISM: Artificial Sequence
<220> FEATURE:

```
<223> OTHER INFORMATION: N-terminal nucler localization signal from SV40
      large T antigen

<400> SEQUENCE: 224

Pro Lys Lys Lys Arg Lys Val
1               5

<210> SEQ ID NO 225
<211> LENGTH: 8
<212> TYPE: PRT
<213> ORGANISM: Artificial Sequence
<220> FEATURE:
<223> OTHER INFORMATION: FLAG peptide

<400> SEQUENCE: 225

Asp Tyr Lys Asp Asp Asp Asp Lys
1               5

<210> SEQ ID NO 226
<211> LENGTH: 21
<212> TYPE: DNA
<213> ORGANISM: Artificial Sequence
<220> FEATURE:
<223> OTHER INFORMATION: VEGF-A forward primer

<400> SEQUENCE: 226
gtgcattgga gccttgcctt g                                           21

<210> SEQ ID NO 227
<211> LENGTH: 22
<212> TYPE: DNA
<213> ORGANISM: Artificial Sequence
<220> FEATURE:
<223> OTHER INFORMATION: VEGF-A reverse primer

<400> SEQUENCE: 227
actcgatctc atcagggtac tc                                          22

<210> SEQ ID NO 228
<211> LENGTH: 25
<212> TYPE: DNA
<213> ORGANISM: Artificial Sequence
<220> FEATURE:
<223> OTHER INFORMATION: VEGF-A Taqman probe
<221> NAME/KEY: modified_base
<222> LOCATION: (1)...(1)
<223> OTHER INFORMATION: n = c modified by aminofluorescein (FAM)
<221> NAME/KEY: modified_base
<222> LOCATION: (25)...(25)
<223> OTHER INFORMATION: n = a modified by tetramethylrhodamine (TAMRA)

<400> SEQUENCE: 228
nagtagctgc gctgatagac atccn                                       25

<210> SEQ ID NO 229
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 229
ccatgttcgt catgggtgtg a                                           21

<210> SEQ ID NO 230
<211> LENGTH: 20
<212> TYPE: DNA
```

```
<213> ORGANISM: Artificial Sequence
<220> FEATURE:
<223> OTHER INFORMATION: GAPDH reverse primer

<400> SEQUENCE: 230
catggactgt ggtcatgagt                                               20

<210> SEQ ID NO 231
<211> LENGTH: 24
<212> TYPE: DNA
<213> ORGANISM: Artificial Sequence
<220> FEATURE:
<223> OTHER INFORMATION: GAPDH Taqman probe
<221> NAME/KEY: modified_base
<222> LOCATION: (1)...(1)
<223> OTHER INFORMATION: n = t modified by aminofluorescein (FAM)
<221> NAME/KEY: modified_base
<222> LOCATION: (24)...(24)
<223> OTHER INFORMATION: n = a modified by tetramethylrhodamine (TAMRA)

<400> SEQUENCE: 231
ncctgcacca ccaactgctt agcn                                          24

<210> SEQ ID NO 232
<211> LENGTH: 20
<212> TYPE: DNA
<213> ORGANISM: Artificial Sequence
<220> FEATURE:
<223> OTHER INFORMATION: VP16-FLAG forward primer

<400> SEQUENCE: 232
catgacgatt tcgatctgga                                               20

<210> SEQ ID NO 233
<211> LENGTH: 22
<212> TYPE: DNA
<213> ORGANISM: Artificial Sequence
<220> FEATURE:
<223> OTHER INFORMATION: VP16-FLAG reverse primer

<400> SEQUENCE: 233
ctacttgtca tcgtcgtcct tg                                            22

<210> SEQ ID NO 234
<211> LENGTH: 26
<212> TYPE: DNA
<213> ORGANISM: Artificial Sequence
<220> FEATURE:
<223> OTHER INFORMATION: VP16-FLAG Taqman probe
<221> NAME/KEY: modified_base
<222> LOCATION: (1)...(1)
<223> OTHER INFORMATION: n = a modified by aminofluorescein (FAM)
<221> NAME/KEY: modified_base
<222> LOCATION: (26)...(26)
<223> OTHER INFORMATION: n = a modified by tetramethylrhodamine (TAMRA)

<400> SEQUENCE: 234
ntcggtaaac atctgctcaa actcgn                                        26

<210> SEQ ID NO 235
<211> LENGTH: 28
<212> TYPE: DNA
<213> ORGANISM: Artificial Sequence
<220> FEATURE:
<223> OTHER INFORMATION: RT-PCR primer

<400> SEQUENCE: 235
atgaactttc tgctgtcttg ggtgcatt                                      28
```

<210> SEQ ID NO 236
<211> LENGTH: 22
<212> TYPE: DNA
<213> ORGANISM: Artificial Sequence
<220> FEATURE:
<223> OTHER INFORMATION: RT-PCR primer

<400> SEQUENCE: 236
tcaccgcctc ggcttgtcac at                                              22

<210> SEQ ID NO 237
<211> LENGTH: 18
<212> TYPE: DNA
<213> ORGANISM: Artificial Sequence
<220> FEATURE:
<223> OTHER INFORMATION: murine VEGF target

<400> SEQUENCE: 237
tgagcggcgg cagcggag                                                   18

<210> SEQ ID NO 238
<211> LENGTH: 7
<212> TYPE: PRT
<213> ORGANISM: Artificial Sequence
<220> FEATURE:
<223> OTHER INFORMATION: recognition helix

<400> SEQUENCE: 238

Arg Ser Asp Glu Leu Ser rg
 1               5

<210> SEQ ID NO 239
<211> LENGTH: 7
<212> TYPE: PRT
<213> ORGANISM: Artificial Sequence
<220> FEATURE:
<223> OTHER INFORMATION: recognition helix

<400> SEQUENCE: 239

Gln Ser Gly His Leu Thr Lys
 1               5

<210> SEQ ID NO 240
<211> LENGTH: 10
<212> TYPE: DNA
<213> ORGANISM: Artificial Sequence
<220> FEATURE:
<223> OTHER INFORMATION: target

<400> SEQUENCE: 240
gctgggggcg                                                            10

<210> SEQ ID NO 241
<211> LENGTH: 49
<212> TYPE: DNA
<213> ORGANISM: Artificial Sequence
<220> FEATURE:
<223> OTHER INFORMATION: primer

<400> SEQUENCE: 241
cccagatctg gtgatggcaa gaagaagcag caccatctgc cacatccag                 49

<210> SEQ ID NO 242
<211> LENGTH: 37
<212> TYPE: DNA

```
<213> ORGANISM: Artificial Sequence
<220> FEATURE:
<223> OTHER INFORMATION: primer

<400> SEQUENCE: 242
cccaagctta ggatccaccc ttcttgttct ggtgggt                                  37

<210> SEQ ID NO 243
<211> LENGTH: 18
<212> TYPE: PRT
<213> ORGANISM: Artificial Sequence
<220> FEATURE:
<223> OTHER INFORMATION: VZ+57

<400> SEQUENCE: 243

His Gln Asn Lys Lys Gly Gly Ser Gly Asp Gly Lys Lys Lys Gln His
 1               5                  10                  15

Ile Cys

<210> SEQ ID NO 244
<211> LENGTH: 9
<212> TYPE: DNA
<213> ORGANISM: Artificial Sequence
<220> FEATURE:
<223> OTHER INFORMATION: target

<400> SEQUENCE: 244 gaggcttgg                                                                  9

<210> SEQ ID NO 245
<211> LENGTH: 7
<212> TYPE: PRT
<213> ORGANISM: Artificial Sequence
<220> FEATURE:
<223> OTHER INFORMATION: finger

<400> SEQUENCE: 245

Thr Ser Gly His Leu Thr Arg
 1               5

<210> SEQ ID NO 246
<211> LENGTH: 7
<212> TYPE: PRT
<213> ORGANISM: Artificial Sequence
<220> FEATURE:
<223> OTHER INFORMATION: finger

<400> SEQUENCE: 246

Thr Ser Gly His Leu Ile Arg
 1               5

<210> SEQ ID NO 247
<211> LENGTH: 7
<212> TYPE: PRT
<213> ORGANISM: Artificial Sequence
<220> FEATURE:
<223> OTHER INFORMATION: finger

<400> SEQUENCE: 247

Thr Ser Gly His Leu Ser Arg
 1               5

<210> SEQ ID NO 248
<211> LENGTH: 7
<212> TYPE: PRT
<213> ORGANISM: Artificial Sequence
```

```
<220> FEATURE:
<223> OTHER INFORMATION: finger

<400> SEQUENCE: 248

Thr Ser Gly His Leu Ala Arg
 1               5

<210> SEQ ID NO 249
<211> LENGTH: 7
<212> TYPE: PRT
<213> ORGANISM: Artificial Sequence
<220> FEATURE:
<223> OTHER INFORMATION: finger

<400> SEQUENCE: 249

Thr Ser Gly His Leu Arg Arg
 1               5

<210> SEQ ID NO 250
<211> LENGTH: 7
<212> TYPE: PRT
<213> ORGANISM: Artificial Sequence
<220> FEATURE:
<223> OTHER INFORMATION: finger

<400> SEQUENCE: 250

Thr Ala Gly His Leu Val Arg
 1               5

<210> SEQ ID NO 251
<211> LENGTH: 7
<212> TYPE: PRT
<213> ORGANISM: Artificial Sequence
<220> FEATURE:
<223> OTHER INFORMATION: finger

<400> SEQUENCE: 251

Thr Thr Gly His Leu Val Arg
 1               5

<210> SEQ ID NO 252
<211> LENGTH: 7
<212> TYPE: PRT
<213> ORGANISM: Artificial Sequence
<220> FEATURE:
<223> OTHER INFORMATION: finger

<400> SEQUENCE: 252

Thr Lys Asp His Leu Val Arg
 1               5
```